(12) United States Patent
VanAntwerp et al.

(10) Patent No.: US 9,616,107 B2
(45) Date of Patent: Apr. 11, 2017

(54) THERAPY FOR KIDNEY DISEASE AND/OR HEART FAILURE

(71) Applicant: Capricor Therapeutics, Inc., Beverly Hills, CA (US)

(72) Inventors: William P. VanAntwerp, Valencia, CA (US); Andrew J. L. Walsh, Minneapolis, MN (US); VenKatesh R. Manda, Stillwater, MN (US); John Burnes, Coon Rapids, MN (US)

(73) Assignee: Capricor Therapeutics, Inc., Beverly Hills, CA (US)

( * ) Notice: Subject to any disclaimer, the term of this patent is extended or adjusted under 35 U.S.C. 154(b) by 0 days.

(21) Appl. No.: 14/555,016

(22) Filed: Nov. 26, 2014

(65) Prior Publication Data

US 2015/0190473 A1    Jul. 9, 2015

Related U.S. Application Data

(63) Continuation of application No. 13/368,285, filed on Feb. 7, 2012, now abandoned.

(60) Provisional application No. 61/446,995, filed on Feb. 25, 2011, provisional application No. 61/511,509, filed on Jul. 25, 2011, provisional application No. 61/550,896, filed on Oct. 24, 2011, provisional application No. 61/565,911, filed on Dec. 1, 2011.

(51) Int. Cl.

| | | |
|---|---|---|
| *A61K 38/22* | (2006.01) | |
| *A61K 38/00* | (2006.01) | |
| *A61K 38/16* | (2006.01) | |
| *A61K 38/10* | (2006.01) | |
| *A61K 9/00* | (2006.01) | |
| *A61K 47/18* | (2017.01) | |
| *A61M 5/142* | (2006.01) | |

(52) U.S. Cl.
CPC ........ *A61K 38/2242* (2013.01); *A61K 9/0019* (2013.01); *A61K 47/18* (2013.01); *A61M 5/14228* (2013.01); *A61M 5/14276* (2013.01)

(58) Field of Classification Search
None
See application file for complete search history.

(56) References Cited

U.S. PATENT DOCUMENTS

| | | |
|---|---|---|
| 4,508,712 A | 4/1985 | Needleman |
| 4,562,751 A | 1/1986 | Nason et al. |
| 4,569,641 A | 2/1986 | Falk et al. |
| 4,685,903 A | 8/1987 | Cable et al. |
| 4,751,284 A | 6/1988 | Forssmann |
| 4,761,469 A | 8/1988 | DeBold |
| 4,764,504 A | 8/1988 | Johnson et al. |
| 4,782,044 A | 11/1988 | Forssmann |
| 4,851,349 A | 7/1989 | Nakanishi et al. |
| 4,883,467 A | 11/1989 | Franetski et al. |
| 4,895,932 A | 1/1990 | Forssmann |
| 5,080,653 A | 1/1992 | Voss et al. |
| 5,097,122 A | 3/1992 | Colman et al. |
| 5,135,912 A | 8/1992 | Wiedemann et al. |
| 5,202,239 A | 4/1993 | Tarnowski et al. |
| 5,212,286 A | 5/1993 | Lewicki et al. |
| 5,395,340 A | 3/1995 | Lee |
| 5,505,709 A | 4/1996 | Funderburk et al. |
| 5,665,704 A | 9/1997 | Lowe et al. |
| 5,691,310 A | 11/1997 | Vesely |
| 5,846,932 A | 12/1998 | Lowe et al. |
| 5,948,761 A | 9/1999 | Seilhamer et al. |
| 6,136,564 A | 10/2000 | Kopetzki |
| 6,372,499 B1 | 4/2002 | Midoux et al. |
| 6,407,211 B1 | 6/2002 | Burnett et al. |
| 6,423,035 B1 | 7/2002 | Das et al. |
| 6,525,022 B1 | 2/2003 | Lowe et al. |
| 6,541,939 B2 | 4/2003 | Kishibe et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,629,954 B1 | 10/2003 | Heruth |
| 6,641,533 B2 | 11/2003 | Causet, III et al. |
| 6,652,493 B1 | 11/2003 | Das |
| 6,656,148 B2 | 12/2003 | Das et al. |
| 6,659,980 B2 | 12/2003 | Moberg et al. |
| 6,752,787 B1 | 6/2004 | Causey, III et al. |

(Continued)

FOREIGN PATENT DOCUMENTS

| | | |
|---|---|---|
| EP | 180615 A1 | 5/1986 |
| EP | 465097 A2 | 1/1992 |

(Continued)

OTHER PUBLICATIONS www.mayoclinic.com/health/kidney-failure/DS00682/DSECTION=treatments-and-drugs May 13, 2008, downloaded Oct. 5, 2012).*
Abd-Eisalam et al. 2011. "What is the Optimum Concentration of m-cresol in antivenoms?" J. Venomous Animals and Toxins, ISSN 1678-9199, vol. 17(1):12-22.
Brenner et al., 1990. "Diverse Biological Actions of Atrial Natriuretic Peptide," Physiol. Rev., 70(3):665-669.

(Continued)

*Primary Examiner* — Shulamith H Shafer
(74) *Attorney, Agent, or Firm* — Knowles IP Strategies, LLC

(57) ABSTRACT

Medical systems and methods for treating kidney disease alone, heart failure alone, chronic kidney disease with concomitant heart failure, or cardiorenal syndrome are described. The systems and methods are based on delivery of a natriuretic peptide such as Vessel Dilator to a subject. Methods for increasing and maintaining peptide levels at a certain concentration include direct peptide delivery via either an external or implantable programmable pump.

13 Claims, 31 Drawing Sheets

(56) References Cited

U.S. PATENT DOCUMENTS

| | | |
|---|---|---|
| 6,800,071 B1 | 10/2004 | McConnell et al. |
| 6,817,990 B2 | 11/2004 | Yap et al. |
| 6,833,358 B1 | 12/2004 | Nakata |
| 6,849,714 B1 | 2/2005 | Bridon et al. |
| 6,872,200 B2 | 3/2005 | Mann et al. |
| 6,887,470 B1 | 5/2005 | Bridon et al. |
| 6,897,030 B2 | 5/2005 | Seilhamer et al. |
| 6,932,584 B2 | 8/2005 | Gray et al. |
| 6,936,029 B2 | 8/2005 | Mann et al. |
| 6,974,861 B2 | 12/2005 | Seilhamer et al. |
| 6,979,326 B2 | 12/2005 | Mann et al. |
| 6,997,920 B2 | 2/2006 | Mann et al. |
| 7,025,743 B2 | 4/2006 | Mann et al. |
| 7,026,293 B2 | 4/2006 | Kitakaze |
| 7,033,997 B2 | 4/2006 | Forssmann et al. |
| 7,179,790 B2 | 2/2007 | Seilhamer et al. |
| 7,256,253 B2 | 8/2007 | Bridon et al. |
| 7,276,481 B2 | 10/2007 | Golembo et al. |
| 7,288,085 B2 | 10/2007 | Olsen et al. |
| 7,341,838 B2 | 3/2008 | Buechler et al. |
| 7,384,917 B2 | 6/2008 | Burnett, Jr. et al. |
| 7,414,107 B2 | 8/2008 | Larsen |
| 7,569,384 B2 | 8/2009 | Rosen et al. |
| 7,585,837 B2 | 9/2009 | Shechter et al. |
| 7,642,243 B2 | 1/2010 | Nakao et al. |
| 7,648,962 B2 | 1/2010 | James et al. |
| 7,655,772 B2 | 2/2010 | Mohapatra |
| 7,662,773 B2 | 2/2010 | James et al. |
| 7,714,100 B2 | 5/2010 | Cohen et al. |
| 7,754,852 B2 | 7/2010 | Burnett, Jr. et al. |
| 7,917,208 B2 | 3/2011 | Yomtov et al. |
| 8,455,438 B2 | 6/2013 | Burnett, Jr. et al. |
| 8,501,693 B2 | 8/2013 | Kim et al. |
| 2002/0082219 A1 | 6/2002 | Burnett, Jr. et al. |
| 2003/0069186 A1 | 4/2003 | Burnett, Jr. et al. |
| 2004/0053245 A1 | 3/2004 | Tang et al. |
| 2004/0077537 A1 | 4/2004 | Schreiner |
| 2004/0106953 A1 | 6/2004 | Yomtov et al. |
| 2004/0138134 A1 | 7/2004 | Golembo et al. |
| 2004/0176914 A1 | 9/2004 | Buechler et al. |
| 2004/0203081 A1 | 10/2004 | James et al. |
| 2005/0059600 A1 | 3/2005 | Burnett, Jr. et al. |
| 2005/0064511 A1 | 3/2005 | Buechler et al. |
| 2005/0065760 A1 | 3/2005 | Murtfeldt et al. |
| 2005/0106592 A1 | 5/2005 | Schleuning et al. |
| 2005/0113286 A1 | 5/2005 | Schreiner |
| 2005/0232981 A1 | 10/2005 | Ben-Sasson |
| 2005/0244904 A1 | 11/2005 | Ng |
| 2005/0272650 A1 | 12/2005 | Mohapatra |
| 2006/0025367 A1 | 2/2006 | Simari |
| 2006/0052764 A1 | 3/2006 | Gelfand et al. |
| 2006/0074009 A1 | 4/2006 | James et al. |
| 2006/0110359 A1 | 5/2006 | Sanchez-Ramos et al. |
| 2006/0172933 A1 | 8/2006 | James et al. |
| 2006/0205642 A1 | 9/2006 | Vesely et al. |
| 2006/0264376 A1 | 11/2006 | Mitrovic et al. |
| 2006/0276382 A1 | 12/2006 | Mohapatra |
| 2007/0027306 A1 | 2/2007 | Rosen et al. |
| 2007/0042957 A1 | 2/2007 | Burnett, Jr. et al. |
| 2007/0048282 A1 | 3/2007 | Rosen et al. |
| 2007/0197434 A1 | 8/2007 | Nakao et al. |
| 2008/0004206 A1 | 1/2008 | Rosen et al. |
| 2008/0015152 A1 | 1/2008 | Larsen et al. |
| 2008/0032933 A1 | 2/2008 | Burnett, Jr. et al. |
| 2008/0039394 A1 | 2/2008 | Vesely |
| 2008/0051716 A1 | 2/2008 | Stutz |
| 2008/0070858 A1 | 3/2008 | Mohapatra |
| 2008/0139785 A1 | 6/2008 | Larsen |
| 2008/0153747 A1 | 6/2008 | Alewood et al. |
| 2008/0163747 A1 | 7/2008 | Uehara et al. |
| 2008/0188796 A1 | 8/2008 | Steil et al. |
| 2008/0194481 A1 | 8/2008 | Rosen et al. |
| 2008/0194682 A1 | 8/2008 | Golembo et al. |
| 2008/0207505 A1 | 8/2008 | James |
| 2008/0214437 A1 | 9/2008 | Mohapatra et al. |
| 2008/0227954 A1 | 9/2008 | Larsen |
| 2008/0234467 A1 | 9/2008 | Larsen |
| 2008/0312142 A1 | 12/2008 | Nakao et al. |
| 2008/0312157 A1 | 12/2008 | Levy et al. |
| 2009/0011997 A1 | 1/2009 | Peri et al. |
| 2009/0035287 A1 | 2/2009 | Levine et al. |
| 2009/0036364 A1 | 2/2009 | Levy et al. |
| 2009/0062206 A1 | 3/2009 | Vesely |
| 2009/0062730 A1 | 3/2009 | Woo |
| 2009/0069243 A1 | 3/2009 | Burnett, Jr. et al. |
| 2009/0093408 A1 | 4/2009 | Bridon et al. |
| 2009/0170196 A1 | 7/2009 | Vesely |
| 2009/0170756 A1 | 7/2009 | Burnett, Jr. et al. |
| 2009/0175821 A1 | 7/2009 | Bridon et al. |
| 2009/0176706 A1 | 7/2009 | Mohapatra |
| 2009/0247462 A1 | 10/2009 | Bogin et al. |
| 2009/0281528 A1 | 11/2009 | Grovender et al. |
| 2009/0286723 A1 | 11/2009 | Levy et al. |
| 2009/0287267 A1 | 11/2009 | Wenzel et al. |
| 2010/0010330 A1 | 1/2010 | Rankers et al. |
| 2010/0028372 A1 | 2/2010 | Jezek |
| 2010/0055150 A1 | 3/2010 | Golembo et al. |
| 2010/0093627 A1 | 4/2010 | Rosen et al. |
| 2010/0204094 A1 | 8/2010 | Simari et al. |
| 2010/0204109 A1 | 8/2010 | Bevec |
| 2010/0216714 A1 | 8/2010 | James et al. |
| 2010/0297021 A1 | 11/2010 | Wendt et al. |
| 2010/0298901 A1 | 11/2010 | Sommer et al. |
| 2011/0034386 A1 | 2/2011 | Vesely |
| 2011/0152194 A1 | 6/2011 | Burnett et al. |
| 2011/0206633 A1 | 8/2011 | Bossard |
| 2011/0282030 A1 | 11/2011 | Dickey et al. |
| 2012/0178689 A1 | 7/2012 | Evans et al. |
| 2012/0220528 A1 | 8/2012 | Van Antwerp et al. |
| 2012/0277155 A1 | 11/2012 | Van Antwerp et al. |
| 2013/0244937 A1 | 9/2013 | Van Antwerp et al. |
| 2013/0274705 A1 | 10/2013 | Burnes |
| 2013/0324472 A1* | 12/2013 | Geimer ............. A61K 38/1709 514/16.4 |
| 2014/0031787 A1 | 1/2014 | Burnes |

FOREIGN PATENT DOCUMENTS

| | | |
|---|---|---|
| EP | 792270 A1 | 9/1997 |
| EP | 1242452 A2 | 9/2002 |
| EP | 1569683 A2 | 9/2005 |
| EP | 1656555 A1 | 5/2006 |
| EP | 1727556 A2 | 12/2006 |
| EP | 1773867 A2 | 4/2007 |
| EP | 1776132 A2 | 4/2007 |
| EP | 1865976 A1 | 12/2007 |
| EP | 1951277 A2 | 8/2008 |
| EP | 2054433 A1 | 5/2009 |
| EP | 2097091 A2 | 9/2009 |
| EP | 2185177 A1 | 5/2010 |
| EP | 2190459 A1 | 6/2010 |
| WO | 01/44284 A2 | 6/2001 |
| WO | 01/70307 A1 | 9/2001 |
| WO | 03/079979 A2 | 10/2003 |
| WO | 2004/030716 A2 | 4/2004 |
| WO | 2004/030717 A2 | 4/2004 |
| WO | 2008/021872 A2 | 2/2008 |
| WO | 2008/031045 A2 | 3/2008 |
| WO | 2008/079995 A2 | 7/2008 |
| WO | 2009/033807 A2 | 3/2009 |
| WO | 2009/040024 A2 | 4/2009 |
| WO | 2009/040031 A2 | 4/2009 |
| WO | 2009/046861 A1 | 4/2009 |
| WO | 2009/149161 A2 | 12/2009 |
| WO | 2010/033217 A1 | 3/2010 |
| WO | 2010/048308 A2 | 4/2010 |
| WO | 2010/063124 A1 | 6/2010 |
| WO | 2010/078325 A2 | 7/2010 |
| WO | 2012/058585 A2 | 5/2012 |
| WO | 2012/115771 A2 | 8/2012 |

(56) References Cited

FOREIGN PATENT DOCUMENTS

| WO | 2013/016148 A2 | 1/2013 |
|---|---|---|
| WO | 2013/019237 A1 | 2/2013 |
| WO | 2013/033675 A1 | 3/2013 |

OTHER PUBLICATIONS

Burton et al., 2009. Hemodialysis-Induced Cardiac Injury: Determinants and Outcomes, Clinical J.A. Society Nephrol., 4:914-920.
Chen H.H., 2000. Subcutaneous Administration of Brain Natriuretic Peptide in Experimental Heart Failure, J. of American College of Cardiology, 36(5):1706-1712, Jun. 19, 2000.
Chung, Eugene S., et al., 2006. "Safety and Tolerability of Serial Home Infusions of Nesiritide for Advanced Heart Failure", Am. J. Cardiol, vol. 97:1370-1373.
Clemens et al. 1998. "Pharmacokinetics and Biological Actions of Subcutaneously Administered Human Brain Natriuretic Peptide", J. Pharm Exp Therap. 287(1):67-71.
Debold et al., 1981. "A Rapid and Potent Natriuretic Response to Intravenous Injection of Atrial Myocardial Extract in Rats," Life Sciences, 28(1):89-94.
Evans, Nile Therapeutics Press Release Oct. 14, 2008.
Jong et al., 2002. "Prognosis and Determinants of Newly Hospitalized for Heart Failure: A Population Based Study", Arch. Intern. Med., 162:1689-1694.
Kozak et al., 2005. National Hospital Discharge Survey: 2002 Annual Summary With Detailed Diagnosis and Procedure Data, Vital Health Stat. 13, 158:1-199.
Lieu, et al., 2009. "Initial Observations of Intravenous CD-NP, Chimeric Natriuetic Peptide, on Renal Functions in Chronic Heart Failure Patients," Journal of Cardiac Failure, 15(6):S77, Aug. 2009.
Lingegowda et al., 2010. "Long-term Outcome of Patients Treated with Prophylactic Mesiritide for the Prevention of Acute Kidney Injury following Cardiovascular Surgery," Clinical Cardiol., 33(4):217-221.
Lisy et al. 2008. Design, Synthesis, and Actions of a Novel Chimeric Natriuretic Peptide: CD-NP, J. American College of Cardiology, 52(1):60-68.
McCullough et al., 2008. "Chronic Kidney Diseases, Prevalence of Premature Cardiovascular Disease, and Relationship to Short-term Mortality," American Heart Journal, 156(2):277-283, Abstract.
Meyer et al., 1998, "Urinary and Plasma Urodilatin Measured by a Direct RIA using a Highly Specific Antiserum," Clinical Chemistry, 44(12):2524-2529.
Perkins et al. 2000. Chapter 21 in Handbook of Pre-Clinical Continuous Intravenous Infusion, ed. Smith and Healing, Taylor and Francis, London.
P0041915.EPN5 PCT/US2012047492 International Preliminary Report on Patentability Jan. 29, 2013.
PCT/US2013/032700, International Search Report, Jul. 15, 2013.
Perkins et al. 2000. Chapter 21 in Handbook of Pre-Clinical Continuous Intravenous Infusion, ed. Smith and Healing, Taylor and Francis, London).
Redfield, et. al, "Restoration of renal response to atrial natriuretic factor in experimental low-output heat failure", Am. J. Physiol., 1989, R917-923:257.
Riter, et al., 2006. "Nonhypotensive Low-Dose Nesiritide has Differential Renal Effects Compared with Standard-Dose Nesiritide in Patients with Acute Decompensated Heart Failure and Renal Dysfunction", Jrnl ACC, vol. 47(11): 2334-2335.
Ronco et al. 2008, "Cardiorenal Syndrome," Journal American College Cardiology, 52:1527-1539, Abstract.
Vesely et al. 1998. "Vessel Dilator Enhances Sodium and Water Excretion and has Beneficial Hemodynamic Effects in Persons with Congestive Heart Failure", Circulation, 98:323-329.
Vesely et al. 2000. "Long-Acting Natriuretic Peptide, Vessle Dilator, and Kaliuretic Peptide Enhance the Urinary Excretion Rate of $^{2}$2-Microglobulin", Metabolism 49:1592-7.
Vesely et al. 2006., "Urodilatin and four cardiac hormones decrease human renal carcinoma cell numbers," European Journal of Clinical Investigation. vol. 36, pp. 810-819. (See figures and p821).
Schirger 2011.Safety Study of Chimeric Natriuretic Peptide(CD-NP) in Stable LVAD Patients (NCT ID:NCT01750905). Published at www.mayo.edu/research/clinical-trials/c1s-20112083.
Search Report of EP application EP11793526.2, mailed Aug. 7, 2013.
International Search Report of PCT/US2012/024203 mailed Nov. 22, 2012.
International Search Report PCT/US2012/047492 mailed Jan. 29, 2013.
International Search Report PCT/US2012/053578, Jan. 29, 2013.
www.mayoclinic.com/health/kidney-failure/DS00682/DSECTION=treatments-and-drugs May 13, 2008, downloaded Oct. 5, 2012.

* cited by examiner

* Statistically significant difference (p<0.05, two-way repeated measures ANOVA; Holm-Sidak post-hoc test).

A

B

A

B

\* P < 0.05 Group Significant from Vehicle Control, Low Salt Diet
\# P < 0.05 Group Significant from Vehicle Control, 4% Salt Diet \* P < 0.05 Group Significant from Vehicle Control, Low Salt Diet
\# P < 0.05 Group Significant from Vehicle Control, 4% Salt Diet

Fig. 30 a- WOCBP only
b- Only applicable for participants with a screening CrCL value of 25-35 mL/min inclusive. To be assessed by MO pre dose for ongoing eligibility
c- Includes urine protein excretion at screening only
d- A spot sample at baseline only. NB An aliquot is to be taken from the entire urine volume at the end of the 0-6hr urine collection interval for assessment of Na⁺, K⁺ and Cr
e- A single aliquot to be taken from the entire urine volume at the end of the 0-6hr urine collection interval and frozen for future potential assessment of KIM1, NGAL and Cystatin-C
f- Not required at screening if performed within 90 days of screening visit
g- To be performed within 1 hour of dose administration but <u>must be prior</u> to cannulation
h- Vitals include non invasive blood pressure (NIBP), pulse, pulse oximetry, temperature, respiratory rate
i- 4 mL of whole blood, collected ambient at each time point
j- Refer to PARC urine collection sampling instructions. Baseline spot urine followed by aliquots of urine to be taken at the end of each interval as specified for each assessment in footnotes
k- One aliquot each for quantification of urine biomarkers, Na⁺, K⁺ and Cr, and VSDL concentrations, as noted above, to be taken from the total urine volume at the end of each urine collection interval
l- 5 mL of whole blood, collected ambient at each time point: 5, 10 and 15 minutes and 1, 2 and 3 hours
m- Spot urine for assessment of renal biomarkers, Na⁺, K⁺ and Cr, and VSDL

|  | Time since start of infusion (Hours/minutes) | | | | | | | | | | | | | | | | | | | +1 week follow up |
|---|---|---|---|---|---|---|---|---|---|---|---|---|---|---|---|---|---|---|---|---|
|  | 6.5 | 7 | 7.5 | 8 | 8.5 | 9 |  |  | 9.5 | 10 | 10.5 | 11 | 12 | 24 |  |  |  |  |  |  |
|  | 380 | 390 | 400 | 420 | 440 | 450 | 460 | 480 | 510 | 540 | 545 | 550 | 555 | 570 | 600 | 630 | 660 | 720 | 1440 |  |
|  | Time since end of infusion (Hours/minutes) | | | | | | | | | | | | | | | | | | | +1 week follow up |
| Assessments | 0.5 | 1 | 1.5 | 2 | 2.5 | 3 |  |  | 3.5 | 4 | 4.5 | 5 | 6 | 18 |  |  |  |  |  |  |
|  | 20 | 30 | 40 | 60 | 80 | 90 | 100 | 120 | 150 | 180 | 185 | 190 | 195 | 210 | 240 | 270 | 300 | 360 | 450 |  |
| Physical Examination |  |  |  |  |  |  |  |  |  |  |  |  |  |  |  |  |  |  |  | X |
| Full Blood Count-FBE |  |  |  |  |  |  |  |  |  |  |  |  |  |  |  |  |  |  | X | X |
| Biochemistry (MBA 20) |  |  |  |  |  |  |  |  |  |  |  |  |  |  |  |  |  |  | X | X |
| Plasma NT-Pro BNP |  |  |  |  |  |  |  |  |  |  |  |  |  |  |  |  |  |  | X | X |
| CK-MB |  |  |  |  |  |  |  |  |  |  |  |  |  |  |  |  |  |  | X | X |
| Troponin |  |  |  |  |  |  |  |  |  |  |  |  |  |  |  |  |  |  | X | X |
| Urinalysis[a] |  |  |  |  |  |  |  |  |  |  |  |  |  |  |  |  |  |  | X | X |
| Urine Na$^+$,K$^+$,Cr,[b] |  |  |  |  |  |  |  |  |  |  |  |  |  |  |  |  |  | X | X |  |
| Urine Biomarkers[c] |  |  |  |  |  |  |  |  |  |  |  |  |  |  |  |  |  | X | X | X |
| Cardiac Imaging |  |  |  |  |  |  |  |  |  |  |  |  |  |  |  |  |  |  | X |  |
| ECG |  |  |  |  |  |  |  |  |  |  |  |  |  |  |  |  |  |  | X | X |
| NICOM |  | X | X | X | X | X |  |  |  | X |  | X | X | X |  |  |  |  |  |  |
| Vitals[d] |  | X | X | X | X | X |  |  |  | X |  | X | X | X |  |  |  |  |  | X |
| AE monitoring | X | X |  | X | X | X |  |  |  | X | X | X | X | X |  |  |  |  |  | X |
| PK Sampling VSDL[e] | X |  | X | X | X |  | X | X | X |  |  |  |  | X | X | X | X |  | X |  |
| Urine collection [f] |  |  |  |  |  |  | 6-12 | | | | | | | | | | | | 12-24 |  | a- Includes urine protein excretion at screening only
b- A single aliquot to be taken from the entire urine volume at the end of 6-12hr and 12-24hr urine collection intervals for assessment of Na$^+$, K$^+$ and Cr
c- A single aliquot to be taken from the entire urine volume at the end of 6-12hr and 12-24hr urine collection interval and frozen for future potential assessment of KIM1, NGAL and Cystatin-C
d- Vitals include, non invasive blood pressure, pulse, pulse oximetry, temperature, respiratory rate
e- 4 mL of whole blood, collected ambient at each time point
f- Refer to PARC urine collection sampling instructions. Urine collection intervals as specified. Aliquots of urine to be taken at the end of each interval as specified for each assessment (biomarkers, Na$^+$, K$^+$ and Cr, and VSDL, in footnotes

Fig. 31

SEQUENCE LISTING

```
<160> NUMBER OF SEQ ID NOS: 6

<210> SEQ ID NO 1
<211> LENGTH: 30
<212> TYPE: PRT
<213> ORGANISM: Homo sapiens
<220> FEATURE:
<223> OTHER INFORMATION: human long acting natriuretic peptide (LANP),
      proANP, ANP prohormone a.a. 1-30

<400> SEQUENCE: 1

Asn Pro Met Tyr Asn Ala Val Ser Asn Ala Asp Leu Met Asp Phe Lys
 1               5                  10                  15

Asn Leu Leu Asp His Leu Glu Glu Lys Met Pro Leu Glu Asp
            20                  25                  30

<210> SEQ ID NO 2
<211> LENGTH: 37
<212> TYPE: PRT
<213> ORGANISM: Homo sapiens
<220> FEATURE:
<223> OTHER INFORMATION: human vessel dilator (VD) peptide, ANP
      prohormone a.a. 31-67

<400> SEQUENCE: 2

Glu Val Val Pro Pro Gln Val Leu Ser Glu Pro Asn Glu Glu Ala Gly
 1               5                  10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 3
<211> LENGTH: 20
<212> TYPE: PRT
<213> ORGANISM: Homo sapiens
<220> FEATURE:
<223> OTHER INFORMATION: human kaliuretic peptide (KP), ANP prohormone
      a.a. 79-98

<400> SEQUENCE: 3
```

-continued

```
Ser Ser Asp Arg Ser Ala Leu Leu Lys Ser Lys Leu Arg Ala Leu Leu
1               5                   10                  15

Thr Ala Pro Arg
            20

<210> SEQ ID NO 4
<211> LENGTH: 28
<212> TYPE: PRT
<213> ORGANISM: Homo sapiens
<220> FEATURE:
<223> OTHER INFORMATION: human atrial natriuretic peptide (ANP), ANP
      prohormone a.a. 99-126

<400> SEQUENCE: 4

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 5
<211> LENGTH: 32
<212> TYPE: PRT
<213> ORGANISM: Homo sapiens
<220> FEATURE:
<223> OTHER INFORMATION: human urodilatin (URO), ANP prohormone a.a.
      95-126

<400> SEQUENCE: 5

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 6
<211> LENGTH: 32
<212> TYPE: PRT
<213> ORGANISM: Homo sapiens
<220> FEATURE:
<223> OTHER INFORMATION: human brain natriuretic peptide (BNP)

<400> SEQUENCE: 6

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

THERAPY FOR KIDNEY DISEASE AND/OR HEART FAILURE

REFERENCE TO A "SEQUENCE LISTING," A TABLE, OR A COMPUTER

PROGRAM LISTING APPENDIX SUBMITTED AS AN ASCII TEXT FILE

The Sequence Listing written in file 97446-926034.TXT, created on Jan, 7, 2015, 4,096 bytes, machine format IBM-PC, MS-Windows operating system, is hereby incorporated by reference in its entirety for all purposes.

FIELD OF THE INVENTION

The invention relates to therapies involving the administration of a natriuretic peptide for the treatment of pathological conditions such as kidney disease alone, heart failure alone, or kidney disease with concomitant heart failure. The systems and methods of the invention can increase and/or control in vivo levels of natriuretic peptide in the plasma or serum of the subject to optimize the outcome of a therapeutic regimen(s). The invention further relates to the field of chronic and acute delivery of a drug through routes of administration including but not limited to subcutaneous, intravascular, intraperitoneal and direct to organ. A preferred route is subcutaneous administration. The methods of delivery contemplated by the invention include, but are not limited to, implanted and external pumps at programmed or fixed rates, implanted or percutaneous vascular access ports, depot injection, direct delivery catheter systems, and local controlled release technology.

BACKGROUND

Kidney disease (KD), also known as renal disease, is a progressive loss in renal function over a period of months or years. In particular, Kidney Disease (KD) is a major U.S. public health concern with recent estimates suggesting that more than 26 million adults in the U.S. have the disease including chronic kidney disease (CKD). The primary causes of KD are diabetes and high blood pressure, which are responsible for up to two-thirds of the cases. In recent years, the prevalence of KD has increased due to a rising incidence of diabetes mellitus, hypertension (high blood pressure) and obesity, and also due to an aging population. Because KD is co-morbid with cardiovascular disease, heart failure is a closely related health problem. In the case of Chronic Kidney Disease (CKD), patients have an increased risk of death from cardiovascular events because CKD is thought to accelerate the development of heart disease (McCullough et al., Chronic kidney diseases, prevalence of premature cardiovascular disease, and relationship to short-term mortality, Am. Heart J., 2008; 156:277-283). CKD patients generally have cardiac-specific mortality rates many times higher than age- and sex-matched non-CKD populations, and it has been suggested that the pathological heart-kidney interactions are bidirectional in nature (Ronco C. et al., Cardiorenal syndrome, J. Am. Coll. Cardiol. 2008; 52:1527-39). Ina recently proposed classification system for Cardio-Renal Syndrome (CRS), Type II Cardio-Renal Syndrome (CRS) is expressly defined as constituting chronic abnormalities in cardiac function (e.g., chronic congestive heart failure) that simultaneously causes progressive and permanent kidney disease. Similarly, Type IV CRS is defined under the same classification scheme as being a type of kidney disease that contributes to decreased cardiac function, cardiac hypertrophy and/or increased risk of adverse cardiovascular events.

Heart failure (HF) is a condition in which the heart's ability to pump blood through the body is impaired. HF includes, but is not limited to, acute heart failure, chronic heart failure, and acute decompensated (ADHF). HF is a common condition that affects approximately 5 million people in the United States, with 550,000 new cases diagnosed each year. Symptoms of HF include swelling and fluid build-up in the legs, feet, and/or lungs; shortness of breath; coughing; elevated heart rate; change in appetite; and fatigue. If left untreated, compensated HF can deteriorate to a point where a person undergoes ADHF, which is the functional deterioration of HF. ADHF is a major clinical challenge because HF as a primary discharge diagnosis accounts for over 1 million hospital discharges and over 6.5 million hospital days (Kozak et al., National Hospital Discharge Survey: 2002 annual summary with detailed diagnosis and procedure data, Vital Health Stat. 13, 2005; 158:1-199). The financial burden due to HF is largely borne by public health resources (e.g., Medicare and Medicaid) wherein the 6 month readmission rate is 50%, the short-term mortality rate (i.e., 60-90 days) is around 10%, and the 1 year mortality risk is around 30% (Jong et al., Prognosis and determinants of survival in patients newly hospitalized for heart failure: a population based study, Arch. Intern. Med. 2002; 162:1689-94). Recently, the number of hospitalizations attributed to ADHF has risen significantly where many people are readmitted soon after discharge because of recurring symptoms or further medical complications. Current ADHF treatments focus on removing excess fluid buildup by increasing urination with diuretic medications or by draining fluid directly from the veins via ultrafiltration. ADHF can also be treated using vasodilators, inotropes, and other therapeutic regimens described herein and as known within the art. However, recent data suggests that dialysis in patients with end stage renal disease (ESRD) may precipitate ADHF (Burton et al., Hemodialysis-induced cardiac injury: determinants and outcomes, Clin. J. Am. Soc. Nephrol. 2009; 4:914-920).

One pharmaceutical approach to treat HF is the use of Nesiritide (B-type natriuretic peptide), which is an FDA approved therapeutic option that lowers elevated filing pressures and improves dyspnea. Nesiritide is the recombinant form of the 32 amino acid human B-type natriuretic peptide, which is normally produced by the ventricular myocardium. The drug facilitates cardiovascular fluid homeostasis through counter-regulation of the renin-angiotensin-aldosterone system and promotion of vasodilation, natriuresis, and diuresis. Nesiritide is administered intravenously usually by bolus injection, followed by IV infusion. Another approved atrial natriuretic type peptide is human recombinant atrial natriuretic peptide (ANP), Carperitide, which has been approved for the clinical management of ADHF in Japan since 1995, is also administered via intravenous infusion. Another peptide under study is human recombinant urodilatin (URO), Ularitide.

In the case of Nesiritide, one recent large study suggested that Nesiritide is ineffective in treating severe heart failure (Lingegowda et al., Long-term outcome of patients treated with prophylactic Nesiritide for the prevention of acute kidney injury following cardiovascular surgery, Clin. Cardiol. 2010; 33(4):217-221). The study concluded that the reno-protection provided by Nesiritide in the immediate postoperative period was not associated with improved long-term survival in patients undergoing high-risk cardiovascular surgery.

One obstacle to delivering peptides in a clinically effective manner is that peptides generally have poor delivery properties due to the presence of endogenous proteolytic enzymes, which are able to quickly metabolize many peptides at most routes of administration. In addition, peptides and proteins are generally hydrophilic do not readily penetrate lipophilic biomembranes, and have short biological half-lives due to rapid metabolism and clearance. These factors are significant deterrents to the effective and efficient use of most protein drug therapies. Although a peptide drug can be administered intravenously, this route of administration can potentially cause undesirable effects because the peptide drug is directly introduced into the bloodstream. Intramuscular (IM) administration may be considered where sustained action is preferred. However, IM administration could result in slow absorption and possible degradation of the peptide at the injection site. Subcutaneous (SQ) injection can provide a slower absorption rate compared to IM administration and might be useful for long term therapy. However, potency could be decreased via SQ administration due to degradation and poor absorption.

Hence, there is an unmet need for drug delivery systems and device-mediated methods of protein delivery that can offer significant advantages over conventional delivery systems by providing increased efficiency, improved performance, patient compliance and convenience. There is also a need for clinically effective therapies for delivering and treating KD alone or with concomitant HF. In the field of both chronic and acute delivery of peptides, there is an unmet need for maintaining the therapeutic effect of an atrial natriuretic peptide for a desired period of time and at a specific plasma concentration. There is also need for continuous infusion of a natriuretic peptide as an effective alternative to administration by multiple injections. There is a need for developing the pharmacokinetic and pharmacodynamic profile for ANP drugs useful for treating KD and HF. There is also an unmet need for developing therapies providing for improved efficacy of the delivered peptides using parenteral dosage forms such as intravenous, intramuscular, and subcutaneous injection or infusion.

Many studies have shown that known KD and HF therapies are associated with mortality in patients with heart failure. Hence, there is an unmet need for developing new agents and methods of delivery to safely and effectively improve cardiac performance and modulate fluid load. There is also an unmet need for methods that open new pathways to improve quality of life and outcomes of patients with acute and worsening decompensated heart failure and KD.

SUMMARY OF THE INVENTION

The disclosure provided herein is directed to a study of continuous subcutaneous (SQ) administration of Atrial Natriuretic Peptide (ANP) hormones such as vessel dilator (VD) kaliuretic peptide (KP), and brain natriuretic peptide, generally referred to herein as "natriuretic peptides," to patients having Kidney Disease (KD) alone, Heart Failure (HF) alone, or KD with concomitant HF. The continuous subcutaneous administration of a natriuretic peptide can be used to maintain in vivo concentrations of the natriuretic peptide above a critical efficacy threshold for an extended period of time. Both bolus and continuous SQ delivery of natriuretic peptides are contemplated. The invention disclosed herein has a number of embodiments that relate to therapeutic regimens and systems for treatment of KD alone, HF alone or KD with concomitant HF. In certain embodiments, a medical system or method is used to treat a subject having cardiorenal syndrome (CRS).

In certain embodiments, a medical system or method is used to treat a subject having heart disease.

In certain embodiments, a medical system or method is used to treat a subject having kidney disease.

In certain embodiments, a medical system or method is used to treat a subject having cardiorenal syndrome (CRS) selected from CRS Type I, CRS Type II, CRS Type III, CRS Type IV or CRS Type V.

In certain embodiments, a medical system or method is used to treat a subject having heart disease selected from chronic heart failure, congestive heart failure, acute heart failure; decompensated heart failure, systolic heart failure, or diastolic heart failure.

In certain embodiments, a medical system or method is used to treat a subject having kidney disease selected from Stage 1 kidney disease, Stage 2 kidney disease, Stage 3 kidney disease, Stage 4 kidney disease, Stage 5 kidney disease, and end-stage renal disease.

The systems and methods of the invention are directed to the administration of a natriuretic peptide to a subject for the treatment of KD alone, HF alone, or KD with concomitant HF. The systems and methods of the invention are also useful for treating other renal or cardiovascular diseases, such as congestive heart failure (CHF), dyspnea, elevated pulmonary capillary wedge pressure, chronic renal insufficiency, acute renal failure, cardiorenal syndrome, and diabetes mellitus. The medical system of the invention can contain a drug provisioning component to administer a therapeutically effective amount of natriuretic peptide to a subject suffering from KD alone, HF alone, or KD with concomitant HF, wherein the drug provisioning component maintains a plasma concentration of the natriuretic peptide within a specified range. The medical system can administer the natriuretic peptide subcutaneously, intramuscularly, or intravenously. The medical system delivers an ANP hormone selected from any one of long-acting natriuretic peptide (LANP), kaliuretic peptide (KP), urodilatin (URO), atrial natriuretic peptide (ANP) and vessel dilator (VD) and also brain natriuretic peptide (BNP). Further, the medical system can maintain a plasma concentration of the natriuretic peptide reached during either a subcutaneous bolus of the natriuretic peptides at 6000 ng/kg or a 1 hour intravenous infusion of the natriuretic peptides at 100 ng/kg·min in the subject. The medical system can also maintain a plasma concentration of the natriuretic peptide reached during either a subcutaneous bolus of the natriuretic peptides at 18,000 ng/kg or a 1 hour intravenous infusion of the natriuretic peptides at 300 ng/kg·min in the subject. In any embodiment, a therapeutically effective amount of the natriuretic peptide is based at least in part on a volume of distribution for the natriuretic peptide exhibited by the subject. In any embodiment, the volume of distribution for the natriuretic peptide is in the range represented by n to (n+i) liters, where n={x∈ℝ |5≤x≤65} and i={y∈ℝ |0≤y≤(65−n)}. In another embodiment, the volume of distribution for the natriuretic peptide is from any one of about 5 to about 65 L, about 10 to about 25 L, about 5 to about 15 L, about 30 to about 65 L and about 45 to about 65 L.

A method for administering a natriuretic peptide such as VD and KP to a subject having KD alone, HF alone, or KD with concomitant HF is provided. The method comprises administering a natriuretic peptide to a subject using a drug provisioning apparatus to maintain a plasma level of the natriuretic peptide in the subject within a specified mean steady state concentration range. This specified concentration is not greater than a plasma level reached by either a single subcutaneous bolus injection of the natriuretic peptide at 6000 ng of the natriuretic peptide per kilogram of the subject's body weight or a plasma level reached by a one hour intravenous infusion of the natriuretic peptide at 100 ng of the natriuretic peptide per kilogram·minute of the subject's body weight. The specified concentration can also not be greater than a plasma level reached by either a single subcutaneous bolus injection of the natriuretic peptide at 18,000 ng of the natriuretic peptide per kilogram of the subject's body weight or a plasma level reached by a one hour intravenous infusion of the natriuretic peptide at 300 ng of the natriuretic peptide per kilogram·minute of the subject's body weight. The method can administer the natriuretic peptide subcutaneously, intramuscularly, or intravenously. One route is subcutaneous administration. The method delivers the ANP hormones selected from any one of long-acting natriuretic peptide (LANP), kaliuretic peptide (KP), urodilatin (URO), atrial natriuretic peptide (ANP) and vessel dilator (VD), and also brain natriuretic peptide (BNP).

A therapeutic method for treatment of KD alone, HF alone, or KD with concomitant HF is provided is provided. The therapy is based on a method of treatment that effects increased levels of natriuretic peptide. The method includes increasing plasma levels of a natriuretic peptide in a subject having KD alone, HF alone, or KD with concomitant HF is provided by causing the selective release of the natriuretic peptide using a drug provisioning component. The method further includes a control unit consisting of a processor being operably connected to and in communication with the drug provisioning component, wherein the control unit contains a set of instructions that causes the drug provisioning component to administer the natriuretic peptide to the subject according to a therapeutic regimen. The therapeutic regimen is tailored so that the plasma concentration of the natriuretic peptide is maintained within a specified range by effecting controlled administration of the natriuretic peptide using the drug provisioning component. This specified concentration is not greater than a plasma level reached by either a single subcutaneous bolus injection of the natriuretic peptide at 6000 ng of the natriuretic peptide per kilogram of the subject's body weight or a level reached by a one hour intravenous infusion of the natriuretic peptide at 100 ng of the natriuretic peptide per kilogram·minute of the subject's body weight. This specified concentration can also not be greater than a plasma level reached by either a single subcutaneous bolus injection of the natriuretic peptide at 18,000 ng of the natriuretic peptide per kilogram of the subject's body weight or a level reached by a one hour intravenous infusion of the natriuretic peptide at 300 ng of the natriuretic peptide per kilogram·minute of the subject's body weight.

A second therapeutic method of treating a subject having KD alone, HF alone, or KD with concomitant HF is provided, wherein the method includes increasing plasma or serum concentration of the natriuretic peptide in the subject using the systems of the invention. The method further includes maintaining circulating levels of natriuretic peptide in the plasma or serum of the subject within a specified mean steady state concentration range. In any embodiment, the specified mean steady state concentration is not greater than a plasma level reached by either a single subcutaneous bolus injection of the natriuretic peptide at 6000 ng of the natriuretic peptide per kilogram of the subject's body weight or a plasma level reached by a one hour intravenous infusion of the natriuretic peptide at 100 ng of the natriuretic peptide per kilogram·minute of the subject's body weight. In any embodiment, the specified mean steady state concentration is not greater than a plasma level reached by either a single subcutaneous bolus injection of the natriuretic peptide at 18,000 ng of the natriuretic peptide per kilogram of the subject's body weight or a plasma level reached by a one hour intravenous infusion of the natriuretic peptide at 300 ng of the natriuretic peptide per kilogram·minute of the subject's body weight.

In any embodiment, the method may further include monitoring one or more physiologic parameters of the subject. In any embodiment, the method further includes creating a subject-specific dose-response database using data collected from the subject, evaluating the data in the database, calculating instructions for use with a drug delivery device to maintain a plasma level of the natriuretic peptide in the subject within a specified mean steady state concentration range, and further monitoring subject data and updating the database as necessary. Data collected from the subject could include subject weight, enzyme levels, biomarkers, observed drug clearance, etc.

A medical system for administering the natriuretic peptide to a subject having KD alone, HF alone, or KD with concomitant HF is provided. The medical system includes a drug provisioning component that selectively releases a pharmaceutically effective amount of natriuretic peptide to the subject and a control unit consisting of a processor operably connected to and in communication with the drug provisioning component. The control unit is programmed with a set of instructions that causes the drug provisioning component to administer the natriuretic peptide to the subject according to a therapeutic regimen comprising administering a natriuretic peptide to the subject subcutaneously, wherein the therapeutic regimen is sufficient to maintain circulating levels of the natriuretic peptide in the plasma or serum of the subject above a desired mean steady state concentration. In any embodiment, the therapeutic regime is selected to maintain serum natriuretic peptide concentrations in the subject at a value not greater than a critical concentration threshold. The critical concentration can be either the plasma level reached by either a single subcutaneous bolus injection of the natriuretic peptide at 6000 ng of the natriuretic peptide per kilogram of the subject's body weight or the plasma level reached by a one hour intravenous infusion of the natriuretic peptide at 100 ng of the natriuretic peptide per kilogram·minute of the subject's body weight. The critical concentration can also be either the plasma level reached by either a single subcutaneous bolus injection of the natriuretic peptide at 18,000 ng of the natriuretic peptide per kilogram of the subject's body weight or the plasma level reached by a one hour intravenous infusion of the natriuretic peptide at 300 ng of the natriuretic peptide per kilogram·minute of the subject's body weight.

In any embodiment of the invention, the natriuretic peptides may include any of the atrial natriuretic peptide (ANP) hormones and brain natriuretic peptide (BNP). ANP hormones include long acting natriuretic peptide (LANP), kaliuretic peptide (KP), atrial natriuretic peptide (ANP), vessel dilator (VD), and urodilatin (URO).

In any embodiment of the invention, the drug provisioning component of the medical system may administer the natriuretic peptide to the subject subcutaneously, intramuscularly, or intravenously. A preferred route is subcutaneous administration.

In any embodiment of the invention, a drug provisioning component may consist of any of the following elements: an external or implantable drug delivery pump, an implanted or percutaneous vascular access port, a direct delivery catheter system, and a local drug-release device. In any embodiment of the invention, the drug provisioning component can deliver the natriuretic peptide at a fixed, pulsed, or variable rate. The drug provisioning component may also be programmable or controllable by a patient who is a subject of the invention.

In any embodiment of the invention, sensors of the medical system of the invention may monitor one or more physiological parameters of the subject obtained by a sensor. These parameters are preferably related to blood pressure or the renal system and can include blood pressure, pulmonary artery pressure, left atrial pressure, right atrial pressure, central venous pressure, lung fluid volume, proteinuria, plasma renin, cardiac output, and glomerular filtration rate.

In any embodiment of the invention, a control unit may operate to regulate the selective release of the natriuretic peptide to maintain a mean steady state concentration using data obtained from the subject. The control unit may further contain computer memory, and the control unit, using the computer memory and processor, may further compile and store a database containing data collected from the subject and also compute a dosing schedule that makes up a part of the therapeutic regimen.

In any embodiment, a medical system is provided for administering a natriuretic peptide. The medical system has a drug provisioning component to administer a therapeutically effective amount of a natriuretic peptide to a subject suffering from kidney disease alone, heart failure alone, or kidney disease with concomitant heart failure, said drug provisioning component maintaining an effective plasma concentration of the natriuretic peptide based, at least in part, on a volume of distribution for the natriuretic peptide exhibited by the subject.

In any embodiment, a method for administering a natriuretic peptide is provided. A natriuretic peptide is administered to a subject suffering from kidney disease alone, heart failure, or with concomitant kidney disease and heart failure using a drug provisioning component to maintain a plasma level of the natriuretic peptide at a steady state concentration from about 0.5 to about 60 ng/mL or about 0.5 to about 40 ng/mL, wherein the natriuretic peptide is administered through a subcutaneous route. The concentration levels for the natriuretic peptide can also be in the range from greater than 0 to 40 ng/ml, as represented by the range from n to (n+i), where n=$\{x \in \mathbb{R} \mid 0 < x \leq 40\}$ and i=$\{y \in \mathbb{R} \mid 0 \leq y \leq (40-n)\}$. The concentration levels for the natriuretic peptide can also be in the range from greater than 0 to 60 ng/ml, as represented by the range from n to (n+i), where n=$\{x \in \mathbb{R} \mid 0 < x \leq 60\}$ and i=$\{y \in \mathbb{R} \mid 0 \leq y \leq (60-n)\}$.

In any embodiment, a method for administering a natriuretic peptide is provided. The natriuretic peptide is administered to a subject using a drug provisioning component to maintain a plasma level of the natriuretic peptide at a steady state concentration from about 0.5 to about 40 ng/mL or from about 0.5 to about 60 ng/mL, wherein the natriuretic peptide is administered through a subcutaneous route.

In any embodiment, a method for administering a natriuretic peptide is provided. The natriuretic peptide is administered to a subject suffering from kidney disease alone, heart failure alone, or with concomitant kidney disease and heart failure using a drug provisioning component based at least in part on a volume of distribution for the natriuretic peptide exhibited by the subject.

In any embodiment of the invention, a specified range of plasma concentration of the natriuretic peptide is not greater than a plasma concentration of the natriuretic peptide reached during either a subcutaneous bolus of the natriuretic peptide at 6000 ng/kg or a 1 hour intravenous infusion of the natriuretic peptide at 100 ng/kg·min in the subject.

In any embodiment of the invention, a specified range of plasma concentration of the natriuretic peptide range is not greater than a plasma concentration of the natriuretic peptide reached during either a subcutaneous bolus of the natriuretic peptide at 18,000 ng/kg or a 1 hour intravenous infusion of the natriuretic peptide at 300 ng/kg·min in the subject.

In any embodiment of the invention, a drug provisioning component delivers a therapeutically effective amount of the natriuretic peptide in a cyclic on/off pattern at a rate (ng/kg of body weight) for multiple days, wherein the rate results in a plasma concentration of natriuretic peptide not greater than a plasma concentration of the natriuretic peptide reached in the subject during either a subcutaneous bolus at 6000 ng/kg or a 1 hour intravenous infusion of the natriuretic peptide at 100 ng/kg·min.

In any embodiment of the invention, a drug provisioning component delivers a therapeutically effective amount of the natriuretic peptide in a cyclic on/off pattern at a rate (ng/kg of body weight) for multiple days, wherein the rate results in a plasma concentration of natriuretic peptide not greater than a plasma concentration of the natriuretic peptide reached in the subject during either a subcutaneous bolus at 18,000 ng/kg or a 1 hour intravenous infusion of the natriuretic peptide at 300 ng/kg·min.

In any embodiment of the invention, a drug provisioning component delivers a therapeutically effective amount of the natriuretic peptide at a rate (ng/kg of body weight) for 4 hours on and 8 hours off, then 4 hours on and 8 hours off for each of 3 days, wherein the rate results in a plasma concentration of natriuretic peptide not greater than a plasma concentration of the natriuretic peptide reached in the subject during either a subcutaneous bolus at 6000 ng/kg or a 1 hour intravenous infusion of the natriuretic peptide at 100 ng/kg·min.

In any embodiment of the invention, a drug provisioning component delivers a therapeutically effective amount of the natriuretic peptide at a rate (ng/kg of body weight) for 4 hours on and 8 hours off, then 4 hours on and 8 hours off for each of 3 days, wherein the rate results in a plasma concentration of natriuretic peptide not greater than a plasma concentration of the natriuretic peptide reached in the subject during either a subcutaneous bolus at 18,000 ng/kg or a 1 hour.

In any embodiment of the invention, a drug provisioning component delivers a therapeutically effective amount of the natriuretic peptide to maintain a plasma level of the natriuretic peptide at a steady state concentration from any one of about 0.5 to about 60 ng/mL, about 0.5 to about 40 ng/mL, about 10 to about 60 ng/mL, about 20 to about 40 ng/mL, about 30 to about 60 ng/mL, about 15 to about 55 ng/mL, about 25 to about 55 ng/mL about 35 to about 55 ng/mL about 23 to about 42 ng/mL about 19 to about 43 ng/mL about 10 to about 50 ng/mL 10 to about 20 ng/mL, about 20 to about 30 ng/mL, about 20 to about 35 ng/mL, about 25 to about 40 ng/mL, and about 30 to about 40 ng/mL.

In any embodiment of the invention, a drug provisioning component delivers a therapeutically effective amount of the natriuretic peptide to maintain a plasma level of the natriuretic peptide (ng/mL) at a steady state concentration in the range represented by n to (n+i), where n={x∈R|0<x≤60} and i={y∈R|0≤y≤(60−n)}.

In any embodiment of the invention, a drug provisioning component delivers a therapeutically effective amount of the natriuretic peptide to maintain a plasma level of the natriuretic peptide (ng/mL) at a steady state concentration in the range represented by n to (n+i), where n={x∈R|0<x≤40} and i={y∈R|0≤y≤(40−n)}.

In any embodiment of the invention, a drug provisioning component delivers a therapeutically effective amount of the natriuretic peptide at a continuous rate (ng/kg of body weight) matching the area under the curve of a subcutaneous bolus at 18,000 ng/kg of the subject.

In any embodiment of the invention, wherein a medical system contains a control unit in communication with the drug provisioning component.

In any embodiment of the invention, a drug provisioning component is selected from an external or implantable drug delivery pump, an implanted or percutaneous vascular access port, a direct delivery catheter system, and a local drug-release device.

In any embodiment of the invention, a drug provisioning component is programmable.

In any embodiment of the invention, a drug provisioning component is controlled by a patient who is the subject.

In any embodiment of the invention, a medical system has a control unit having a processor and memory wherein the processor compiles and stores a database of data collected from the subject using a sensor and computes a dosing schedule.

In any embodiment of the invention, data collected from the subject is transmitted via radio frequency by a transmitter, and the data is received by an external controller.

In any embodiment of the invention, data collected from the subject is transmitted and digital instructions returned to the control unit via the Internet.

In any embodiment of the invention, a drug provisioning component and a control unit are co-located.

In any embodiment of the invention, a drug provisioning component, or the control unit are connected or controlled wirelessly.

In any embodiment of the invention, a drug provisioning component is programmed to release a single bolus of 6000 ng of natriuretic peptide per kilogram of the subject's body weight wherein the single bolus is administered three times at 0 hours, 24 hours and 48 hours.

In any embodiment of the invention, a drug provisioning component is programmed to continuously deliver 18,000 ng of natriuretic peptide per kilogram of the subject's body weight over 72 hours.

In any embodiment of the invention, a medical system has a patch pump in communication with a control unit.

In any embodiment of the invention, a specified range of a plasma concentration of the natriuretic peptide is not greater than a plasma concentration of the natriuretic peptide reached during either a subcutaneous bolus of the natriuretic peptide at 18,000 ng/kg or a 1 hour intravenous infusion of the natriuretic peptide at 300 ng/kg·min in the subject.

In any embodiment of the invention, a drug provisioning component subcutaneously delivers a therapeutically effective amount of the natriuretic peptide at a rate (ng/kg of body weight) for 4 hours on and 8 hours off, then 4 hours on and 8 hours off for each of 3 days, wherein the rate results in a plasma concentration of natriuretic peptide not greater than a plasma concentration of the natriuretic peptide reached in the subject during either a subcutaneous bolus at 6000 ng/kg or a 1 hour intravenous infusion of the natriuretic peptide at 100 ng/kg·min.

In any embodiment, a method for administering a natriuretic peptide has the step of compiling and storing data collected from the subject using a processor and memory, and computing a dosing schedule.

In any embodiment, a method for administering a natriuretic peptide has the step of adjusting a dosing schedule to meet pharmacokinetic variables calculated from one or more subject parameters, wherein the subject parameters include any one of blood pressure, pulmonary artery pressure, left atrial pressure, right arterial pressure, central venous pressure, lung fluid volume, proteinuria, plasma renin, cardiac output, and glomerular filtration rate.

In any embodiment, a method for administering a natriuretic peptide has the step of collecting data from the subject and transmitting the data via radio frequency to an external controller.

In any embodiment, a method for administering a natriuretic peptide has the step of collecting and transmitting data from the subject and returning digital instructions to a control unit via the Internet.

In any embodiment, a method for administering a natriuretic peptide uses a drug provisioning component, and a control unit that are connected or controlled wirelessly.

In any embodiment, a method for administering a natriuretic peptide uses a drug provisioning component programmed to release a single bolus of 6000 ng of natriuretic peptide per kilogram of the subject's body weight.

In any embodiment, a method for administering a natriuretic peptide uses a drug provisioning component programmed to release a single bolus of 18,000 ng of natriuretic peptide per kilogram of the subject's body weight.

In any embodiment, a method for administering a natriuretic peptide uses a single bolus repeated three times.

In any embodiment, a method for administering a natriuretic peptide uses a drug provisioning component programmed to continuously deliver 6,000 ng of natriuretic peptide per kilogram of the subject's body weight.

In any embodiment, a method for administering a natriuretic peptide uses a drug provisioning component programmed to continuously deliver 18,000 ng of natriuretic peptide per kilogram of the subject's body weight.

In any embodiment, a method for administering a natriuretic peptide has the step of using a patch pump in communication with a control unit.

In any embodiment, a method for administering a natriuretic peptide maintains a plasma concentration of the natriuretic peptide at a steady state concentration at a specified range from about 0.5 to about 40 ng/mL.

In any embodiment, a method for administering a natriuretic peptide maintains a plasma concentration of the natriuretic peptide at a steady state concentration in a specified range represented by n to (n+i), where n={x∈ R |0<x≤60} and i={y∈R |0≤y≤(60−n)}.

In any embodiment, a method for administering a natriuretic peptide maintains a plasma concentration of the natriuretic peptide at a steady state concentration in a specified range represented by n to (n+i), where n={x∈ R |0<x≤40} and i={y∈R |0≤y≤(40−n)}.

In any embodiment, a method for administering a natriuretic peptide maintains a plasma concentration of the natriuretic peptide at a steady state concentration at a specified range at any one of about 10 to 60 ng/mL, about 10 to about 20 ng/mL, about 20 to about 30 ng/mL, about 20 to about 35 ng/mL, about 25 to about 40 ng/mL, and about 30 to about 40 ng/mL.

In any embodiment, a method for administering a natriuretic peptide is performed on a subject exhibiting a subcutaneous adsorption half-life for the natriuretic peptide from any one of about 0 to about 60 minutes, 0 to about 5 minutes, 15 to about 25 minutes, 0 to about 30 minutes, and 15 to about 30 minutes.

In any embodiment, a method for administering a natriuretic peptide is performed on a subject exhibiting a subcutaneous adsorption half-life for the natriuretic peptide of about 20 minutes.

In any embodiment, a method for administering a natriuretic peptide is performed, wherein the natriuretic peptide is administered to a subject at a rate from any one of about 10 to about 300 ng/kg·min, about 10 to about 150 ng/kg·min, about 25 to about 145 ng/kg·min, about 30 to about 140 ng/kg·min, about 35 to about 125 ng/kg·min, about 50 to about 120 ng/kg·min, about 65 to about 115 ng/kg·min, and about 85 to about 110 ng/kg·min of the subject's body weight.

In any embodiment, a method for administering a natriuretic peptide is performed wherein from about 0.6 to about 9 µg of the natriuretic peptide is administered to the subject per kg of the subject's body weight in an hour time period.

In any embodiment, a method for administering a natriuretic peptide is performed wherein the natriuretic peptide is administered to a subject at a rate from any one of about 1 to about 8 µg, about 2 to about 5 µg, about 3 to about 4 µg, about 1 to about 7 µg, about 3 to about 5 µg, about 2 to about 6 µg, about 7 to about 9 µg, and about 8 to about 9 µg of the natriuretic peptide is administered to the subject per kg of the subject's body weight in an hour time period.

In any embodiment, a method for administering a natriuretic peptide is performed wherein the natriuretic peptide is vessel dilator (VD).

In any embodiment of the invention, a drug provisioning component delivers a therapeutically effective amount of the natriuretic peptide at a continuous rate (ng/kg of body weight) matching the area under the curve of a subcutaneous bolus at 6000 ng/kg of the subject.

In any embodiment of the invention, a drug provisioning component delivers a therapeutically effective amount of the natriuretic peptide to maintain a plasma level of the natriuretic peptide at a steady state concentration from any one of about 0.5 to about 60 ng/mL, about 0.5 to about 40 ng/mL, about 10 to about 60 ng/mL, about 20 to about 40 ng/mL, about 30 to about 60 ng/mL, about 15 to about 55 ng/mL, about 25 to about 55 ng/mL about 35 to about 55 ng/mL about 23 to about 42 ng/mL about 19 to about 43 ng/mL about 10 to about 50 ng/mL 10 to about 20 ng/mL, about 20 to about 30 ng/mL, about 20 to about 35 ng/mL, about 25 to about 40 ng/mL, and about 30 to about 40 ng/mL.

In any embodiment of the invention, the drug provisioning component can deliver the natriuretic peptide at a fixed, pulsed, or variable rate.

In any embodiment of the invention, a drug provisioning component can consist of any of the following elements: an external or implantable drug delivery pump, an implanted or percutaneous vascular access port, a direct delivery catheter system, and a local drug-release device.

In any embodiment of the invention, a drug provisioning component can subcutaneously deliver a therapeutically effective amount of the natriuretic peptide at a continuous rate (ng/kg of body weight) matching the area under the curve of a subcutaneous bolus at 6000 ng/kg of the subject.

In any embodiment of the invention, any specified range is in addition to an endogenous concentration of the natriuretic peptide.

In any embodiment of the invention, the natriuretic peptide is selected from any one of long-acting natriuretic peptide (LANP), kaliuretic peptide (KP), urodilatin (URO), atrial natriuretic peptide (ANP), vessel dilator (VD), and brain natriuretic peptide (BNP).

In any embodiment, a method for administering a natriuretic peptide uses a drug provisioning component selected from an external or implantable drug delivery pump, an implanted or percutaneous vascular access port, a direct delivery catheter system, and a local drug-release device.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 30 shows an assessment schedule for screening prior to infusion and during a 6-hour subcutaneous infusion session.

FIG. 31 shows an assessment for after a 6-hour subcutaneous infusion session.

DETAILED DESCRIPTION OF THE INVENTION

Figure 1:
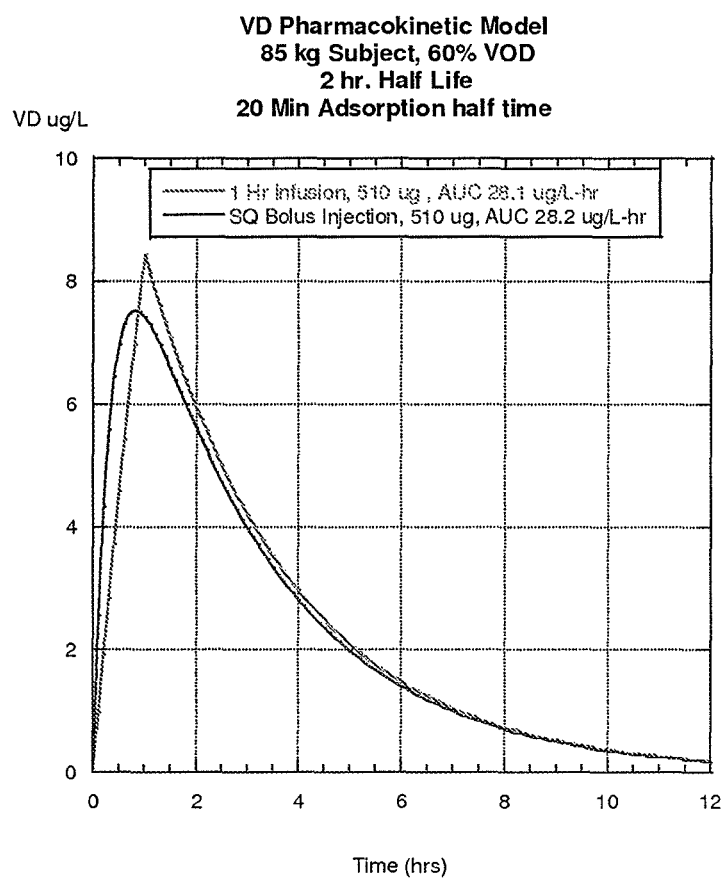
FIG. 1 shows the pharmacokinetic model of the subcutaneous injection as compared to an estimated model of the equivalent intravenous (IV) dosage for Vessel Dilator (VD) peptide.

The invention relates to selective delivery of a natriuretic peptide using a drug provisioning component that can include infusion pumps, implanted or percutaneous vascular access ports, direct delivery catheter systems, local drug-release devices or any other type of medical device that can be adapted to deliver a therapeutic to a subject. The drug provisioning component can administer the natriuretic peptide subcutaneously, intramuscularly, or intravenously at a fixed, pulsed, continuous or variable rate. A preferred embodiment of the invention contemplates subcutaneous delivery using an infusion pump at a continuous rate to maintain a specified plasma concentration of the natriuretic peptides. Natriuretic peptides and their sequences are disclosed in U.S. Pat. No. 5,691,310 and U.S. Patent App. Pub. Nos. 2006/0205642, 2008/0039394, 2009/0062206, and 2009/0170196, each of which is incorporated by reference herein in its entirety.

Definitions

Unless defined otherwise, all technical and scientific terms used herein generally have the same meaning as commonly understood by one of ordinary skill in the relevant art. Generally, the nomenclature used herein for drug delivery, pharmacokinetics, pharmacodynamics, and peptide chemistry is well known and commonly employed in the art. Further, the techniques for the discussed procedures are generally performed according to conventional methods in the art.

The articles "a" and "an" are used herein to refer to one or to more than one (i.e., to at least one) of the grammatical object of the article. By way of example, "an element" means one element or more than one element.

The terms "administering," "administer," "delivering," "deliver," "introducing," and "introduce" can be used interchangeably to indicate the introduction a compound, agent or peptide into the body of a patient, including methods of introduction where the compound, agent or peptide will be present in the blood or plasma of a subject to whom the compound, agent or peptide is administered.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase the phrase "consisting of." Thus, the phrase indicates that the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

"Pharmaceutically acceptable" is meant to encompass any carrier, which does not interfere with effectiveness of the biological activity of the active ingredient and that is not toxic to the host to which it is administered.

"Drug provisioning component" encompasses any and all devices that administers a therapeutic agent to a subject and includes infusion pumps, implanted or percutaneous vascular access ports, direct delivery catheter systems, local drug-release devices or any other type of medical device that can be adapted to deliver a therapeutic to a subject. The drug provisioning component and the control unit may be "co-located," which means that these two components, in combination, may make up one larger, unified unit of a system.

As used herein, "programmable" refers to a device using computer hardware architecture and being capable of carrying out a set of commands, automatically.

"Glomerular filtration rate" describes the flow rate of filtered fluid through the kidney. The estimated glomerular filtration rate or "eGFR" is a measure of filtered fluid based on a creatinine test and calculating the eGFR based on the results of the creatinine test.

"Intravenous" delivery refers to delivery of an agent by means of a vein.

"Intramuscular" delivery refers to delivery of an agent by means of muscle tissue.

"Subcutaneous" delivery refers to delivery of an agent by means of the subcutis layer of skin directly below the dermis and epidermis.

A "patch pump" is a device that adheres to the skin, contains a medication, and can deliver the drug over a period of time, either transdermally or via an integrated subcutaneous mini-catheter.

The term "delivering," "deliver," "administering," and "administers" can be used interchangeably to indicate the introduction of a therapeutic or diagnostic agent into the body of a subject in need thereof to treat a disease or condition, and can further mean the introduction of any agent into the body for any purpose.

The "field of chronic delivery" involves the following four parameters: period of treatment, scope, route of administration, and method of delivery. "Chronic delivery" means a period of treatment or drug delivery of more than 24 hours, even if the drug is not delivered continuously for that period of time. The scope of delivery involves one or more drugs, in any combination. The route of administration includes, but is not limited to, subcutaneous, intravascular, intraperitoneal and direct to organ, as described in further detail herein. The method of delivery includes, but is not limited to, implanted and external pumps, programmed or fixed rate, implanted or percutaneous vascular access ports, depot injection, direct delivery catheter systems, and local controlled release technology, as described in further detail herein.

The "field of acute delivery" involves the same four parameters as for the field of chronic delivery. The difference between the two fields is the period of treatment. "Acute delivery" means a period of treatment or drug delivery of less than or equal to 24 hours, even if the drug is delivered continuously for that period of time.

The term "therapeutically effective amount" refers to an amount of an agent (e.g., atrial natriuretic peptides) effective to treat at least one symptom of a disease or disorder in a subject. The "therapeutically effective amount" of the agent for administration may vary based upon the desired activity, the diseased state of the subject being treated, the dosage form, method of administration, subject factors such as the subject's sex, genotype, weight and age, the underlying causes of the condition or disease to be treated, the route of administration and bioavailability, the persistence of the administered agent in the body, evidence of natriuresis and/or diuresis, the type of formulation, and the potency of the agent.

The terms "treating" and "treatment" refer to the management and care of a patient having a pathology or condition for which administration of one or more therapeutic compounds or peptides is indicated for the purpose of combating or alleviating symptoms and complications of the condition. Treating includes administering one or more formulations or peptides of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "therapeutic regimen" is used according to its meaning accepted in the art and refers to, for example, a part of a treatment plan for an individual suffering from a pathological condition that specifies factors such as the agent or agents to be administered to the patient or subject, the doses of such agent(s), the schedule and duration of the treatment, etc.

An "infusion device" or "infusion pump" describes a means for delivering an infusion liquid into a patient or subject subcutaneously, intravenously, arterially, or by any other route of administration. Typically, the infusion pump has three major components: a fluid reservoir, a catheter system for transferring the fluids into the body, and a device that generates and/or regulates flow of the infusion fluid to achieve a desired concentration of a therapeutic agent in the body. One of ordinary skill will appreciate that there are many ways for regulating the flow of the infusion liquid by either mechanical or electric means. Hence, many forms for delivering the liquid are contemplated by the present invention, and such varied embodiments do not depart from the spirit of the invention. For example, the infusion fluid of the invention can be delivered and regulated using either roller pumps or electro-kinetic pumping (also known as electro-osmotic flow). Examples of infusion devices further include, but are not limited to, an external or an implantable drug delivery pumps.

The term "continuous infusion system" refers to a collection of components for continuously administering a fluid to a patient or subject for an extended period of time without having to establish a new site of administration each time the fluid is administered. As in the "infusion device" or "infusion pump," the fluid in the continuous infusion system typically contains a therapeutic agent or agents. The system typically has one or more reservoir(s) for storing the fluid(s) before it is infused, a pump, a catheter, cannula, or other tubing for connecting the reservoir to the administration site via the pump, and control elements to regulate the pump. The device may be constructed for implantation, usually subcutaneously. In such a case, the reservoir will usually be adapted for percutaneous refilling.

The terms "continuous administration" and "continuous infusion" are used interchangeably herein and mean delivery of an agent, such as an atrial natriuretic peptide, in a manner that, for example, avoids fluctuations in the in vivo concentrations of the agent throughout the course of a treatment period. "Delivery" as used herein, can mean any type of means to effect a result either by electrical, mechanical or other physical means. This can be accomplished by constantly or repeatedly injecting substantially identical amounts of the agent, typically with a continuous infusion pump device, for a set period of time, e.g., at least every hour, 24 hours a day, seven days a week for a period such as at least 3 to 7 days, such that a steady state serum or plasma level is achieved for the duration of the treatment. This can also be described as a cyclic on/off pattern. Continuous administration of the agent may also be made by subcutaneous, intravenous, or intra-arterial injection at appropriate intervals for an appropriate period of time in a pharmaceutically effective amount.

A "deliverable amount" is defined as any amount of a measured fluid that can be delivered through a fluid delivery catheter as known by those of ordinary skill in the art. "Delivery" as used herein generally, can mean any type of means to effect a result either by electrical, mechanical or other physical means.

"Risk" relates to the possibility or probability of a particular event occurring either presently or at some point in the future.

The terms "subject" and "patient" can be used interchangeably, and describe a member of any animal species, preferably a mammalian species, optionally a human. The animal species can be a mammal or vertebrate such as a primate, rodent, lagomorph, domestic animal or game animal. Primates include chimpanzees, cynomologous monkeys, spider monkeys, and macaques, e.g., Rhesus or Pan. Rodents and lagomorphs include mice, rats, woodchucks, ferrets, rabbits and hamsters. Domestic and game animals include cows, horses, pigs, sheep, deer, bison, buffalo, mink, felines, e.g., domestic cat, canines, e.g., dog, wolf and fox, avian species, e.g., chicken, turkey, emu and ostrich, and fish, e.g., trout, catfish and salmon. The subject can be an apparently healthy individual, an individual suffering from a disease, or an individual being treated for a disease.

The term "sample" refers to a quantity of a biological substance that is to be tested for the presence or absence of one or more molecules.

"Renin," also known as angiotensinogenase, is an enzyme that participates in the body's renin-angiotensin system (RAS), which regulates the body's mean arterial blood pressure by mediating extracellular volume (i.e., that of the blood plasma, lymph and interstitial fluid) and arterial vasoconstriction. Renin is released by the kidney when a subject has decreased sodium levels or low blood volume.

"Endogenous" substances are those that originate from within an organism, tissue, or cell.

The term "pharmacokinetics" is used according to its meaning accepted in the art and refers to the study of the action of drugs in the body. Pharmacokinetics includes, for example, the effect and duration of drug action, and the rate at which the drug is absorbed, distributed, metabolized, and eliminated by the body.

The term "pharmacodynamics" is used according to its meaning accepted in the art and refers to the study of the biochemical and physiological effects of drugs on the body, the mechanism of drug action, and the relationship between drug concentration and effect.

The phrase "area under the curve" or "AUC" refers to the area under a plasma concentration versus time curve. It indicates a measurement of drug absorption. AUC is described by the following formula:

$$AUC = \int_0^\infty C(t) dt$$

where C(t) indicates the concentration of the drug in the plasma at time t.

"Half-life" or "half-time" as used herein in the context of administering a peptide drug to a patient is defined as the time required for the blood plasma concentration of a substance to halve ("plasma half-life") its steady state. The knowledge of half-life is useful for the determination of the frequency of administration of a drug for obtaining a desired plasma concentration. Generally, the half-life of a particular drug is independent of the dose administered. There could also be more than one half-life associated with the peptide drug depending on multiple clearance mechanisms, redistribution, and other mechanisms known in the art. Usually, alpha and beta half-lives are defined such that the alpha phase is associated with redistribution, and the beta phase is associated with clearance. For protein drugs that are, for the most part, confined to the bloodstream, there can be at least two clearance half-lives.

"Elimination" refers to the removal or transformation of a drug in circulation, usually via the kidney and liver.

"Elimination half-life" is the time required for the amount of drug in the body to decrease by 50%.

"Absorption" refers to the transition of drug from the site of administration to the blood circulation.

The term "specified range," as used herein contemplates both a measured value, such as the concentration value of an agent or peptide in the plasma of a patient, and a measured value that is either added or subtracted from a normal or basal level of a subject.

"Loading dose" refers to the dose(s) of drugs given at the onset of therapy to rapidly provide a therapeutic effect. Use of a loading dose prior to a maintenance dosage regimen will shorten the time required to approach a steady state.

In pharmacokinetics, "steady state" represents the equilibrium between the amount of drug given and the amount eliminated over the dosing interval. In general, it takes drug four to five half-lives to reach a steady state, however the multiple can vary depending on the route of administration. Sampling should occur when the drug has reached its steady state to judge efficacy and toxicity of the drug therapy. Steady state should not be confused with the therapeutic range.

"Mean steady state concentration," denoted by "Css" refers to the concentration of a drug or chemical in a body fluid, usually plasma, at the time a "steady state" has been achieved and rates of drug administration and drug elimination are equal. Steady state concentrations fluctuate between a maximum (peak) ("Cmax") and minimum (trough) ("Cmin") concentration with each dosing interval. Css is a value approached as a limit and is achieved following the last of an infinite number of equal doses given at equal intervals.

"Plasma concentration" (Cp) refers to the amount of a drug in the blood plasma of the patient.

"Maximum plasma concentration" ($C_{max}$) refers to the maximum amount of a drug observed in the blood of a patient or subject.

"Average plasma concentration" ($C_{avg}$) refers to the average amount of a drug observed in the blood of a patient or subject over a time course of a period of observation of the amount of the drug in the blood.

"Minimum plasma concentration" ($C_{mm}$) refers to the minimum amount of a drug observed in the blood of a patient or subject over a time course of a period of observation of the amount of the drug in the blood.

"Time to maximum concentration" ($T_{max}$) refers to the time observed to reach maximum plasma concentration of a drug as measured from the initiation of regimen of administration of the drug.

"Percent fluctuation" (% Fluctuation) refers to the difference between $C_{max}$ and $C_{min}$ for a drug in the blood over a time course of a period of observation of the amount of the drug in the blood, where $$\% \text{ Fluctuation} = \frac{C_{max} - C_{min}}{C_{avg}} \times 100.$$

The "volume of distribution" (VOD) is a hypothetical volume that is the proportionality constant which relates the concentration of drug in the blood or serum and the amount of drug in the body.

"Pharmacokinetic constraints," as used herein, describes any factor that determines the pharmacokinetic profile of a drug such as immunogenicity, route of administration, endogenous concentrations of the natriuretic peptides, diurnal variation, and rate of drug delivery.

A "dose-response" relationship describes how the likelihood and severity of adverse health effects (i.e., the responses) are related to the amount and condition of exposure to an agent (i.e., the dose provided). Dose-response assessment is a two step process. The first step involves an assessment of all data that are available or can be gathered through experiments, in order to document the dose-response relationship(s) over the range of observed doses (i.e., the doses that are reported in the data collected). However, frequently this range of observation may not include sufficient data to identify a dose where the adverse effect is not observed (i.e., the dose that is low enough to prevent the effect) in the human population. The second step consists of extrapolation to estimate the risk, or probably of adverse effect, beyond the lower range of available observed data to make inferences about the critical region where the dose level begins to cause the adverse effect in the test population.

A "dose-response database," as used in the invention is a computer database that stores the data collected for dose-response assessment. The database thus provides inputs for mathematical modeling for computing risk of various adverse effects that are to be associated with the drug and certain doses of the drug.

"Patient parameters," as described herein includes parameters that may affect the efficacy of therapy or indicate a parameter that affects the efficacy of therapy, e.g., activity, activity level, posture, or a physiological parameter of the patient or subject. Other physiological patient parameters include heart rate, respiration rate, respiratory volume, core temperature, blood pressure, blood oxygen saturation, partial pressure of oxygen within blood, partial pressure of oxygen within cerebrospinal fluid, muscular activity, arterial blood flow, electromyogram (EMG), an electroencephalogram (EEG), an electrocardiogram (ECG), or galvanic skin response.

"Selective release" of an atrial natriuretic peptide as used in the invention describes the controlled delivery of a therapeutic using the drug delivery component, and can also refer to a controlled or programmed release of the atrial natriuretic peptide into the vasculature of the patient, according to a treatment protocol, through use of the drug provisioning component.

A "subcutaneous bolus injection" is the subcutaneous administration of a "bolus," of a medication, drug or other compound that is given, to a subject to raise concentration of the compound in the subject's blood to a desired level. Specifically, the injection is made in the subcutis, the layer of skin directly below the dermis and epidermis, collectively referred to as the cutis. The bolus injection may be delivered using a pump that may be programmable.

An "intra-arterial fluid delivery catheter," or the phrase "catheter specially adapted for insertion in an artery" is defined as a small tube configured for insertion into an artery for the purpose of delivering a fluid into the circulatory system of the patient. Similarly, an "intravenous fluid delivery catheter" is defined as a small tube configured for insertion into a vein for the purpose of delivering a fluid into the circulatory system of the patient.

The "distal tip" of a catheter is the end that is situated farthest from a point of attachment or origin, and the end closest to the point of attachment or origin is known as the "proximal" end.

"Vascular access ports," as described herein, are ports for infusing and/or withdrawing fluid from a patient. The vascular access or infusion ports typically incorporate mechanical valves which open during use, such as when a needle is inserted into the port, and close in between use, such as when a needle is removed from the part. In certain forms, the ports can be positioned subcutaneously underneath the skin, or percutaneously when the access part of the port is placed above the level of the skin to be accessed without skin penetration eliminating the need for using needle sticks to access the vasculature. Vascular access devices may also be implantable. These devices typically consist of a portal body and a catheter. The catheter may be either integral with the portal body or separate from the body to be attached at the time of implantation.

A "direct delivery catheter system," as used herein is a catheter system for guiding an elongated medical device into an internal bodily target site. The system can have a distal locator for locating a target site prior to deployment of the catheter. The catheter can be introduced through a small incision into the bodily vessel, channel, canal, or chamber in question; or into a bodily vessel, channel, canal, or chamber that is otherwise connected to the site of interest (or target site), and then guided through that vessel to the target site.

The term "peptide," as used herein, describes an oligopeptide, polypeptide, peptide, protein or glycoprotein, and includes a peptide having a sugar molecule attached thereto. As used herein, "native form" means the form of the peptide when produced by the cells and/or organisms in which it is found in nature. When the peptide is produced by a plurality of cells and/or organisms, the peptide may have a variety of native forms. "Peptide" can further refer to a polymer in which the monomers are amino acids that are joined together through amide bonds. Also included are peptides which have been modified using ordinary molecular biological techniques so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The present invention also embraces recombination peptides such as recombinant human ANP (hANP) obtained from bacterial cells after expression inside the cells. It will be understood by those of skill in the art that the peptides and recombinant peptides of the present invention can be made by varied methods of manufacture wherein the peptides of the invention are not limited to the products of any of the specific exemplary processes listed herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The present invention also provides for analogs of proteins or peptides which comprise a protein as identified above.

The term "fragment," as used herein, refers to a polypeptide that comprises at least six contiguous amino acids of a polypeptide from which the fragment is derived. In preferred embodiments, a fragment refers to a polypeptide that comprises at least 10 contiguous amino acids of a polypeptide from which the fragment is derived, more preferably at least 10 contiguous amino acids, still more preferably at least 15 contiguous amino acids, and still more preferably at least 20 contiguous amino acids of a polypeptide from which the fragment is derived.

The term "natriuretic peptide fragment" refers to a fragment of any natriuretic peptide defined and described herein.

As used herein, "cardiovascular disease" refers to various clinical diseases, disorders or conditions involving the heart, blood vessels, or circulation. Cardiovascular disease includes, but is not limited to, coronary artery disease, peripheral vascular disease, hypertension, myocardial infarction, and heart failure.

The terms "natriuretic" or "natriuresis" refer to the ability of a substance to increase sodium clearance from a subject.

The terms "renal or cardiovascular protective" and "renal or cardiovascular protective effects" refer to the ability of a substance to improve one or more functions of the kidneys or heart of a subject, including natriuresis, diuresis, cardiac output, hemodynamics, renal cortical blood flow or glomerular filtration rate, or to lower the blood pressure of the subject. Any measurable diagnostic factor that would be recognized by one having skill in the art as reducing stress on the kidneys and/or heart or as evidence of improvement in the function of the renal or cardiovascular system can be considered a renal or cardiovascular protective effect. The term "renal protective" or "renal protective effect" refers to a measurable diagnostic factor that would be recognized by one having skill in the art as particularly related to an indication of reduced stress on the kidneys or improvement in renal function. The term "cardiovascular protective" or "cardiovascular protective effect" refers to a measurable diagnostic factor that would be recognized by one having skill in the art as particularly related to an indication of reduced stress on the cardiovascular system or improvement in cardiac function.

As used herein, "heart failure" (HF) refers to a condition in which the heart cannot pump blood efficiently to the rest of the body. Heart failure may be caused by damage to the heart or narrowing of the arteries due to infarction, cardiomyopathy, hypertension, coronary artery disease, valve disease, birth defects or infection. Heart failure may also be further described as chronic, congestive, acute, decompensated, acute decompensated, systolic, or diastolic. The NYHA classification describes the severity of the disease based on functional capacity of the patient and is incorporated herein by reference. Heart failure can be with preserved ejection fraction or be with reduced ejection fraction. Further, heart failure can include left heart failure or right heart failure.

"Acute heart failure" means a sudden onset or episode of an inability of the heart to pump a sufficient amount of blood with adequate perfusion and oxygen delivery to internal organs. Acute heart failure can be accompanied by congestion of the lungs, shortness of breadth and/or edema.

Relating to heart failure, for example, "increased severity" of cardiovascular disease refers to the worsening of the disease as indicated by increased New York Heart Association (NYHA) classification, and "reduced severity" of cardiovascular disease refers to an improvement of the disease as indicated by reduced NYHA classification.

The "renal system," as defined herein, comprises all the organs involved in the formation and release of urine including the kidneys, ureters, bladder and urethra.

"Proteinuria" is a condition in which urine contains an abnormal amount of protein. Albumin is the main protein in the blood; the condition where the urine contains abnormal levels of albumin is referred to as "albuminuria." Healthy kidneys filter out waste products while retaining necessary proteins such as albumin. Most proteins are too large to pass through the glomeruli into the urine. However, proteins from the blood can leak into the urine when the glomeruli of the kidney are damaged. Hence, proteinuria is one indication of kidney disease (KD).

"Kidney disease" (KD) is a condition characterized by the slow loss of kidney function over time. The most common causes of KD are high blood pressure, diabetes, heart disease, and diseases that cause inflammation in the kidneys. Kidney disease can also be caused by infections or urinary blockages. If KD progresses, it can lead to end-stage renal disease (ESRD), where the kidneys fail completely. In the Cardiorenal Syndrome (CRS) classification system, CRS Type I (Acute Cardiorenal Syndrome) is defined as an abrupt worsening of cardiac function leading to acute kidney injury; CRS Type II (Chronic Cardiorenal syndrome) is defined as chronic abnormalities in cardiac function (e.g., chronic congestive heart failure) causing progressive and permanent kidney disease; CRS Type III (Acute Renocardiac Syndrome) is defined as an abrupt worsening of renal function (e.g., acute kidney ischaemia or glomerulonephritis) causing acute cardiac disorders (e.g., heart failure, arrhythmia, ischemia); CRS Type IV (Chronic Renocardiac syndrome) is defined as kidney disease (e.g., chronic glomerular disease) contributing to decreased cardiac function, cardiac hypertrophy and/or increased risk of adverse cardiovascular events; and CRS Type V (Secondary Cardiorenal Syndrome) is defined as a systemic condition (e.g., diabetes mellitus, sepsis) causing both cardiac and renal dysfunction (Ronco et al., Cardiorenal syndrome, J. Am. Coll. Cardiol. 2008; 52:1527-39). KD can be referred to by different stages indicated by Stages 1 to 5. Stage of KD can be evaluated by glomerular filtration rate of the renal system. Stage 1 KD can be indicated by a GFR greater than 90 mL/min/1.73 $m^2$ with the presence of pathological abnormalities or markers of kidney damage. Stage 2 KD can be indicated by a GFR from 60-89 mL/min/1.73 $m^2$, Stage 3 KD can be indicated by a GFR from 30-59 mL/min/1.73 $m^2$ and Stage 4 KD can be indicated by a GFR from 15-29 mL/min/1.73 $m^2$. A GFR less than 15 mL/min/1.73 $m^2$ indicates Stage 5 KD or ESRD. It is understood that KD, as defined in the present invention, contemplates KD regardless of the direction of the pathophysiological mechanisms causing KD and includes CRS Type II and Type IV and Stage 1 through Stage 5 KD among others. Kidney disease can further include acute renal failure, acute kidney injury, and worsening of renal function.

"Hemodynamics" is the study of blood flow or circulation. The factors influencing hemodynamics are complex and extensive but include cardiac output (CO), circulating fluid volume, respiration, vascular diameter and resistance, and blood viscosity. Each of these may in turn be influenced by physiological factors. Hemodynamics depends on measuring the blood flow at different points in the circulation. Blood pressure is the most common clinical measure of circulation and provides a peak systolic pressure and a diastolic pressure. "Blood pressure" (BP) is the pressure exerted by circulating blood upon the walls of blood vessels. Invasive hemodynamic monitoring measures pressures within the heart. One of the most widely used methods of hemodynamic monitoring is the use of the Swan-Ganz Catheter. Through the use of the Swan-Ganz catheter one can measure central venous pressure (CVP) and obtain a subject's CO.

"Central venous pressure" (CVP) describes the pressure of blood in the thoracic vena cava, near the right atrium of the heart. CVP reflects the amount of blood returning to the heart and the ability of the heart to pump the blood into the arterial system. Another method for obtaining the cardiac output is using the Fick Method, in which a port is disposed in the pulmonary artery and measures pulmonary artery pressures. This port can also be configured to have a balloon that when inflated measures the pulmonary artery wedge pressure (PCWP).

"Mean arterial pressure" (MAP) is a term used in medicine to describe an average blood pressure in an individual. It is defined as the average arterial pressure during a single cardiac cycle.

"Left atrial pressure" (LAP) refers to the pressure in the left atrium of the heart. Pulmonary artery wedge pressure is used to provide an indirect estimate of LAP. Although left ventricular pressure can be directly measured by placing a catheter into the left ventricle by feeding it through a peripheral artery, into the aorta, and then into the ventricle, it is not feasible to advance this catheter back into the left atrium. LAP can be measured by placing a special catheter into the right atrium then punching through the interatrial septum; however, this is not usually performed because of damage to the septum and potential harm to the patient.

"Right atrial pressure" refers to the pressure in the right atrium of the heart. Central venous pressure is used to provide an indirect, noninvasive, measure of right atrial pressure.

The term "intrinsic" is used herein to describe something that is situated within or belonging solely to the organ or body part on which it acts. Therefore, "intrinsic natriuretic peptide generation" refers to a subject's making or releasing of one or more natriuretic peptides by its respective organ(s).

"Cardiac output" (CO), or (Q), is the volume of blood pumped by the heart per minute (mL/min). Cardiac output is a function of heart rate and stroke volume. The heart rate is simply the number of heart beats per minute. The stroke volume is the volume of blood, in milliliters (mL), pumped out of the heart with each beat. Increasing either heart rate or stroke volume increases cardiac output. Cardiac Output in mL/min=heart rate (beats/min)×stroke volume (mL/beat).

A "buffer solution" is an aqueous solution consisting of a mixture of a weak acid and its conjugate base or a weak base and its conjugate acid. It has the property that the pH of the solution changes very little when a small amount of strong acid or base is added to it. Buffer solutions are used as a means of keeping pH at a nearly constant value in a wide variety of chemical applications. "Buffered saline solution," as used herein, refers to a phosphate buffered saline solution, which is a water-based salt solution containing sodium chloride, sodium phosphate, and (in some formulations) potassium chloride and potassium phosphate. The buffer helps to maintain a constant pH. The osmolarity and ion concentrations of the solution usually match those of the human body.

A "control system" consists of combinations of components that act together to maintain a system to a desired set of performance specifications. The performance specifications can include sensors and monitoring components, processors, memory and computer components configured to interoperate.

A "controller" or "control unit" is a device which monitors and affects the operational conditions of a given system. The operational conditions are typically referred to as output variables of the system, which can be affected by adjusting certain input variables.

By the phrase, "in communication," it is meant that the elements of the system of the invention are so connected, either directly or remotely, wirelessly or by direct electrical contact so that data and instructions can be communicated among and between said elements.

"Controlled delivery" refers to the implementation of a controller or control unit that is either programmable or patient-controlled that causes the drug delivery component to administer the therapeutic agent to the patient according to a programmed administration protocol or in response to a command given by the patient or a healthcare provider.

"Patient controlled" delivery refers to mechanisms by which the patient can administer and/or control the administration of a drug. Thus, the patient can cause the drug delivery component to administer the therapeutic formulation.

The term "a cyclic on/off pattern" as used herein means a repetitive condition which alternates between being in "on" and "off" states. Such conditions may pertain to drug delivery by a drug provisioning component of a medical system wherein the "on" state denotes a period of drug delivery. A drug administered in "a cyclic on/off pattern" is delivered as repetitive doses over duration of time.

The term "maintaining a plasma concentration" refers to, in some embodiments, maintaining a concentration of a compound or peptide in the plasma of a subject at a recited or referenced concentration range by administration of the compound or peptide by any appropriate means. In certain other embodiments, "maintaining a plasma concentration" refers to maintaining a concentration of a compound or peptide at a concentration in the plasma of a subject that is in addition to an endogenous concentration of that compound or peptide. Where the compound or peptide is a naturally occurring substance, a subject can have an endogenous baseline of that compound or peptide measurable in the plasma. Maintaining a plasma concentration at a recited concentration can refer to increasing the plasma concentration of the compound or peptide by the recited amount and maintaining a plasma concentration at that elevated amount.

The term "multiple days" refers to any duration of time greater than 24 hours.

The term "pulmonary capillary wedge pressure" refers to the pressure measured by wedging a pulmonary catheter with a deflated balloon into a small pulmonary arterial branch.

Measurements of pharmacokinetic variables such as steady state concentration, absorption half-life, administration rate, volume of distribution, elimination half-life, and clearance are described as ranges. The measurement ranges are represented by equations encompassing groups of ranges. Specifically, the values of pharmacokinetic variables are described as ranges from n to (n+i), wherein the definitions of n and i are specific to a particular pharmacokinetic variable. It is to be understood that a given range supports every possible permutation thereof, and accordingly all such permutations are therefore contemplated by the invention.

As used herein, a range from n to (n+i) is subject to the constraints $n=\{x \epsilon R | \alpha \leq x \leq \beta\}$, for $\alpha \neq 0$, and $i=\{y \epsilon R | 0 \leq y \leq (\beta-n)\}$, or $n=\{x \epsilon R | \alpha < x \leq \beta\}$ for $\alpha \geq 0$, and $i=\{y \epsilon R | 0 \leq y \leq (\beta-n)\}$, or other similar constraints, where $\alpha$ is a minimum value specific to a pharmacokinetic variable, and $\beta$ is a maximum value specific to a pharmacokinetic variable. Such a range, n to (n+i), also inherently supports any sub-range falling within the larger range.

In an example where $\alpha=0$, and $\beta=500$, a range from n to (n+i) where $n=\{x \epsilon R | 0 < x \leq 500\}$), and $i=\{y \epsilon R | 0 \leq y \leq (500-n)\}$, would encompass all values ranging from greater than 0 up to and including 500, and additionally all sub-ranges within the range of 0 to 500. Specifically, for this example range, a lower bound may be chosen such that x=0.5 meaning the lower bound, n, of a sub-range is 0.5, and the upper bound, (n+i), could be any value from 0.5 to 500. Any sub-range lower bound may be chosen subject to the constraints. For example, if x=10, the lower bound of the sub-range would be 10, and the upper bound could be any value from 10 to 500, thus yielding sub-ranges such as 10-10, 10-10.5, 10-20, 10-25.6, . . . , 10-500. Likewise, if x=45.3, the lower bound of the sub-range would be 45.3, and the upper bound could be any value from 45.3 to 500, thus yielding sub-ranges such as 45.3-45.3, 45.3-45.4, 45.3-46.5, . . . , 45.3-500.

In an example where $\alpha=2$, and $\beta=450$, a range from n to (n+i) where $n=\{x \epsilon R | 2 < x \leq 450\}$, and $i=\{y \epsilon R | 0 \leq y \leq (450-n)\}$, would encompass all values ranging from greater than 2 up to and including 450, and additionally all sub-ranges within the range of 2 to 450. Specifically, for this example range, a lower bound may be chosen such that x=2.5 meaning the lower bound, n, of a sub-range is 2.5, and the upper bound, (n+i), could be any value from 2.5 to 450. Any sub-range lower bound may be chosen subject to the constraints. For example, if x=10, the lower bound of the sub-range would be 10, and the upper bound could be any value from 10 to 450, thus yielding sub-ranges such as 10-10, 10-10.5, 10-20, 10-25.6, . . . , 10-450. Likewise, if x=45.3, the lower bound of the sub-range would be 45.3, and the upper bound could be any value from 45.3 to 450, thus yielding sub-ranges such as 45.3-45.3, 45.3-45.4, 45.3-46.5, . . . , 45.3-450.

In an example where α=2, and β=450, a range from n to (n+i) where n={x∈R|2≤x≤450}, and i={y∈R|0≤y≤(450−n)}, would encompass all values ranging from 2 up to and including 450, and additionally all sub-ranges within the range of 2 to 450. Specifically, for this example range, a lower bound may be chosen such that x=2 meaning the lower bound, n, of a sub-range is 2, and the upper bound, (n+i), could be any value from 2 to 450. Any sub-range lower bound may be chosen subject to the constraints. For example, if x=10, the lower bound of the sub-range would be 10, and the upper bound could be any value from 10 to 450, thus yielding sub-ranges such as 10-10, 10-10.5, 10-20, 10-25.6, . . . , 10-450. Likewise, if x=45.3, the lower bound of the sub-range would be 45.3, and the upper bound could be any value from 45.3 to 450, thus yielding sub-ranges such as 45.3-45.3, 45.3-45.4, 45.3-46.5, . . . , 45.3-450. Accordingly, all permutations of a broad range and a sub-range therein are contemplated by the range equations described.

Rates of administration of a natriuretic peptide or other material can be expressed as an absolute rate of a weight or mole amount of the peptide per unit of time or as a weight-based rate that varies based on a subject's weight. For example, the term 10 ng/kg·min means that 10 ng of a chimeric natriuretic peptide is administered to the subject every minute for every kg of body weight of the subject. As such, an 85-kg subject receiving a weight-based dose of 10 ng/kg·min receives 850 ng/min of the natriuretic peptide or an absolute rate of 51 μg/hr of the natriuretic peptide. The units ng/kg·min, ng/(kg·min), ng kg$^{-1}$ min$^{-1}$ and ng/kg/min are equivalent and have the same meaning as described herein.

Natriuretic Peptides

Natriuretic peptides are a family of peptides having a 17 amino acid disulphide ring structure acting in the body to oppose the activity of the renin-angiotensin system. The natriuretic peptides have been the focus of intense study subsequent to the seminal work by DeBold et al. on the potent diuretic and natriuretic properties of atrial extracts and its precursors in atrial tissues (A rapid and potent natriuretic response to intravenous injection of atrial myocardial extract in rats, Life Sci., 1981; 28(1): 89-94). In humans, the family consists of atrial natriuretic peptide (ANP) of myocardial cell origin, C-type natriuretic peptide (CNP) of endothelial origin, brain natriuretic peptide (BNP) and urodilatin (URO), which is thought to be derived from the kidney. Atrial natriuretic peptide (ANP), alternatively referred to in the art as atrial natriuretic factor (ANF), is secreted by atrial myocytes in response to increased intravascular volume. Once ANP is in the circulation, its effects are primarily on the kidney, vascular tissue, and adrenal gland. ANP leads to the excretion of sodium and water by the kidneys and to a decrease in intravascular volume and blood pressure. Brain natriuretic peptide (BNP) also originates from myocardial cells and circulates in human plasma similar to ANP. BNP is natriuretic, renin inhibiting, vasodilating, and lusitropic. C-type natriuretic peptide (CNP) is of endothelial cell origin and functions as a vasodilating and growth-inhibiting polypeptide. Natriuretic peptides have also been isolated from a range of other vertebrates. For example, *Dendroaspis angusticeps* natriuretic peptide is detected in the venom of *Dendroaspis angusticeps* (the green mamba snake); CNP analogues are cloned from the venom glands of snakes of the Crotalinae subfamily; *Pseudocerastes persicus* natriuretic peptide is isolated from the venom of the Iranian snake (*Pseudocerastes persicus*), and three natriuretic-like peptides (TNP-a, TNP-b, and TNP-c) are isolated from the venom of the Inland Taipan (*Oxyuranus microlepidotus*). Because of the capacity of natriuretic peptides to restore hemodynamic balance and fluid homeostasis, they can be used to manage cardiopulmonary and renal symptoms of cardiac disease due to its vasodilator, natriuretic and diuretic properties.

The five major ANP hormones are atrial long-acting natriuretic peptide (LANP), kaliuretic peptide (KP), urodilatin (URO), atrial natriuretic peptide (ANP), and vessel dilator (VD). These hormones function via well-characterized particulate guanylyl cyclase receptors linked to cGMP, and have significant blood pressure lowering, diuretic, sodium and/or potassium excreting properties in healthy humans. Atrial natriuretic peptide (ANP) has been implicated in diseases and disorders involving volume regulation, such as congestive heart failure, hypertension, liver disease, nephrotic syndrome, and acute and chronic renal failure. In the heart, ANP has growth regulatory properties in blood vessels that inhibit smooth muscle cell proliferation (hyperplasia) as well as smooth muscle cell growth (hypertrophy). ANP also has growth regulatory properties in a variety of other tissues, including brain, bone, myocytes, red blood cell precursors, and endothelial cells. In the kidneys, ANP causes antimitogenic and antiproliferative effects in glomerular mesangial cells. ANP has been infused intravenously to treat hypertension, heart disease, acute renal failure and edema, and shown to increase the glomerular filtration rate (GFR) and filtration fraction. ANP has further been shown to reduce proximal tubule sodium ion concentration and water reabsorption, inhibit net sodium ion reabsorption and water reabsorption in the collecting duct, lower plasma renin concentration, and inhibit aldosterone secretion. Further, administration of ANP has resulted in mean arterial pressure reduction.

Within the 126 amino acid (a.a.) ANP prohormone are four peptide hormones: long acting natriuretic peptide (LANP) (also known as proANP 1-30) (a.a. 1-30), vessel dilator. (VD) (a.a. 31-67), kaliuretic peptide (KP) (a.a. 79-89), and atrial natriuretic peptide (ANP) (a.a. 99-126), whose main known biologic properties are blood pressure regulation and maintenance of plasma volume in animals and humans. The peptide sequences for these four ANP peptide hormones are as follows:

```
proANP or LANP, (a.a. 1-30)
                                    (SEQ ID No. 1)
NPMYNAVSNADLMDFKNLLDHLEEKMPLED Vessel Dilator, (a.a. 31-67)
                                    (SEQ ID No. 2)
EVVPPQVLSEPNEEAGAALSPLPEVPPWTGEVSPAQR Kaliuretic Peptide, (a.a. 79-98)
                                    (SEQ ID No. 3)
SSDRSALLKSKLRALLTAPR ANP, (a.a. 99-126)
                                    (SEQ ID No. 4)
SLRRSSCFGGRMDRIGAQSGLGCNSFRY
```

The fifth member of the atrial natriuretic peptide family, urodilatin (URO) (ANP a.a. 95-126) is isolated from human urine and has an N-terminal extension of four additional amino acids, as compared with the circulating form of ANP (a.a. 99-126). This hormone is synthesized in the kidney and exerts potent paracrine renal effects. (Meyer, M. et al., Urinary and plasma urodilatin measured by a direct RIA using a highly specific antiserum, Clin. Chem., 1998; 44(12):2524-2529). Several studies have suggested that URO is involved in the physiological regulation of renal function, particularly in the control of renal sodium and water excretion wherein a concomitant increase in sodium and URO excretion was observed after acute volume load and after dilation of the left atrium. Additionally, infusions and bolus injections of URO in rats and healthy volunteers have also revealed the pharmacological potency of this natriuretic peptide wherein intense diuresis and natriuresis as well as a slight reduction in blood pressure are the most prominent effects. The strength and duration of these effects differ considerably from ANP a.a. 99-126. The sequence for urodilatin is provided in SEQ ID No. 5.

```
Urodilatin (a.a. 95-126)
                                      (SEQ ID No. 5)
TAPRSLRRSSCFGGRMDRIGAQSGLGCNSFRY
```

The peptide sequence for BNP is as follows:

```
BNP
                                      (SEQ ID No. 6)
SPKMVQGSGCFGRKMDRISSSSGLGCKVLRRH
```

The role of the ANP hormones in diseases and disorders involving volume regulation, such as congestive heart failure, hypertension, liver disease, nephrotic syndrome, and acute and chronic renal failure, has been studied in human and animal models. Because ANP prohormone is secreted in response to atrial stretch, ANP levels are elevated in patients having congestive heart failure (CHF). The plasma level of ANP can indicate the severity of CHF, and correlates directly with right atrial and pulmonary capillary wedge pressures and inversely with cardiac index, stroke volume, blood pressure, and New York Heart Association functional class (Brenner et al., Diverse biological actions of atrial natriuretic peptide, Physiol. Rev., 1990; 70(3): 665-699).

Drug Delivery of Natriuretic Peptides

The systems and methods of the invention are directed to the administration of a natriuretic peptide to a patient for the treatment of Kidney Disease (KD) alone, Heart Failure (HF) alone, or KD with concomitant HF. It is understood that both separate and/or simultaneous treatment of KD and HF is contemplated by the invention. The systems and methods of the invention are also useful for treating other renal or cardiovascular diseases, such as heart failure, dyspnea, elevated pulmonary capillary wedge pressure, chronic renal insufficiency, kidney disease, acute renal failure, cardiorenal syndrome, and diabetes mellitus, any combination of which may be treated simultaneously or separately.

The plasma levels of the natriuretic peptides can be increased by causing the selective release of natriuretic peptide using a drug provisioning component. A control consisting of a computer processor unit may also be present that is connected to and in communication with the drug provisioning component. The control unit of the invention contains a set of instructions that causes the drug provisioning component to administer the natriuretic peptide to the patient according to a therapeutic regimen. The therapeutic regimen is tailored so that the plasma concentration of the natriuretic peptide is maintained within a specified range by effecting controlled administration of the natriuretic peptides using the drug provisioning component. This specified concentration is preferably not greater than a plasma level reached by either a single subcutaneous bolus injection of the natriuretic peptide at 6000 ng of the natriuretic peptide per kilogram of the patient's body weight or a level reached by a one hour intravenous infusion of the natriuretic peptide at 100 ng of the natriuretic peptide per kilogram·minute of the patient's body weight.

In some embodiments, the drug provisioning component used in the methods of the invention is a continuous infusion apparatus. The continuous infusion apparatus is configured to impact the basal rate of infusion of the therapeutic formulation. The "basal rate" is the continuous infusion rate of the drug that may be programmed. The continuous infusion apparatus preferably administers the natriuretic peptide to the patient subcutaneously and in accordance with the therapeutic regimen. Alternatively, the drug provisioning component may contain an infusion apparatus designed to implement a bolus infusion rate. "Bolus" infusion is a rapid infusion of a drug to expedite the effect rapidly by increasing drug concentration level in the blood. The drug provisioning component may be configured to use both basal rate and bolus rate infusion or to use only one infusion method, either basal rate or bolus. The drug provisioning component may also be configured to deliver a drug in a cyclic on/off or repeating pattern alternating between an "on" and "off" state where the drug is delivered as a set of repetitive doses over duration of time.

In embodiments where the therapeutic agent is administered in a substantially continuous manner, suitable types of pumps include, but are not limited to, osmotic pumps, interbody pumps, infusion pumps, implantable pumps, peristaltic pumps, other pharmaceutical pumps, or a system administered by insertion of a catheter at or near an intended delivery site, the catheter being operably connected to the pharmaceutical delivery pump. In one embodiment, the catheter can be used to directly infuse a kidney via a renal artery catheter. The term "substantially continuous manner," as contemplated herein, means that the dosing rate is constantly greater than zero during the periods of administration. The term includes embodiments when the therapeutic agent is administered at a steady rate, e.g., via a continuous infusion apparatus. In some embodiments, the natriuretic peptide may be administered only in a substantially continuous manner throughout the entire treatment period. In other embodiments, the contemplated manners of administration may be combined during the same stage or altered during different stages of the treatment.

Figure 2:
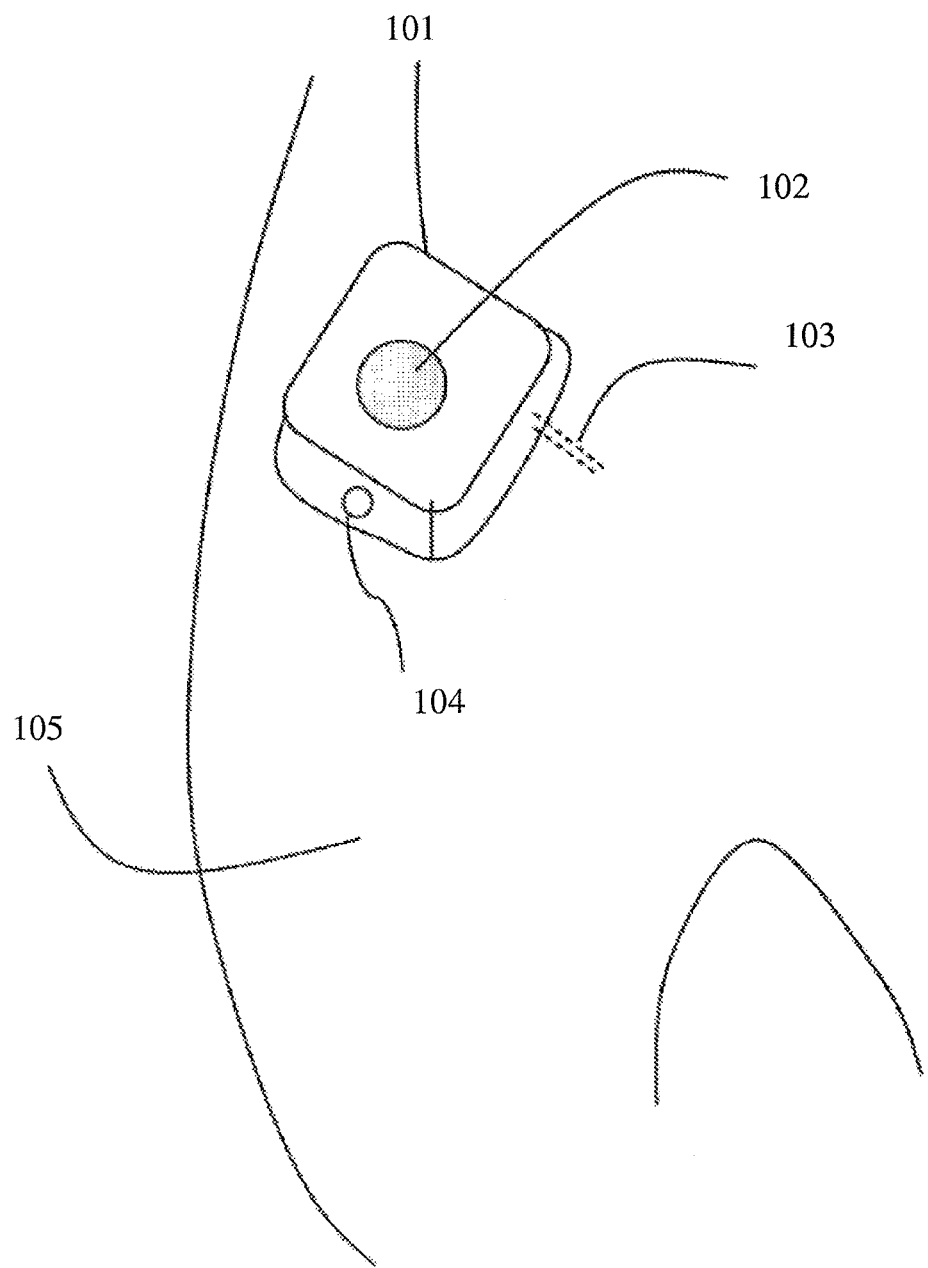
FIG. 2 shows a disposable external infusion pump.

It is understood that the pumps can be implanted internally, such as into a patient's peritoneal cavity, or worn externally, as appropriate. FIG. 2 illustrates a disposable external infusion pump 101 that is attached to the body 105 of a patient. The disposable external infusion pump includes a reservoir that contains the therapeutic formulation, which may comprise the natriuretic peptide. The pump may be operated by the patient, wherein the patient presses a button 102, which causes the release of a predetermined volume of the drug, and the drug is delivered to the body of the patient via cannula 103. The tip of the cannula is preferably located subcutaneously. In some embodiments, the reservoir may be refilled through a hole 104. Exemplary methods of the invention, as described herein, further employ a programmable feature. When selecting a suitable pump, a number of characteristics are considered. These characteristics include, but are not limited to, biocompatibility, reliability, durability, environmental stability, accuracy, delivery scalability, flow delivery (i.e., continuous versus pulse flow), portability, reusability, back pressure range and power consumption. Examples of suitable pumps known in the art are described herein. A person with ordinary skill in the art is capable of selecting an appropriate pump for methods and systems described herein.

Techniques related to infusion system operation, sensing and monitoring, signal processing, data transmission, signaling, network control, and other functional aspects of infusion pump and/or systems (and the individual operating components) are contemplated by the invention. Examples of infusion pumps and/or communication options may be of the type described in, but not limited to U.S. Pat. Nos. 4,562,751; 4,685,903; 5,080,653; 5,505,709; 5,097,122; 6,551,276, 6,554,798; 6,558,320; 6,558,351; 6,641,533; 6,423,035; 6,652,493; 6,656,148; 6,659,980; 6,752,787; 6,817,990; 6,872,200; 6,932,584; 6,936,029; 6,979,326; 6,997,920; and 7,025,743, which are herein incorporated by reference. Examples of external infusion pumps include Medtronic MiniMed® Paradigm® pumps and one example of a suitable implantable pump is Medtronic SynchroMed® pump, all manufactured by Medtronic, Inc., Minneapolis, Minn. Another example of an implantable drug pump is shown in Medtronic, Inc. "SynchroMed® Infusion System" Product Brochure (1995). Additional examples of external infusion pumps include Animas Corporation Animas® and OneTouch® Ping® pumps, manufactured by Animas Corporation, Frazer, Pa. Implantable drug pumps can use a variety of pumping mechanism such as a piston pump, rotary vane pump, osmotic pump, Micro Electro Mechanical Systems (MEMS) pump, diaphragm pump, peristaltic pump, and solenoid piston pump to infuse a drug into a patient. Peristaltic pumps typically operate by a battery powered electric motor that drives peristaltic rollers over a flexible tube having one end coupled to a therapeutic substance reservoir and the other end coupled to an infusion outlet to pump the therapeutic substance from the therapeutic substance reservoir through the infusion outlet. Examples of solenoid pumps are shown in U.S. Pat. No. 4,883,467 "Reciprocating Pump For An Implantable Medication Dosage Device" to Franetzki et al. (Nov. 28, 1989) and U.S. Pat. No. 4,569,641 "Low Power Electromagnetic Pump" to Falk et al. (Feb. 11, 1986). An example of a pump is shown in U.S. Pat. No. 7,288,085 "Permanent magnet solenoid pump for an implantable therapeutic substance delivery device," which is incorporated herein by reference. Further, the contents of U.S. Pat. App. Pub. No. 2008/0051716 directed to "Infusion pumps and methods and delivery devices and methods with same" is incorporated herein by reference. Additional examples of external pump type delivery devices are described in U.S. patent application Ser. No. 11/211,095, filed Aug. 23, 2005, titled "Infusion Device And Method With Disposable Portion" and Published PCT Application WO 2001/70307 (PCT/US01/09139), titled "Exchangeable Electronic Cards For Infusion Devices," Published PCT Application WO 2004/030716 (PCT/US2003/028769), titled "Components And Methods For Patient Infusion Device," Published PCT Application WO 2004/030717 (PCT/US2003/029019), titled "Dispenser Components And Methods For Infusion Device," U.S. Patent Application Publication No. 2005/0065760, titled "Method For Advising Patients Concerning Doses Of Insulin," and U.S. Pat. No. 6,589,229, titled "Wearable Self-Contained Drug Infusion Device," each of which is incorporated herein by reference in its entirety.

Typically, the continuous infusion device used in the methods of the invention has the desirable characteristics that are found, for example, in pumps produced and sold by Medtronic, such as Medtronic MiniMed® Paradigm® models. The Paradigm® pumps include a small, wearable control unit, which enables patients to program the delivery of the therapeutic agent via inputs and a display. The pump control unit includes microprocessors and software which facilitate delivery of the therapeutic agent fed from an included reservoir by a piston rod drive system. The pumps also include wireless telemetry for continuous system monitoring based on data obtained from optional sensors. Alternatively, continuous administration can be accomplished by, for example, another device known in the art, such as a pulsatile electronic syringe driver (e.g., Provider Model PA 3000, Pancretec Inc., San Diego Calif.), a portable syringe pump such as the Graseby model MS 16A (Graseby Medical Ltd., Watford, Hertfordshire, England), or a constant infusion pump such as the Disetronic Model Panomat C-S Osmotic pumps, such as that available from Alza, a division of Johnson & Johnson, may also be used. Since use of continuous subcutaneous injections allows the patient to be ambulatory, it is typically chosen over continuous intravenous injections.

External infusion pumps for use in embodiments of the invention can be designed to be compact (e.g., less than 15 cm×15 cm) as well as water resistant, and may thus be adapted to be carried by the user, for example, by means of a belt clip. Examples of external pump type delivery devices are described in U.S. patent application Ser. No. 11/211,095, filed Aug. 23, 2005, titled "Infusion Device And Method With Disposable Portion" and Published PCT Application No. WO 2001/70307 (PCT/US01/09139), titled "Exchangeable Electronic Cards For Infusion Devices" (each of which is owned by the assignee of the present invention), Published PCT Application No. WO 2004/030716 (PCT/US2003/028769), titled "Components And Methods For Patient Infusion Device," Published PCT Application No. WO 04/030717 (PCT/US2003/029019), titled "Dispenser Components And Methods For Infusion Device," U.S. Patent Application Publication No. 2005/0065760, titled "Method For Advising Patients Concerning Doses Of Insulin," and U.S. Pat. No. 6,589,229 titled "Wearable Self-Contained Drug Infusion Device," each of which is incorporated herein by reference in its entirety. The present invention contemplates the aforementioned pumps adapted for use in delivering the compositions of the invention. As a result, medication can be delivered to the user with precision and in an automated manner, without significant restriction on the user's mobility or lifestyle. The compact and portable nature of the pump and/or monitor affords a high degree of versatility in using the device. As a result, the ideal arrangement of the pump can vary widely, depending upon the user's size, activities, physical handicaps and/or personal preferences. In a specific embodiment, the pump includes an interface that facilitates the portability of the pump (e.g., by facilitating coupling to an ambulatory user). Typical interfaces include a clip, a strap, a clamp or a tape. These pumps and other similar or equivalent variants can be configured to dose a patient with the natriuretic peptides of the present invention.

In other embodiments, the infusion pump includes a control module connected to a fluid reservoir or an enclosed fluid reservoir may be disposed within the pump. The control module can include a pump mechanism for pumping fluid from the fluid reservoir to the patient. The control module includes a control system including a pump application program for providing a desired therapy and patient specific settings accessed by the pump application program to deliver the particular therapy desired to the patient. The control system can optionally be connected or coupled or directly joined to a network element, node or feature that is communication with a database. In one embodiment, a communications port is provided to transfer information to and from the drug pump. Other embodiments include a wireless monitor and connections as described in U.S. Patent App. Pub. No. 2010/0010330, the contents of which are incorporated herein by their entirety. The pump can further be programmable to allow for different pump application programs for pumping different therapies to a patient as described herein. In other configurations, the drug delivery or infusion pump of the present invention is implanted subcutaneously and consists of a pump unit with a drug reservoir and a flexible catheter through which the drug is delivered to the target tissue. The pump stores and releases prescribed amounts of medication via the catheter to achieve therapeutic drug levels either locally or systemically (depending upon the application). The center of the pump has a self-sealing access port covered by a septum such that a needle can be inserted percutaneously (through both the skin and the septum) to refill the pump with medication as required.

The continuous pumps of the invention can be powered by gas or other driving means and can be designed to dispense drugs under pressure as a continual dosage at a preprogrammed, constant rate. The amount and rate of drug flow are regulated by the length of the catheter used, temperature, and are best implemented when unchanging, long-term drug delivery is required. The pumps of the invention preferably have few moving parts and require low power. Programmable pumps utilizing a battery-powered pump and a constant pressure reservoir to deliver drugs on a periodic basis can be programmed by the physician or by the patient. For a programmable infusion device, the drug may be delivered in small, discrete doses based on a programmed regimen, which can be altered according to an individual's clinical response. Programmable drug delivery pumps may be in communication with an external transmitter, which programs the prescribed dosing regimen, including the rate, time and amount of each dose, via low-frequency waves that are transmitted through the skin. In some embodiments, the infusion pump adjusts the infusion rate according to blood pressure measured by a non-invasive blood pressure measurement device and/or measured body weight. Many drug delivery devices, implants and pumps of various configurations, in addition to those described herein, have been developed and are embraced by the present invention.

In the pumps of the invention, the therapeutic agent can be pumped from a pump chamber and into a drug delivery device, which directs the therapeutic agent to the target site. The rate of delivery of the therapeutic agent from the pump is typically controlled by a processor according to instructions received from the programmer. This allows the pump to be used to deliver similar or different amounts of the therapeutic agent continuously, at specific times, or at set intervals between deliveries, thereby controlling the release rates to correspond with the desired targeted release rates. Typically, the pump is programmed to deliver a continuous or intermittent dose of a natriuretic peptide to prevent, or at least to minimize, fluctuations in natriuretic peptide serum or plasma level concentrations. Moreover, the implantable infusion pump can be configured or programmed to deliver the natriuretic peptide in a constant, regulated manner for extended periods to avoid undesirable variations in blood-level drug concentrations associated with intermittent systemic dosing. It is understood that constant and continuous dosing can lead to better symptom control and superior disease management, particularly in the case of sustained plasma concentration of a natriuretic peptide at a desired level. Other contemplated routes of delivery of the therapeutic agent include intramuscular, parenteral, intraperitoneal, transdermal, or systemic delivery. For example, a drug delivery device may be connected to the pump and tunneled under the skin to the intended delivery site in the body. Generally, a pump can be distinguished from other diffusion-based systems in that the primary driving force for delivery by pump is pressure difference rather than concentration difference of the drug between the therapeutic formulation and the surroundings. The pressure difference can be generated by pressurizing a drug reservoir, by osmotic action, or by direct mechanical actuation as described by U.S. Pat. App. Pub. 2009/0281528, and U.S. Pat. Nos. 6,629,954; and 6,800,071, all of which are incorporated herein by reference.

In other embodiments of the invention, the drug provisioning component can be a vascular access port for infusing the drug into patient. The vascular access port can be positioned subcutaneously underneath the skin, or percutaneously when the access part of the port is placed above the level of the skin. In another embodiment, the drug provisioning component is a direct delivery catheter system chronically inserted through a small incision into a vessel to deliver the natriuretic peptides of the invention. The surgical procedures to provide for such access are described in the art, for example, in U.S. Pat. App. Pub. 2010/0298901, the contents of which are incorporated herein by reference.

It will be appreciated that the clinical function of an implantable drug delivery device or pump depends upon the device, particularly the catheter, being able to effectively maintain intimate anatomical contact with the target tissue (e.g., the subdural space in the spinal cord, the arterial lumen, the peritoneum) and not become encapsulated or obstructed by scar tissue. In many instances when these devices are implanted in the body, they are subject to a "foreign body" response from the surrounding host tissues. The body recognizes the implanted device as foreign, which triggers an inflammatory response followed by encapsulation of the implant with fibrous connective tissue. Scarring (i.e., fibrosis) can also result from trauma to the anatomical structures and tissue surrounding the implant during implantation of the device. Hence, the present invention contemplates biocompatible coatings being disposed on the surface of the device to prevent or minimize undesirable scarring and inflammation. Such coatings are known in the art and can be employed in the present invention.

Pharmacokinetic Studies

The two major extravascular routes of administration are intramuscular (IM) and subcutaneous (SQ). In IM administration, the therapeutic agent is injected deep into skeletal muscle. IM administration is often preferred because of the sustained action it provides as compared to intravenous (IV) administration. In SQ administration, the therapeutic agent is administered beneath the skin and into subcutaneous tissue. In general, the absorption rate from SQ delivery is slower than from the intramuscular site. Hence, SQ administration may be better suited for long term therapy. However, tissue sites might be changed frequently to avoid local tissue damage and accumulation of unabsorbed drug. Further, SQ delivery often lowers the potency of a peptide or protein drug due to degradation or incomplete absorption. The major barrier to absorption from the intramuscular or subcutaneous sites is believed to be the capillary endothelial membrane or cell wall. Nonetheless, SQ delivery of a peptide or protein drug is one preferred embodiment, depending on the particular effect desired and the rate of absorption and/or degradation at the delivery site. Further, SQ delivery can have the benefit of achieving prolonged therapeutic effect.

The pharmacokinetic studies used to assess the systemic exposure of administered drugs and factors likely to affect this exposure are to be conducted as outlined herein. Known methods of obtaining pharmacokinetic data require time consuming laboratory experiments, and is intended to provide a clear and consistent picture from which accurate conclusions can be drawn. In an effort to provide clearer and consistent test results, the study of the invention is designed to isolate a single variable and use a placebo control group as a baseline from which the variable is measured. Observations from the trial are used to formulate conclusions from apparent differences between the control group and the test group. Given the complex and dynamic nature of the study, the results thereof are unexpected.

The statistical analysis of pharmacokinetic data of the study addresses time-dependent repeated measurements of drug of concentrations in various organs of the body, with the goal being to describe the time course and to determine clinically relevant parameters by modeling the organism through compartments and flow rates. The mathematical solution is a system of differential equations with an explicit solution for most of the one or two compartment models. Intrinsic pharmacokinetic parameters include area under the curve (AUC), clearance, distribution volume, half-time or half-life, elimination rates, minimum inhibitory concentrations, etc. Numerous computer programs for linear and simple non-linear regression methods are known and can be used in the present invention. For example, clearance measures the body's ability to eliminate a drug. It does not indicate how much drug is removed, but rather the volume of blood or plasma that would be completely cleared of the drug. Thus, clearance is expressed as a volume per unit time, or flow parameter.

The systems and methods of the invention produce or result in plasma concentration levels for the natriuretic peptide in the range from greater than 0 to 60 ng/ml, as represented by the range from n to (n+i), where $n=\{x\in \mathbb{R} \mid 0<x\leq 60\}$ and $i=\{y\in \mathbb{R} \mid 0\leq y\leq(60-n)\}$. Hence, where x=20, the lower bound of the range is 20 ng/ml, and the upper bound is from 20 to 60 ng/ml, where i ranges from 0 to 20 ng/ml, so that the following ranges of concentration values are provided: 20 ng/ml, 20-21, 20-22, 20-23, . . . , 20-60 ng/ml. It will be understood that the plasma concentration values may be in the following non-limiting ranges from about 1-1, 1-2 ng/ml, 1-5, 1-10, 5-10, 10-20, 10-30, 10-60, 20-60, etc., and that any value from greater than 0 to 60 ng/ml is contemplated by the invention. In any embodiment, the systems and methods of the invention produce or result in plasma concentration levels for the natriuretic peptide in the range from greater than 0 to 40 ng/ml, as represented by the range from n to (n+i), where $n=\{x\in \mathbb{R} \mid 0<x\leq 40\}$ and $i=\{y\in \mathbb{R} \mathbb{R} \mid 0\leq y\leq(40-n)\}$.

One preferred plasma concentration range is from 10 to 20 ng/ml, as described by the range where n represents the lower bound for the range and (n+i) represents the upper bound, according to the following formulae: $n=\{x\in \mathbb{R} \mid 10\leq x\leq 20\}$, and $i=\{y\in \mathbb{R} \mid 0\leq y\leq(20-n)\}$.

In one embodiment, the natriuretic peptides can be subcutaneously infused at a dose to maintain a plasma level that is not greater than the plasma level reached during either the subcutaneous bolus or 1 hour IV infusion determinable by patient body weight. The pharmacokinetic model of the vessel dilator peptide for an 85 kg subject is shown in FIG. 1. FIG. 1 shows the pharmacokinetic model of the subcutaneous injection as compared to an estimated model of the equivalent IV dosage. As shown in the graph, the peak concentration reached in the plasma is slightly higher in the IV infusion model, but the area under the curve for the two methods of delivery are similar. For example, as shown above in FIG. 1, an 85 kg subject receiving a bolus dose of 0.51 mg would reach a peak plasma level from about 8 μg/L. Using the same pharmacokinetic model used to derive FIG. 1, a continuous infusion from about 200 μg/hr is calculated to lead to steady state concentrations of about 7.8 μg/L. The area under the curve (AUC) calculation shows that the total AUC on a daily basis is about 5 times as large as for the single bolus injection, but the peak height (Cmax) is the same as the bolus injection and IV infusion. The rate of administration contemplated by the invention is in the range from 10 to 150 ng/kg·min, such as 10 ng/kg·min, 10-125, 20-125, and 50-125 ng/kg·min. The rates of administration can be further expressed as the range from n to (n+i) ng/kg·min, where $n=\{x\in \mathbb{R} \mid 10\leq x\leq 300\}$, and $i=\{y\in \mathbb{R} \mid 0\leq y\leq(300-n)\}$, so that any value from 10 to 150 is contemplated by the invention. The rates of administration can also be expressed as the range from n to (n+ng/kg·min, where $n=\{x\in \mathbb{R} \mid 10\leq x\leq 150\}$, and $i=\{y\in \mathbb{R} \mid 0\leq y\leq(150-n)\}$, so that any value from 10 to 150 is contemplated by the invention.

In another embodiment, the atrial natriuretic peptides can be subcutaneously infused for 4 hours on and 8 hours off, repeating for 3 days, at rates corresponding to the same Cmax as observed in the first study. This can generate an AUC that is approximately two times that of the single bolus injection but is comparable to an IV infusion AUC, considering that the IV infusion is to be given at 12 hour intervals.

In yet another embodiment, dosing can occur continuously at a rate that would match the AUC of a bolus subcutaneous injection. This can be accomplished where the total amount of natriuretic peptide infused can be reduced or the time frame can be limited similar to the second scenario. If infusion is performed continuously while maintaining the AUC of the single bolus injection, then it may only be possible to achieve steady state levels of the peptide of between 1 and 1.5 μg/L. It is expected that this level will produce only minimal biological efficacy. Alternatively, infusion may be performed for 2 hours on then 10 hours off, or following a similar schedule.

In some embodiments, the method may further comprise monitoring one or more physiologic parameters of the patient. In other embodiments, the method further comprises creating a patient-specific dose-response database using data collected from the patient, evaluating the data in the database to maintain a plasma level of the natriuretic peptide in the patient within a specified mean steady state concentration range, and continuously monitoring patient data and updating the instructions, if necessary. The monitoring means and control elements can be in communication with the drug provisioning component to provide instructions as needed to either deliver drug.

To maintain a plasma concentration of the natriuretic peptides within a specified range, a control module that controls or provides controlling instructions to the pump can be configured for use in the invention. The control module can adjust a dosing schedule and/or calculate a new dosing schedule using signals from the patient. In one embodiment, a control module includes an outer housing containing within the control system and pump mechanism with an input module to permit entry of information into the pump.

The control module can further contain a communications port to allow communication with pump from an external device located either locally or remotely relative to pump. An external power supply port allows for connection of an external power supply to operate pump, or, in the case of an implantable pump, a receiver that can convert radio waves into power and store the received energy into a capacitor, and then perform a voltage boost to supply the system components with a regulated voltage. Further, memory configured either internally or externally can store various programs and data related to the operation of the pump. The memory is coupled to microprocessor, which, in turn, runs the desired operating programs which control operation of pump mechanism. Access to the microprocessor is provided through communications port or by other communication links such as infrared telemetry. Information programmed into memory instructs information to be transmitted or received via communications port or via infrared telemetry or other wireless means know to those of skill in the art. This feature allows information being received via communications port from an external device to control pump. This feature also allows for the downloading of any or all information from memory to an external device.

The control unit of the medical system of the invention can regulate the selective release of the natriuretic peptide to maintain a mean steady state concentration using data obtained from the patient. The control unit may further contain computer memory, and the control unit, using the computer memory and processor, may further compile and store a database containing data collected from the patient and also compute a dosing schedule that makes up a part of the therapeutic regimen.

Calculating dosing instructions used in the methods and systems described herein may consist of administering a test dose of the natriuretic peptide to the patient and then observing a concentration of circulating natriuretic peptide in the serum of the patient that results from the test dose. The concentration is then used to design a patient-specific therapeutic regimen that includes administering the natriuretic peptide to the patient subcutaneously using a continuous infusion apparatus in an amount sufficient to maintain circulating levels of the natriuretic peptide in the desired range for in vivo concentration for a specific period of time.

One illustrative embodiment of the invention includes a method of using a patient-specific regimen responsiveness profile obtained from a patient having kidney disease alone, heart failure alone, or kidney disease with concomitant heart failure to design a patient-specific therapeutic regimen. Embodiments of this method comprise administering at least one therapeutic agent, e.g., a natriuretic peptide, to the patient as a test dose (optionally, a dose that is a part of a first therapeutic regimen) and then obtaining pharmacokinetic or pharmacodynamic parameters from the patient to observe a patient-specific response to the test dose. Generally, pharmacokinetic or pharmacodynamic parameters obtained consist of a concentration of the natriuretic peptide in the plasma of the patient that results from the test dose. In this embodiment of the invention, practitioners can then use the pharmacokinetic or pharmacodynamic parameters obtained to observe a patient-specific response to the test dose, and the observed response is then used to create a patient-specific regimen responsiveness profile. This profile necessarily takes into account a variety of physiologic parameters observed in the patient. The patient-specific regimen responsiveness profile is then used to design a patent-specific therapeutic regimen. Once a therapeutic regimen is selected and administered, practitioners can then obtain or modify a patient-specific regimen responsiveness profile that results from the administration of this therapeutic regimen. The patient-specific regimen responsiveness profile can then be used to design further patient-specific therapeutic regimens.

It will be apparent to one skilled in the art that various combinations and/or modifications and variations can be made in such therapeutic regimens depending upon the various physiological parameters observed in the patient. For example, the therapeutic regimen calculated using the systems and methods of the invention may be based on any relevant biological parameter, such as the body weight of a patient. Moreover, features illustrated or described as being part of one embodiment may be used on another embodiment to yield a still further embodiment.

EXAMPLE 1

Intravenous (IV) Infusion of Vessel Dilator (VD) Peptide

Figure 3:
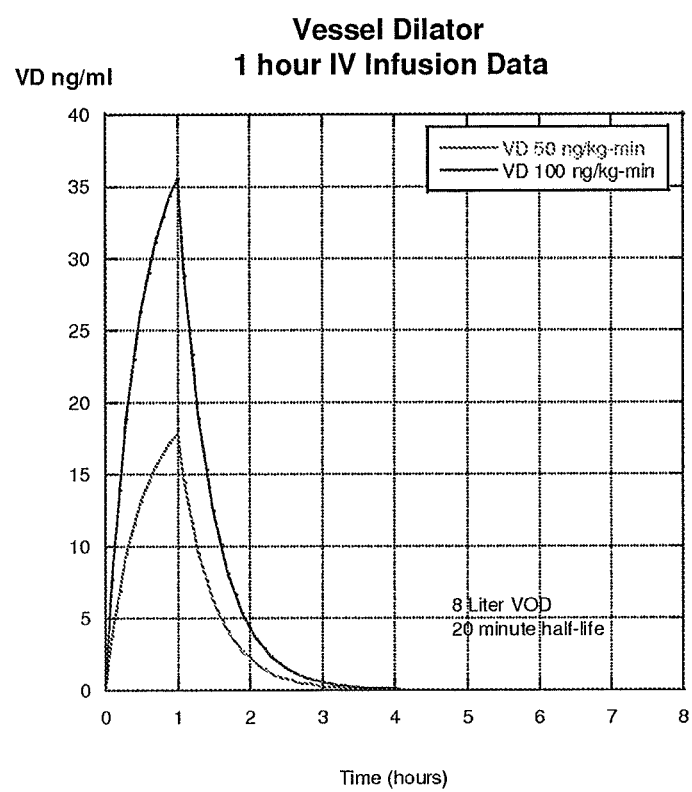
FIG. 3 shows the pharmacokinetic model for IV infusion at two different dosages.

A study can be performed examining the pharmacokinetics and pharmacodynamics of the vessel dilator (VD) peptide following intravenous (IV) infusion lasting 1 hour. The half life of the VD peptide for this route of administration is estimated to be about 20 minutes. Subjects are divided into two dose groups: (1) 50 ng/kg·min infusion rate and (2) 100 ng/kg-min infusion rate. For an 85 kg subject, the total dose delivered at 50 ng/kg·min is 255 μg, and at 100 ng/kg·min, the total dose delivered is 510 μg. The pharmacokinetic model for this IV infusion is shown in FIG. 3. As shown in the graph, the peak plasma levels reached are 17.7 and 35.5 ng/ml for the 50 and 100 ng/kg-min doses, respectively.

Administration of the peptide can be varied to achieve different models of exposure of the patient to the peptide. For example, in certain embodiment models, an 85 kg subject can receive a bolus dose of peptide to reach a peak plasma level of about 8 μg/L. In certain other embodiments, an 85 kg subject can receive a continuous infusion over a daily period of 200 μg/hr to achieve a comparable peak plasma level of about 7.8 μg/L. However, continuous infusion over the course of a day period will result in a total exposure of the peptide (i.e., AUC) of about 5 times the level a single bolus injection of 0.51 mg of peptide. It is presumed that the 85 kg subject has a half-life for subcutaneous absorption for the peptide of 20 minutes and a half-life for elimination of the peptide of 2 hours along with a distribution of the peptide in a volume equivalent to 60% of body weight.

Subjects can vary in the absorption parameters in particular. In certain embodiments, a subject can exhibit a half-life for absorption from 0 to 60 minutes depending upon the physiological state of the subject. The absorption half-life can be described by the range of n to (n+i) minutes, where $n=\{x \in \mathbb{R} \mid 0<x \leq (60-n)\}$, and $i=\{y \in \mathbb{R} \mid 0 \leq y \leq (60-n)\}$. In certain other embodiments, a subject can exhibit a half-life for subcutaneous absorption of the peptide from 0 to about 30 minutes, from 0 to about 5 minutes, from about 15 to 25 minutes, and from about 15 to about 30 minutes, in addition to about 20 minutes.

Subjects can further vary in elimination parameters for removal of the peptide, depending upon the physiological state of the patient and other additional parameters. In certain embodiments, a subject can exhibit a half-life for elimination of the peptide from about 20 minutes to about 4 hours, from about 20 minutes to about 1 hour, from about 30 minutes to about 1.25 hours, from about 1 to about 3 hours or from about 20 minutes to 40 minutes. In a further embodiment, a subject can exhibit a half-life for elimination of the peptide from about 5 minutes to about 4 hours, as described by the range of n to (n+i) minutes, where n={x∈ ℝ |5≤x≤240} and i={y∈ℝ |0≤y≤(240-n)}.

An administration of the peptide can be performed to achieve similar peak plasma levels while limiting the total exposure of the peptide to the subject. In certain embodiments, a subcutaneous infusion can be performed over the course of 4 hours, followed by an 8 hour off period, and then followed by an additional 4 hours of subcutaneous infusion. This cycle can be repeated during the course of treatment. Using an administration rate of 200 µg per hour for the above-described 85 kg subject, a peak plasma concentration of about 8 µg/L can be reached. However, due to the intermittent 8 hour off periods, the total exposure of the peptide to the subject (i.e., AUC) will be only about twice that compared to a 0.51 mg single bolus injection over a daily period of infusion treatment.

In certain other embodiments, the total exposure of the subject to the peptide by subcutaneous infusion can be maintained at a level equivalent to a subcutaneous single bolus injection with 0.51 mg peptide. For example, if infusion is performed at a dosage rate such that a peak plasma level in the range of 1 to 1.5 µg/L is achieved, the total exposure to the subject can be limited to the same AUC as for a single bolus injection of 0.51 mg for the above-described 85 kg subject over a daily period of infusion treatment. In certain other embodiments, the subject can be infused to achieve a higher peak plasma concentration with extended off periods to limit AUC. For example, the subject can be infusion for 2 hour periods with intervening 10 hour off periods. Other lengths of infusion periods and off periods are possible to achieve desired characteristics.

The half-life for elimination of the peptide can have a noticeable effect on the pharmacokinetics exhibited for the peptides described herein. As discussed above, a subject can exhibit a half-life for elimination falling into one of several ranges. Half-life for elimination is believed to be impacted by the physiological state of the subject. This includes not only the weight, age, water-retention of the subject, but also the presence of specific disease states, including impairment of kidney function. A subject can have kidney impairment such that the glomerular filtration rate is less than about 60 mL/min/1.73 m², as represented by the range from n to (n+i) mL/min/1.73 m², where n={x∈ℝ |0<x≤60} and i={y∈ ℝ |0≤y≤(60-n)}. In certain other embodiments, a subject has a glomerular filtration rate less than about 15 mL/min/ 1.73 m² or in the range from 0 to about 60 mL/min/1.73 m². It is believed that subjects exhibiting impairment of kidney function and/or kidney disease may sometimes unexpectedly display a shorter half-life for elimination of natriuretic peptides compared to individuals not having kidney disease. That is, it is expected that subjects having kidney disease would have a longer half-life for elimination of the peptide compared with the average healthy individual not displaying impairment of kidney function.

In certain embodiments, the steady state plasma concentration achieved by infusion of the peptide by subcutaneous infusion is from about 20 to about 40 µg/L, as previously described. In certain other embodiments, the steady state plasma concentration achieved by subcutaneous infusion can be from about 10 to about 60 µg/L, about 10 to about 20 µg/L, from about 20 to about 30 µg/L, from about 20 to about 35 µg/L, from about 25 to about 40 µg/L, from about 30 to about 40 µg/L or from about 5 to about 40 µg/L. In additional embodiments, the steady state plasma concentration achieved by subcutaneous infusion can be from about 0 to about 40 µg/L, from about 0.5 to about 40 µg/L, from about 2 to about 40 ttg/L or from about 5 to about 40 µg/L.

The steady state plasma concentration achieved by infusion is influenced by the rate of infusion or dosing administered to the subject. In certain embodiments, the peptide is administered by infusion at a rate from about 10 to about 150 ng/kg·min based upon the subject's body weight. In certain other embodiments, the peptide is administered by infusion at a rate from about 10 to about 300 ng/kg·min, about 20 to about 125 ng/kg·min, from about 50 to about 125 ng/kg·min, from about 90 to about 110 ng/kg·min in addition to about 95 to about 100 ng/kg·min. In additional certain other embodiments, the peptide is administered by infusion at a rate of infusion based upon subject's weight from about 10 to 300 ng/kg·min, from about 10 to 250 ng/kg·min, or from about 10 to about 200 ng/kg·min. In certain additional embodiments, the natriuretic peptide is administered to the subject at a rate from any one of about 25 to about 145 ng/kg·min, about 30 to about 140 ng/kg·min, about 35 to about 125 ng/kg·min, about 50 to about 120 ng/kg·min, about 65 to about 115 ng/kg·min, and about 85 to about 110 ng/kg·min of the subject's body weight.

One of the factors affecting the amount of peptide infused into the subject is the subject's body weight. However, it should be noted that weight is not the only factor affecting the amount of peptide administered by infusion. Specifically, the subject's physiological state also influences the amount of peptide required. However, subjects typically require a subcutaneous infusion dose from about 51 to about 765 µg/hr in certain embodiments. In other embodiments, a subject can require a subcutaneous infusion dose from about 75 to about 500 µg/hr, from about 100 to about 500 µg/hr or from about 125 to 450 µg/hr.

In certain other embodiments, from about 0.6 to about 9 µg of the natriuretic peptide is administered to the subject per kg of the subject's body weight in an hour time period. In certain additional embodiments, the natriuretic peptide is administered to the subject at a rate from about 1 to about 8 µg, from about 2 to about 5 µg, from about 3 to about 4 µg, from about 1 to about 7 µg, from about 3 to about 5 µg, from about 2 to about 6 µg, from about 7 to about 9 µg, or from about 8 to about 9 µg of the natriuretic peptide per kg of the subject's body weight in an hour time period.

EXAMPLE 2

Modeling Pharmacokinetics and Pharmacodynamics of Vessel Dilator (VD) Protein

Using an IV infusion model, a two-part study can be performed to determine the pharmacokinetics of subcutaneously delivered Vessel Dilator (VD) peptide and to establish a relationship between the pharmacokinetics of VD and the subsequent pharmacodynamics, particularly related to hemodynamics and kidney function. In a first part of the study, a number of subjects can be dosed subcutaneously with VD. A full range of noninvasive measurements can be obtained. The first study can thereby result in establishing pharmacokinetic parameters in the subjects at certain doses.

A second part of the study can be run on 16 subjects, all of whom are fitted with right heart catheters to measure hemodynamics. This stage can be run in two doses. The nominal doses can be chosen to mimic the peak plasma levels reached by IV infusion and subcutaneous (SQ) bolus administration of the first part of the study described herein. A first group of 8 subjects within the second part can be dosed at 250 µg/hour for 6 hours. This can lead to a steady state plasma concentration of about 10.0 ng/ml, which can be less than the peaks reached in either an IV infusion or SQ bolus study. A second set of 8 subjects in the second part of the study can be tested using a dose of 500 μg/hour for 6 hours.

After the first part is completed and the pharmacokinetic analysis completed, the second part can begin. The delay between the first and second parts should be no longer than one month.

The outline of the second part of the study is shown in Table 1.

TABLE 1

| Stage 2 | Day 1 | Day 2 |
|---|---|---|
| N = 8 | 250 ug/hr for 6 hours (1.5 mg total) | No drug |
| N = 8 | 500 ug/hr for 6 hours (3 mg total) | No Drug |
| Hemodynamics | Swan Ganz and non-invasive | Non-invasive |
| Kidney Function | Urine output, Na, lab panel | MGFR |

EXAMPLE 3

Determination of Pharmacokinetic Behavior of Vessel Dilator (VD) Peptide

An alternative study can be performed to establish a dosing for the VD peptide, where the VD peptide is detected in blood extracted from a subject by liquid chromatograph (LC)-mass spectrometry (MS) methods or LC-MS-MS methods. It is desired to study the pharmacokinetic behavior of VD by SQ administration at the lowest feasible range of doses while still allowing for adequate ability to detect VD peptide in the blood plasma.

Up to 18 subjects can be enrolled in the study, where the subjects can be divided into two groups with a goal of at least 8 evaluable subjects in each group. The first 8 subjects can be dosed for 6-12 hours by SQ infusion with VD peptide at a rate that will lead to a plasma concentration of 10 ng/mL above baseline, which is about half of the peak plasma concentration reached during a 1 hr IV infusion at 50 ng/kg·min. A second set of subjects can receive a higher dose for 6-12 hours by SQ infusion at a rate sufficient to result in a steady state plasma concentration of 20 ng/mL, which is about half of the peak plasma concentration reached during a 1 hr IV infusion at 100 ng/kg·min.

Those skilled in the art will readily understand that VD peptide is a natural hormone peptide derived from ANP, as discussed above. As such, subjects are expected to have a baseline endogenous plasma concentration of VD peptide. Administration of VD peptide by SQ infusion will increase the levels above the endogenous background level of VD in the subjects. The plasma concentrations for VD of 10 and 20 ng/mL are plasma concentrations reached in addition to the endogenous baseline concentration of VD in a particular subject. In the published literature, background plasma concentrations of VD peptide in heart failure patients are near 5 ng/ml. In kidney failure patients, concentrations significantly higher than these are measured, for example, baseline plasma concentrations of VD peptide for NYHA class IV patients and can be approximately 20 ng/ml.

The VD peptide will be administered by SQ infusion in sterile Elliott's Buffer B at 1 mg/ml using a Medtronic MiniMed Paradigm™ infusion pump system (Elliott's Buffer: 7300 mg NaCl, 1900 mg sodium bicarbonate, 800 mg dextrose, 300 mg $MgSO_4.7H_2O$, 300 mg KCl, 200 mg $CaCl_2.2H_2O$ and 200 mg sodium phosphate dibasic.$7H_2O$ per liter). All patients in the study can have GFR measured during the week prior to a clinic visit for the SQ administration of VD. Prior to administration of VD, routine laboratory measurements as well as non-invasive hemodynamics can be observed including estimates of ejection fraction by magnetic resonance imaging (MRI) and/or echocardiogram. Subject selection criteria are shown in Table 2.

TABLE 2

Patient Selection:

Inclusion Criteria:

a) Patients with a history of symptomatic congestive heart failure, with a left ventricular ejection fraction of ≤45% measured by echocardiogram or MRI (measurement 3-6 months prior to screening);
b) Brain Natriuretic Peptide (BNP) ≥100 pg/mL;
c) Signed Consent;
d) 18 years or older;
e) Non-pregnant females as evidenced by blood test or 2 consecutive urine tests;
f) eGFR greater ≥25 ml/min/1.73 m² (MDRD method) and less than 70 ml/min/1.73 m²;
g) Patients on a stable, background therapeutic doses of a beta-blocker, ACE-inhibitor or ARB, unless contraindicated and documented as such; and
h) Patients on a stable, background therapeutic dose of a diuretic and/or aldosterone receptor inhibitor (e.g. spironolactone) unless contraindicated and documented as such.

Exclusion criteria:

a) Evidence for Myocardial Infarction (MI) or high risk acute coronary syndrome within past 6 weeks, as determined by creatinine kinase (CK)/creatinine kinase a muscle-brain isoenzyme (CK-MB) being 3 times upper limit of normal (as defined by Institute of Medical and Veterinary Science (IMVS)) or elevation of troponin T at baseline >0.1;
b) Evidence of Acute MI (ST elevation and/or elevation of Troponin T), as determined by a 12-lead EKG;
c) Hypotension (Systolic Blood Pressure (SBP) <90 mmHg), cardiogenic shock, volume depletion or any other clinical condition that would contraindicate administration of an agent with potent vasodilator effects;
d) Persistent, uncontrolled hypertension (SBP >180 mm Hg);
e) Presence of any Cardiac Magnetic Resonance (CMR) contra-indication (includes Permanent Pacemaker (PPM), cerebral aneurysm clips);
f) Congenital heart defects;

TABLE 2-continued

Patient Selection:

g) Cardiac surgery within past 4 weeks;
h) Severe valvular heart disease: Aortic stenosis (AS), Ideopathic hypertrophic subaortic stenosis (IHSS), Hypertrpohic Obstructive Cardiomyopathy (HOCM), acute Aortic Incompetence (AI) and Mitral Regurgitation (MR);
i) History of cerebrovascular accident (within past 4 weeks);
j) Acute or chronic active infection, including pneumonia and urinary tract infection;
k) Significant renal impairment as determined by a creatinine clearance of <25 ml/min/1.73 m$^2$ (MDRD); and
(l) Prior participation in any other clinical trial within past 30 days.

The primary outcome measurement of the study will be the safety and tolerability of the various doses of VD. Efficacy outcome data to be measured include:

1. Change in cardiac index (CI). This will be measured via trans-thoracic echocardiogram (11 h) at the end of days 1, and 2 post initiation of administration of vessel dilator for both stages of the trial.

2. Change in systemic arterial blood pressure, via automated sphygmomanometer during the trial for both Stages.

3. Change in Ejection Fraction (EF) by Cardiac Magnetic Resonance Imaging (CMR) between groups measured at day 6+/−24 hours after administration of VD peptide for all subjects compared to baseline measurements.

4. Change in Ejection Fraction (EF) by Trans-Thoracic Echocardiogram (TTE) within the groups after 6 days (+/−24 hr) following administration of VD peptide;

5. Change in Borg dyspnea index at 6 days (+/−24 hr) following administration of VD peptide.

6. Change in kidney markers (EGFR, creatinine, Cystatin C, NGAL, and KIM-1) during the study and at 6 days (+/−24 hr) following administration of VD peptide. Additionally, changes in inulin/iothalamate/iohexol clearance between by day 2 following administration of VD peptide will be evaluated.

7. Readmission rates for Major Adverse Cardiac Events (All-cause Death, Myocardial Infarction (MI), Cerebral Vascular Incidence (CVA), and Recurrent Congestive Heart Failure (CHF)), as assessed by patient phone contact and review of relevant case report forms.

Once the pharmacokinetic parameters have been estimated from the analytical data obtained in the study, a dosing protocol can be designed. Continuous SQ infusion of VD peptide can be designed to yield steady state plasma concentrations that are less than levels reached during 1-hour IV infusion administrations that are current clinical practice. The SQ infusion protocol for VD peptide will be determined to yield plasma levels of 10 and 20 ng/ml above baseline, as described above. Data that will be obtained from LC-MS or LC-MS-MS assays will be used to calculate the appropriate SQ infusion dosing regimen.

The primary safety endpoints are drug related adverse events. The primary efficacy endpoints are changes in GFR as well as changes in blood pressure and cardiac output measured non-invasively.

The secondary efficacy endpoints to be analyzed include:
1. Cardiac Index and change from baseline;
2. Change in vascular resistance from baseline;
3. Change in blood pressure (systolic and diastolic) during dosing; and
4. Change in indirect kidney markers between baseline and 2 after administration of VD peptide.

Statistical analysis of the secondary endpoints will be correlated to the AUC, Cmax, and dose.

EXAMPLE 4

Modeling Pharmacokinetics and Pharmacodynamics of Vessel Dilator (VD) Protein

Figure 4:
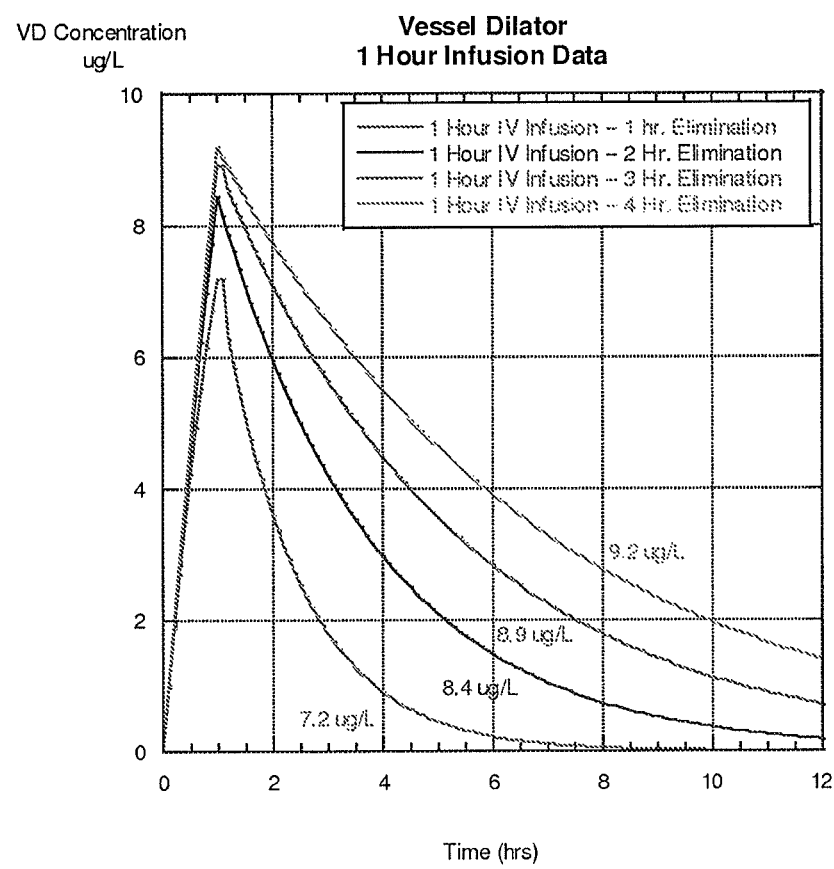
FIG. 4 shows the pharmacokinetic model for IV infusion with varying half-life for elimination.

Subjects exhibiting a change in the half-life for elimination of the peptide can have different exposure profiles to the peptide resulting from the same dosing regimen. FIG. 4 shows a model 85 kg subject having a 60% volume of distribution for the peptide based upon the subject's weight. This 85 kg subject can be dosed by IV infusion over the course of one hour at a rate of 8.5 µg/min for a total dose of peptide of 0.51 mg. As shown in FIG. 4, a one hour infusion at this dosing rate is not sufficient to achieve steady state; however, large differences in peak plasma level for the peptide and total exposure of the peptide (AUC) results from changes in half-life for elimination of the peptide. As indicated in FIG. 4, based upon a half-life for elimination raging from 1 hour to 4 hours, the peak plasma concentration ranges from about 9.2 µg/L for a subject having a half-life of 4 hours to 7.2 µg/L for a subject having a half-life of 1 hour. FIG. 4 also shows that the AUC is changed based upon the half-life for elimination of the peptide although the dosing regime is the same for all subjects.

Figure 5:
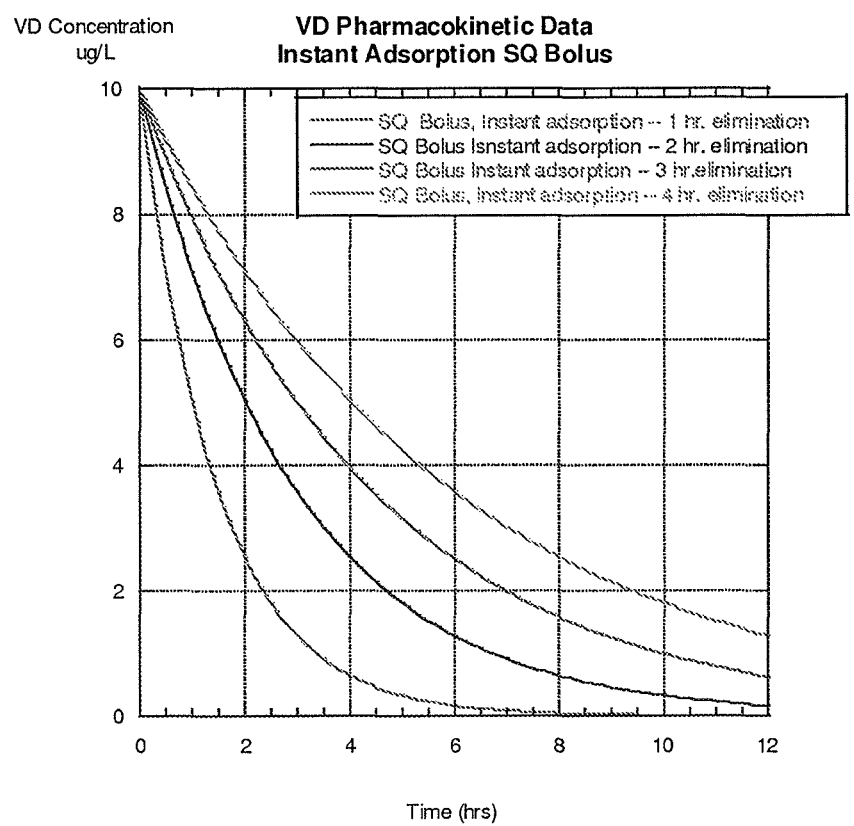
FIG. 5 shows the pharmacokinetic model for single bolus subcutaneous injections with instantaneous absorption and varying half-life for elimination.

FIG. 5 shows that a large change in exposure to the peptide results from subcutaneous bolus injection of the peptide based upon changing half-life for elimination of the peptide. In FIG. 5, the above-described 85 kg subject as in FIG. 4 is modeled receiving a subcutaneous bolus dose of 0.51 mg of the peptide. For simplicity, the 85 kg subject is modeled as absorbing the single bolus dose instantaneously resulting in the same peak plasma level of the peptide regardless of the half-life for elimination of the peptide. As can be seen, large changes in the AUC and hence the total exposure to the peptide are predicted to occur, although the same single bolus dose is administered with the same maximum plasma level for the peptide. A subject displaying a 4 hour half-life for elimination of the peptide is expected to experience a greater exposure to the peptide compared to a subject displaying a 1 hour half-life due to the presence of elevated plasma levels over an extended period of time.

Figure 6:
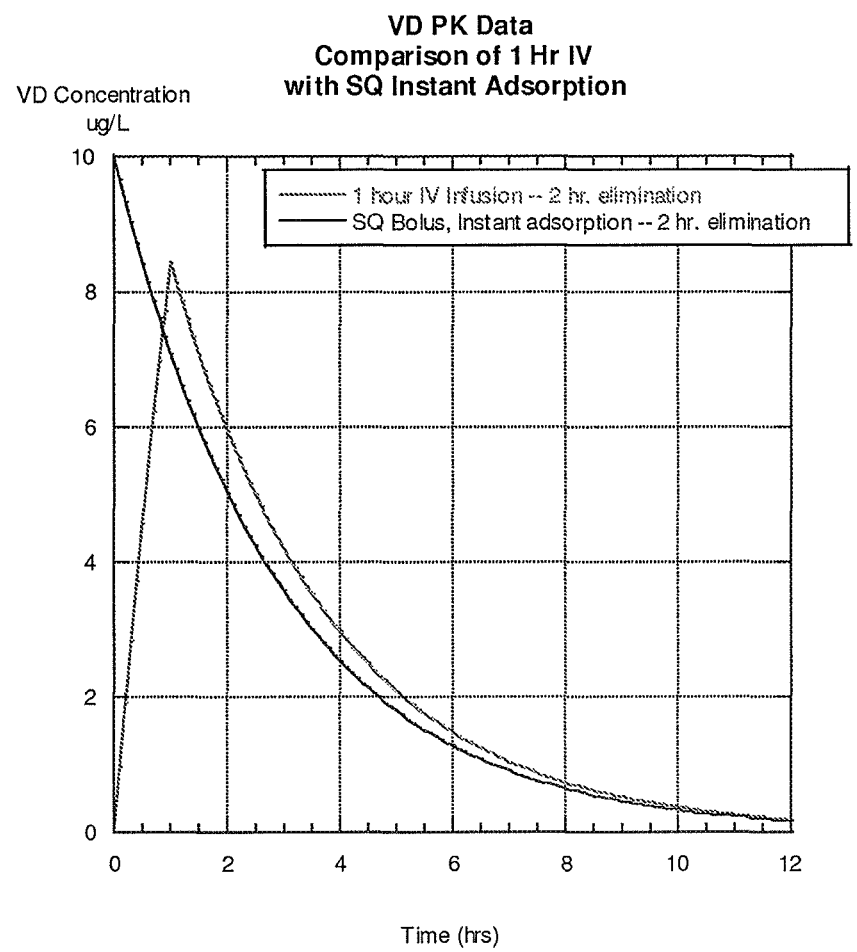
FIG. 6 shows the pharmacokinetic model for IV infusion as compared to an estimated model of the equivalent dosage by single subcutaneous bolus.

As shown in FIG. 6, total exposure to the peptide is also predicted to vary depending upon route of administration even if the subject is otherwise identical. Again, FIG. 6 shows the above described 85 kg subject having a 60% volume of distribution based upon the subject's weight. FIG. 6 shows a modeled plasma concentration for the peptide (y-axis) for the 85 kg subject based upon route of administration of a 0.51 mg dose of the peptide for the subject having a half-life for elimination of the peptide of 2 hours. One plot in FIG. 6 models an IV infusion over the course of 1 hour at a rate of 8.5 µg/min. The other plot in FIG. 6 models a subcutaneous single bolus of 0.51 mg of peptide having instantaneous absorption. The peak plasma levels for the peptide are not largely varied. However, the AUC for the single bolus injection is about 40% larger than for the one-hour infusion.

Figure 7:
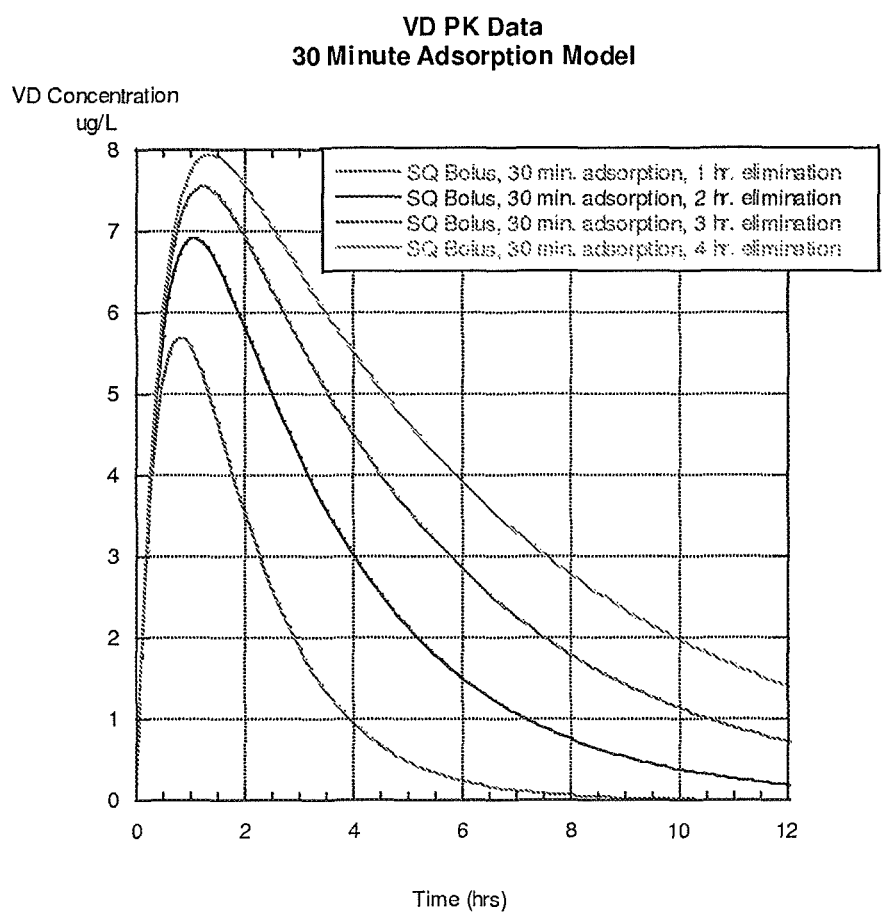
FIG. 7 shows the pharmacokinetic model for single bolus subcutaneous injections with varying half-life for elimination combined with a half-life for absorption of the administered peptide.

FIG. 5 demonstrates the change in predicted AUC based upon a single subcutaneous bolus injection having instant absorption depending on the half-life for elimination of the peptide. FIG. 7 shows that the behavior in regarding a change in predicted AUC persists where the single bolus injection is not adsorbed instantaneously. In FIG. 7, the above described 85 kg subject is modeled having a half-life for absorption of the peptide of 30 minutes. A subject displaying a 4 hour half-life for elimination of the peptide is expected to experience a greater exposure to the peptide compared to a subject displaying a 1 hour half-life due to the presence of elevated plasma levels over an extended period of time. In addition, a significant change in peak plasma concentration of peptide is predicted due to the delay in absorption of the peptide into the plasma.

Figure 8:
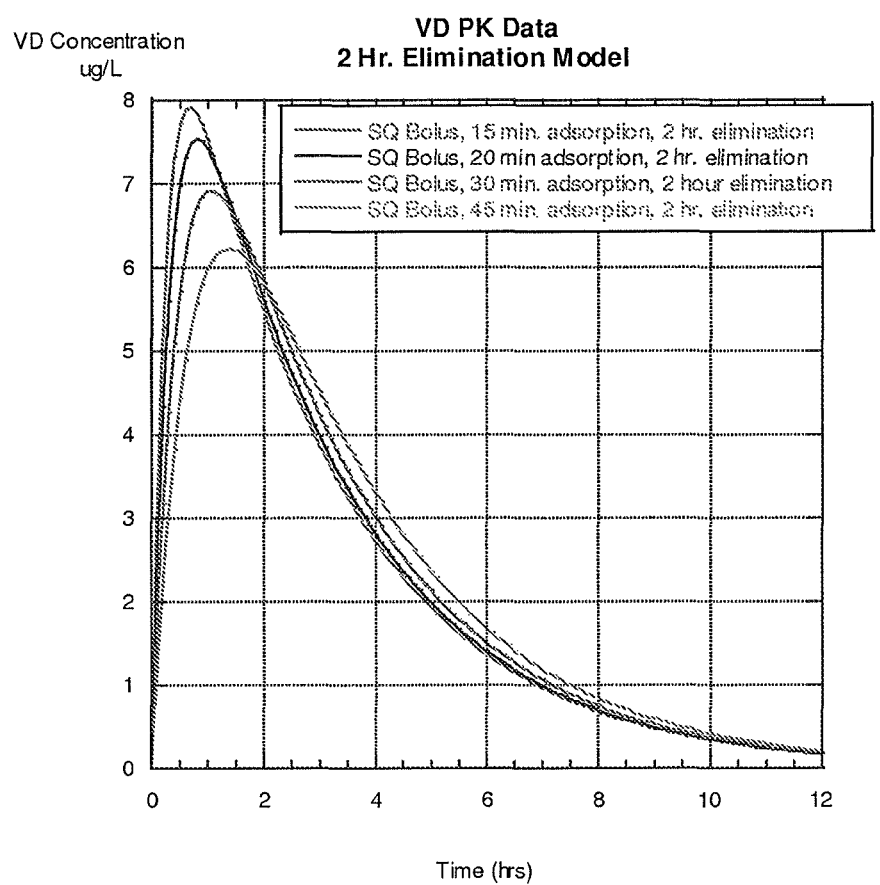
FIG. 8 shows the pharmacokinetic model for single bolus subcutaneous injections with varying half-life for absorption.

As discussed in regard to FIG. 7, the presence of a half-life for absorption of the peptide is predicted to have an effect on peak plasma concentration of the peptide depending upon the half-life for elimination of the peptide. In FIG. 8, a change in the half-life for absorption of the peptide is predicted to have an effect on peak plasma concentration without a change in the half-life for elimination of the peptide. FIG. 8 models the above described 85 kg subject having a 60% volume of distribution for the peptide based upon the subject's body weight. The half-life for elimination of peptide exhibited by the subject is fixed at 2 hours. As shown in FIG. 8, a short half-life for absorption (15 minutes) of the peptide results in a peak plasma concentration of about 8 µg/L. A longer half-life for absorption (45 minutes) of the peptide results in a peak plasma concentration of about 6.2 µg/L. As can further be seen in FIG. 8, a change in AUC is observed based upon the peak plasma level for the peptide.

Figure 9:
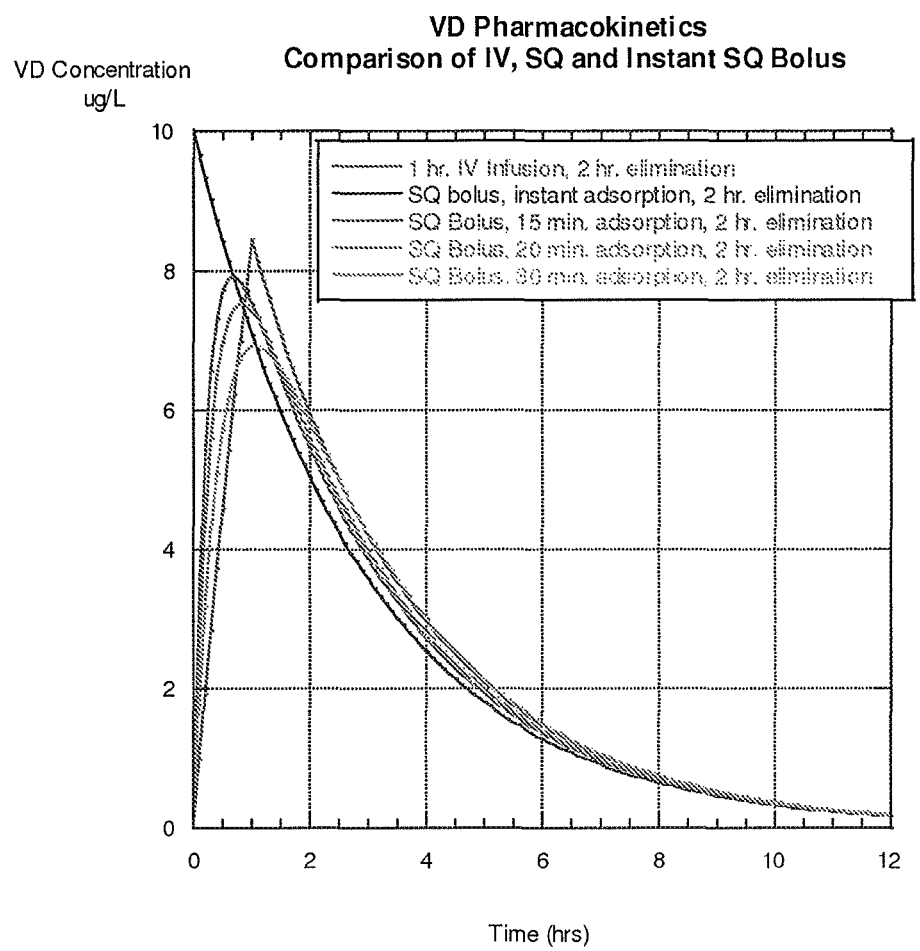
FIG. 9 shows the pharmacokinetic model for IV infusion as compared to an estimated model of the equivalent dosage by single subcutaneous bolus with varying half-life for absorption.
Figure 10:
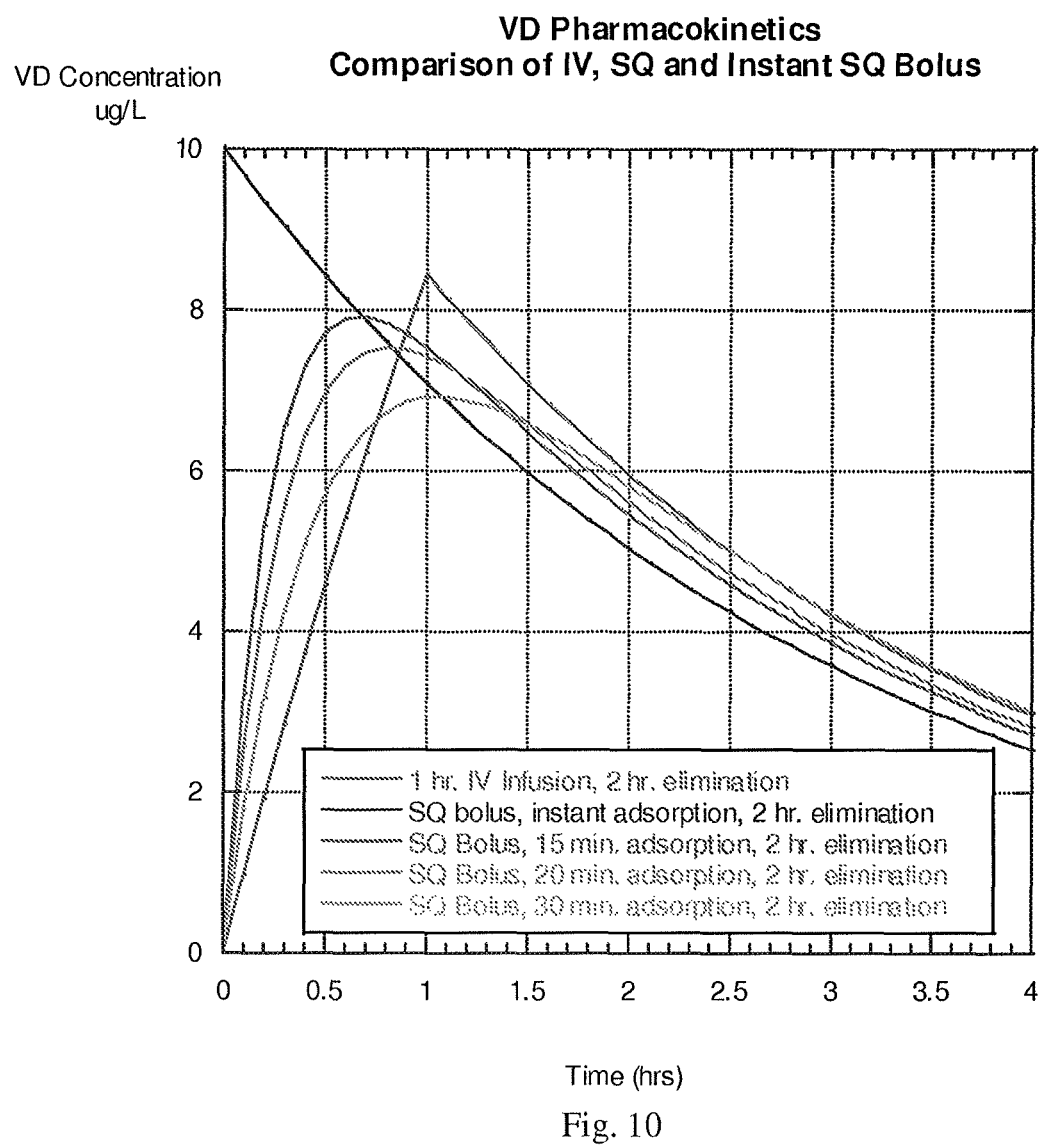
FIG. 10 shows a detailed view of the pharmacokinetic model from FIG. 9.

In FIG. 9, the behavior of the peptide through different routes of administration is compared. The above-described 85 kg subject having a 60% volume of distribution based upon subject weight is modeled in FIG. 9. The 85 kg subject has a half-life for elimination of the peptide of 2 hours. A total of five curves are modeled in FIG. 9 that vary by route of administration and/or half-life for subcutaneous absorption of the peptide. The 85 kg subject is modeled with either a one hour IV infusion of 0.51 mg of total peptide or a single subcutaneous bolus of 0.51 mg of peptide. The rate of absorption for the single bolus injections is modeled ranging from instantaneous absorption to a half-life for absorption of 30 minutes. As can be seen in FIG. 9, the one-hour IV infusion is predicted to have a higher peak plasma level than a subcutaneous bolus having a half-life longer than instantaneous. As such, it is predicted that subcutaneous administration can limit undesirable spikes in peak plasma level while still maintaining a satisfactory AUC for the subject's total exposure to the peptide. FIG. 10 shows the same model plotted with a smaller time scale on the x-axis to show detail.

The steady state level of the peptide achieved by subcutaneous infusion can vary depending upon the volume of distribution (VOD) displayed by a particular subject for the peptide. The VOD for particular subjects can vary considerably based upon the particular physiologic condition of the subject. In particular, kidney impairment can have an impact of the VOD displayed by a particular subject. The VOD for a subject contemplated by the invention ranges from about 5 to about 65 L, as represented by the range from n to (n+i) liters, where n={x∈ℝ |5≤x≤65} and i={y∈ℝ |0≤y≤(65−n)}. In certain other embodiments, a subject has a VOD for the peptide from about 10 to about 25 L, from about 5 to about 15 L, from about 30 to about 65 L or from about 45 to about 65 L.

VOD has an effect on the clearance of the peptide from the plasma of the subject. Clearance is a measure of the time needed to clear the peptide from a given amount of the VOD for the peptide and is reported in units of L/hr. In some embodiments, clearance ranges up to about 137 L/hr, as represented by the range from n to (n+i) L/hr, where n={x∈ ℝ |0<x≤137} and i={y∈ℝ |0≤y≤(137−n)}. In certain embodiments, the subject exhibits a clearance for the peptide from about 0.85 to about 137 L/hr. In certain other embodiments, the subject exhibits a clearance for the peptide from about 5 to about 100 L/hr, from about 10 to about 90 L/hr or from about 20 to about 90 L/hr.

Pharmacodynamic Studies

SQ administration of a peptide or protein drug requires satisfactory absorption to obtain a therapeutic effect. In particular, SQ administration should demonstrate an ability for the peptide or protein drug to be absorbed through capillary endothelial membranes and cell walls to enter the circulation. VD was administered by SQ infusion to canines to demonstrate the ability of VD to have a pharmacological effect over a long-term course of treatment.

EXAMPLE 5

Toxicology Study of VD in Canines

VD was administered to canines via a subcutaneous delivery route. The dosing was performed at a high level to assess the toxicity of VD and to determine if a lethal dosing amount of the VD can be reached by subcutaneous administration.

VD was administered subcutaneously to canines using a Medtronic Paradigm® infusion pump (model MMT772) over a period of 5 days. VD was obtained as an acetate salt (VD-acetate) from Bachem (lot 2502022) and prepared in Tris/Glycerin/m-cresol buffer at a concentration of 15 mg/mL. The Tris/Glycerin/m-cresol buffer was prepared by mixing 16.0 g glycerol, 6.05 g tris-(hydroxymethyl)-aminomethane ("Tris"), 2.50 g meta cresol in a 1.00 L volumetric flask. Approximately 900 mL nanopure water was added to the volumetric flask and the mixture was magnetically stirred to reach complete dissolution. 4 normal hydrochloric acid was used to adjust pH to 7:3 at 25° C.

VD was administered to one male and one female beagle canine at varying dosing amounts. Each canine received a first dosage level for 5 consecutive days followed by a 2-day washout period. Then, the same canines received a second, higher dosage level for an additional 5 consecutive days.

Prior to the beginning of dosing with VD (Day 0), the canines were placed in a sling and the dose site on the dorsolateral thorax was shaved. The shaved area was swabbed with 70% isopropyl alcohol and allowed to dry. DuraPrep™ (3M) was then applied and allowed to dry for 3 minutes. The catheter of the infusion set (Medtronic Silhouette Paradigm® Infusion Set MMT-378) was placed subcutaneously and perpendicular to the spine, and attached to the skin. The extension set was then attached to a previously weighed reservoir filled with VD at a concentration of 15 mg/mL in the Tris/Glycerin/m-cresol buffer. The reservoir was inserted into the pump located in a jacket pocket and dosing was commenced. The jacket was then secured and a collar was placed on each canine. Every day during the 5-day period, the reservoirs were exchanged with new filled reservoirs at approximately the same time each day.

At the end of the first 5-day dosing period, the infusion sets and jackets were removed, the area where the catheter was placed was marked, and the animals were allowed a 2-day washout period prior to the next treatment. For the next treatment at the second dosing amount, a new infusion site was chosen on the skin, and the pump was prepared as before.

The daily dosage level during the first 5-day period (Group 1) was 1.44 mg/(kg·day) (or 1000 ng/(kg·min)) for each canine corresponding with a dosage volume of 0.096 ml/(kg·day). The total dose delivered to each canine over the first 5-day period was 7.20 mg/kg. Canines in Group 1 did not show clinical signs of toxicity during the first 5 days of drug administration. Following the 2-day washout period, the daily dosage level was increased to 2.88 mg/(kg·day) (or 2000 ng/(kg·min)) for each canine corresponding with a dosage volume of 0.192 ml/(kg·day) during the second 5-day period (Group 2). The total dose delivered to each canine over the second 5-day period was 14.4 mg/kg. The dosing for Group 1 and Group 2 is summarized in Table 3 below.

TABLE 3

VD Dosing for Canines

| Treatment | | Dosage Level[a] | Dosage Volume | Number of Animals[b] | |
|---|---|---|---|---|---|
| Group | Number | (mg/kg/day) | (mL/kg/day) | Males | Females |
| 1 | Vessel Dilator | 1.44 | 0.096 | 1 | 1 |
| 2 | Vessel Dilator | 2.88 | 0.192 | 1 | 1 |

[a]Total doses of 7.20 and 14.4 mg/kg were administered by constant-rate infusion for 5 days at rates of 1.44 or 2.88 mg/kg/day, respectively.
[b]The same animals were used for both dose levels with an approximate 2 day washout between dosages.

All animals were observed twice daily during the first and second 5-day periods for mortality and moribund appearance. Clinical examinations were also performed daily for the animals after dosing began. Detailed physical examinations were conducted on Day 0 prior to dosing and on study Day 5 after the pumps and jackets were removed from the canines. Individual body weights were recorded twice weekly during a 7-day pretest period, on study Day 0 prior to dosing and study Day 5 after the pumps and jackets were removed from the canines. Body weights and body weight changes were calculated for the corresponding intervals. Individual food consumption was recorded daily during the pretest period and throughout the study.

Blood samples for determination of plasma drug concentration were collected at 2, 4, 24 and 96 hours after the beginning of infusion, immediately prior to the end of infusion on Day 5, and 0.5, 1, 1.5, and 2 hours after the end of dosing. Blood was collected via the jugular vein into chilled tubes containing $K_3$-EDTA. Plasma was isolated in a refrigerated centrifuge, placed into prepared tubes containing 1.8 TIU (trypsin inhibitory units) of aprotinin, and stored frozen at approximately −70° C. within approximately 1 hour of blood collection. Plasma was analyzed for the concentration of Vessel Dilator using a radioimmunoassay with an approximate lower limit of quantization (LLOQ) of 1 ng/ml. Both canines survived to the scheduled study termination without appreciable adverse effects on weight, food consumption or behavior. Potential VD administrated-related clinical observations noted for the male canine at both the 1.44 and 2.88 mg/(kg·day) dosage levels included reddened ears and/or reddened gums. These observations were considered non-adverse and were noted as early as 4 days after the start Of the first 5-day period (Day 3 of the study). Observations of reddened ears persisted to the beginning of the second treatment following the 2-day washout period. There were no effects on body weight for both canines. There were no effects related to food consumption for both canines.

Figures 11A, 11B:
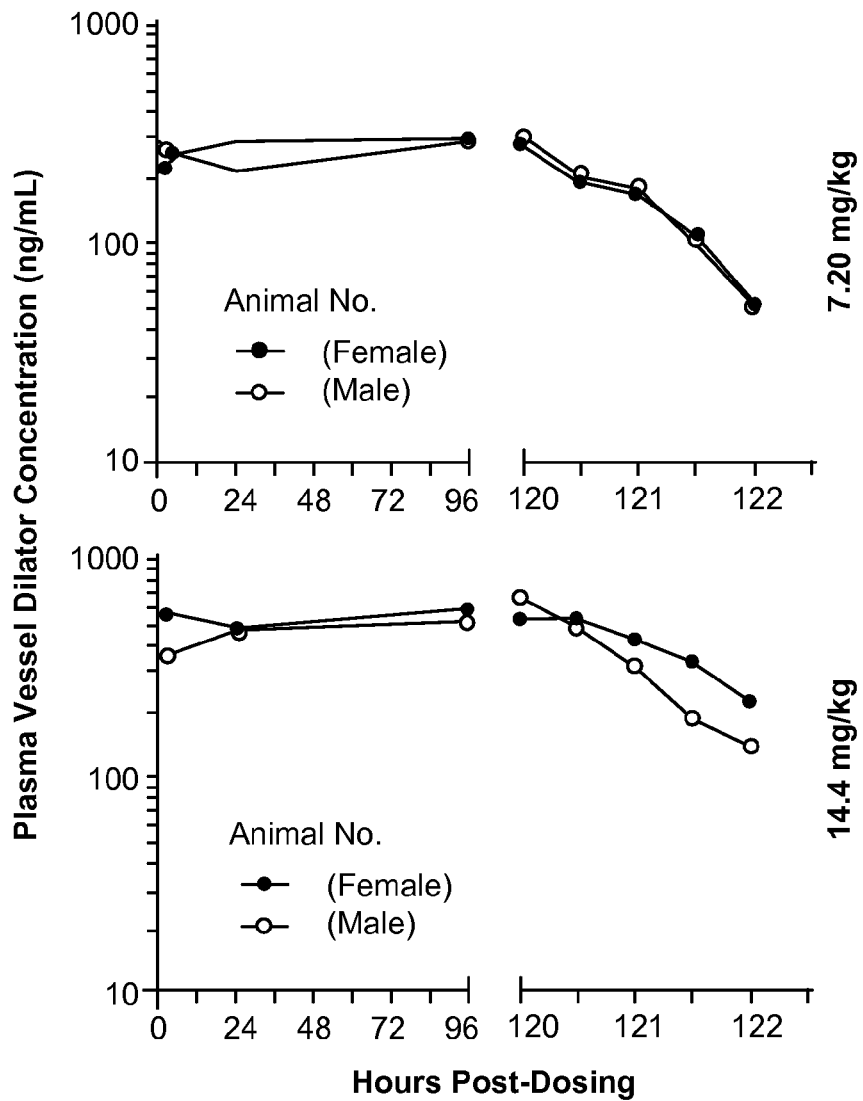
FIGS. 11A and 11B show the measured plasma concentration of VD in canines at a total dose of 7.2 mg/kg and 14.4 mg/kg, respectively.

Subcutaneous administration of VD by constant-rate subcutaneous infusion over each 5-day period resulted in systemic exposure to VD, as measured by $AUC_\tau$ and $C_{max}$, that increased proportionally with the increase in dosage from Group 1 to Group 2 for both genders. Exposure was similar between genders, except that $T_{max}$ for both dosages was 120 hours after the start of the infusion for the male canine and about 96 hours after the start of infusion for the female canine. Plasma concentrations of VD fluctuated by approximately 30% for both genders at the 1.44 mg/(kg·day) dosing rate and by 61% for the male canine and 18.5% for the female canine at the 2.88 mg/(kg·day) dosing rate. Following the end of the infusion, plasma concentrations of VD rapidly decreased through the last sample collection 2 hours after the end of the infusion. The calculated half-life for elimination of Vessel Dilator in plasma ranged from 0.7 to 1.2 hours. These values were regarded as approximations because they were greater than ½ of the 1.5 h sampling interval. The rate of elimination appeared slightly slower for females at the 14.4 mg/kg total dose over 5 days than for females at the 7.20 mg/kg total dose over 5 days. FIG. 11 shows the measured plasma concentrations for VD for both canines at the 7.2 mg/kg dosing (FIG. 11A) and the 14.4 mg/kg dosing (FIG. 11B). The break in the x-axis on FIG. 11 represents the before- and after-dosing time periods.

Figure 12A:
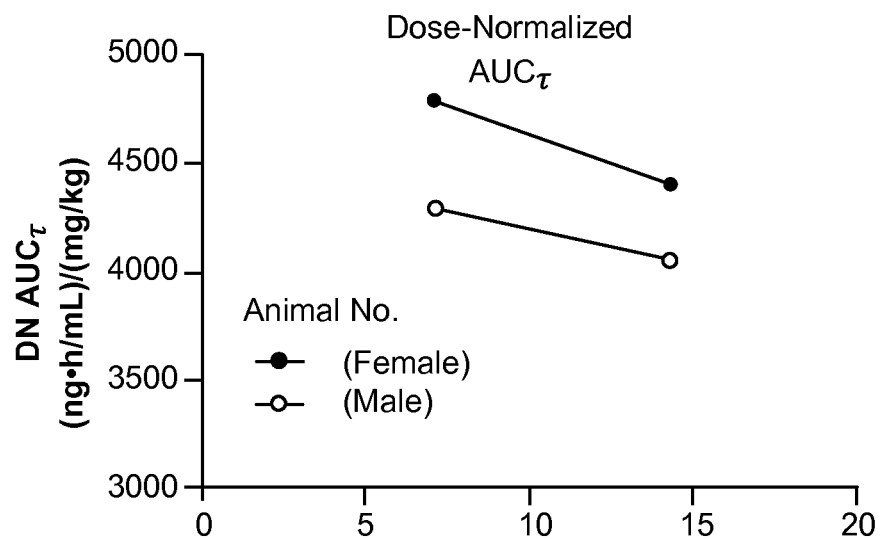
FIGS. 12A and 12B show dose normalized AUCτ and dose normalized $C_{max}$ for observed plasma concentration of VD in canines.
Figure 12B:
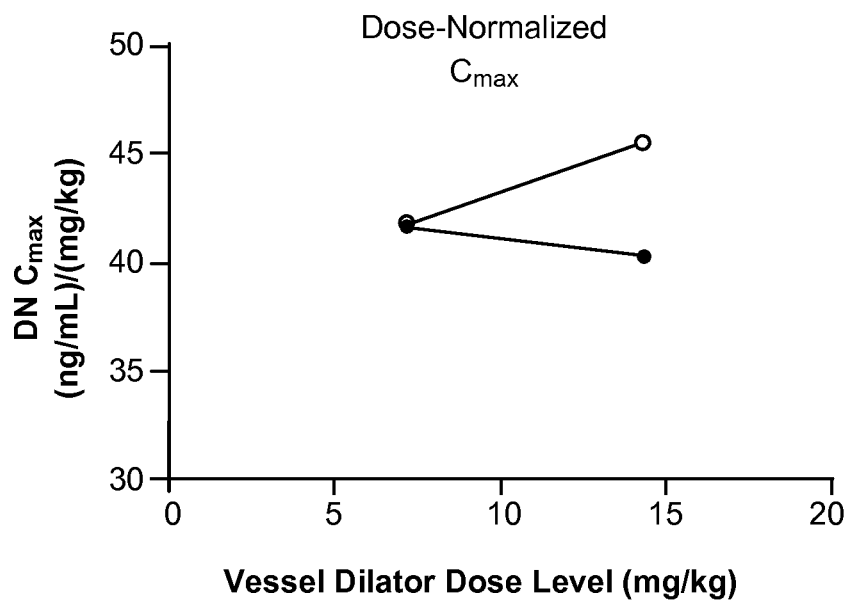

The pharmacokinetic parameters extracted from the graphs on FIG. 11 are presented below in Table 4. As discussed, $T_{max}$ (time to highest observed plasma concentration) was at the end of the 5-day dosing periods for the male canine, which implies that plasma concentration was still increasing at the conclusion of dosing. AUC is presented for the 120-hour dosing period ($AUC_\tau$) and including two hours following the stoppage of dosing ($AUC_{last}$) in Table 4. Dose normalized $AUC_\tau$ is shown in FIG. 12A and dose normalized $C_{max}$ is shown in FIG. 12B. Dose normalized parameters are calculated by dividing the parameter by the total dose amount over the 5-day dosing period in units of mg/kg to allow for direct comparison of across dosing amounts.

TABLE 4

Parameters for VD in canines

| Parameter | 1.44 mg/kg/day (7.20 mg/kg) | | | 2.88 mg/kg/day (14.4 mg/kg) | | |
|---|---|---|---|---|---|---|
| | Male | Female | Mean | Male | Female | Mean |
| $C_{min}$ (ng/mL) | 213 | 222 | 218 | 358 | 482 | 420 |
| $C_{max}$ (ng/mL) | 300 | 300 | 300 | 653 | 579 | 616 |
| $C_{avg}$ (ng/mL) | 257 | 287 | 272 | 485 | 527 | 506 |
| % Fluctuation | 33.9 | 27.1 | 30.5 | 60.8 | 18.5 | 397 |
| $AUG_\tau$ (ng·h/mL)* | 30850 | 34422 | 32636 | 58195 | 63299 | 60747 |
| $AUC_{last}$ (ng·h/mL)* | 31171 | 34732 | 32952 | 58865 | 64109 | 61487 |
| $T_{max}$ | 120 | 96 | 108 | 120 | 96 | 108 |
| $t_{1/2}$ (h) | 0.735 | 0.801† | 0.735 | 0.793† | 1.21† | NA |
| Dose-Normalized: | | | | | | |
| $C_{max}$ | 41.7 | 41.6 | 41.7 | 45.4 | 40.2 | 42.8 |
| $AUC_\tau$ | 4285 | 4781 | 4533 | 4041 | 4396 | 3219 |

Units for dose-normalized $AUC_\tau$ and Cmax are (ng h/mL)/(mg/kg) and (ng/mL)/(mg/kg), respectively.
*The dosing interval (τ) was considered to be 120 hours. $AUC_{last}$ included data collected through 122 hours.
†Half-life value greater than ½ the 1.5-hour interval used for calculation and therefore considered approximate and excluded from the mean.
NA = Not applicable.

Based on the above-presented results, continuous subcutaneous infusion of VD can be performed to achieve high blood serum levels with high tolerance and no noticeable toxicological effects. The 1.44 mg/(kg·day) dosing regimen is expected to be significantly above clinical use levels for humans. As such, it is expected that subcutaneous administration of VD can be performed with almost no adverse toxicological effects and allow for flexibility in designing dosing regimens. A maximum tolerated dose was not determined, where such a dose would result in Cmax above 655 or 579 ng/mL and mean AUC' values above 58,195 or 63,299 ng·hr/mL for the 2.88 mg/(kg·day) observed for the male canine and female canine, respectively.

EXAMPLE 6

Toxicology Study Of Vd In Rats

VD was administered to a rat model via a subcutaneous delivery route to assess the toxicity of VD and to determine if a lethal dosing amount of the VD can be reached by subcutaneous administration. As noted above, a maximum tolerated or lethal dosing amount was not observed for canines.

VD-acetate (Bachem lot 2502022) was prepared in the Tris/Glycerin/m-cresol buffer at a concentration of 3 mg/mL or 15 mg/mL. The VD solution was administered continuously by subcutaneous infusion using Alzet® (Durect Corp.) osmotic minipumps (model 2002) over a period of 5 days to 3 study groups, where each study group (Groups 1-3) contained 3 male and 3 female Sprague Dawley rats.

The continuous subcutaneous delivery dose for Group 1 was calibrated to yield an administration of approximately 100 ng/(kg·min) of VD, which is in the range of a dosing regimen useful for clinical use in humans. The rats in Group 1 had one Alzet pump implanted with an infusion rate of 0.5 μl/hour for the 3 mg/mL VD solution, which resulted in actual mean weight-based doses of 0.132 and 0.163 mg/(kg·day) (or ~92 ng/(kg·min) and ~113 ng/(kg·min)), for males and females, respectively. However, an estimated body weight of 250 g was used for all animals (males and females) for reporting pharmacokinetic and toxicological calculations; therefore, the estimated daily dose is reported as 0.144 mg/kg·day (or 100 ng/(kg·min)) for all animals in Group 1, and the total dose delivered to each animal over the 5-day period was 0.180 mg.

The continuous subcutaneous delivery dose for Group 2 was calibrated to yield an administration of approximately 1000 ng/(kg·min) of VD, which is 10-fold higher than for Group 1. Each rat in Group 2 each had two Alzet pumps implanted to have a combined infusion rate was 1.0 μL/hr of the 15 mg/mL VD solution. The resulting actual mean weight-based doses were 1.026 and 1.629 mg/(kg·day) for males and females, respectively. For the pharmacokinetic calculations, an estimated body weight of 280 g was used for all animals (males and females); therefore, the estimated daily dose was reported as 1.29 mg/(kg·day) (or ~896 ng/(kg·min)) for all animals in Group 2, and the total dose delivered to each animal over the 5 day period was 1.8 mg.

The continuous subcutaneous delivery dose for Group 3 was calibrated to yield an administration of approximately 2000 ng/(kg·min). Each rat each had four Alzet pumps implanted for a combined infusion rate was 2.0 μL/hr of the 15 mg/mL VD solution. The resulting actual mean weight-based doses were 1.870 and 3.303 mg/(kg·day) for males and females. For pharmacokinetic calculations, an estimated body weight of 300 g was used for all animals (males and females); therefore the estimated daily dose was reported as 2.4 mg/(kg·day) (or (or ~1667 ng/(kg·min)) for all animals in Group 3, and the total dose delivered to each animal for the 5 day period was 3.6 mg. The dosing for Groups 1-3 is summarized in Table 5.

TABLE 5

VD Dosing for Rats

| Group Number | Infusion Rate[a] (µL/hour) | Formulation Concentration (mg/mL) | Dose Rate (mg/hour) | Total Administered Dose (mg) | Approximate Daily Dosage[b] (mg/kg/day) | Number of Animals | |
|---|---|---|---|---|---|---|---|
| | | | | | | Males | Females |
| 1 | 0.5 | 3.0 | 0.0015 | 0.180 | 0.144 | 3 | 3 |
| 2 | 1.0 | 15 | 0.015 | 1.80 | 1.29 | 3 | 3 |
| 3 | 2.0 | 15 | 0.030 | 3.60 | 2.40 | 3 | 3 |

[a]Individual pumps had a rate of 0.5 µL/hour each; 1, 2, or 4 pumps were used for Groups 1, 2, or 3, respectively.
[b]Based on approximate body weight of 250, 280, and 300 g for Groups 1, 2, and 3, respectively. Actual mean daily dosages for Group 1 were 0.132 and 0.163 mg/kg/day for males and females, respectively.
Actual mean dosages for Group 2 were 1.03 and 1.63 mg/kg/day for males and females, respectively.
Actual mean dosages for Group 3 were 1.87 and 3.30 mg/kg/day for males and females, respectively.

All animals in Groups 1-3 were observed twice daily for mortality and moribund appearance during the 5-day dosing period and during an at least 16-day pretest period. Clinical examinations were performed daily for all animals following surgery to implant the Alzet pumps. Detailed physical examinations were conducted on all animals approximately weekly during a pretest period of at least 16 days, prior to beginning dosing (Day 0), and on Day 5 prior to euthanasia. Individual body weights were recorded at least weekly during the pretest period, on Day 0 prior to dosing, and on Day 5 prior to euthanasia. Individual food consumption was recorded approximately weekly during the pretest period, on Day 0 prior to dosing, and on Day 5 prior to euthanasia. Blood samples for determination of plasma drug concentration were collected from all animals at approximately 4, 8, and 24 hours after pump implantation on Day 0 and immediately prior to euthanasia on Day 5 (120 hours after the start of dosing). Blood was collected via the retro-orbital sinus from animals anesthetized with isoflurane into chilled tubes containing $K_3$-EDTA. Following the final blood collection, the animals were euthanized and discarded. Plasma was isolated in a refrigerated centrifuge, placed into prepared tubes containing 0.6 TIU of aprotinin, and stored frozen at approximately −70° C. within approximately 1 hour of blood collection. Plasma was analyzed for the concentration of Vessel Dilator using radioimmunoassay with an approximate lower limit of quantization (LLOQ) of 1 ng/ml.

None of the animals in Groups 1-3 showed clinical signs of toxicity during the 5 days of drug administration and all animals survived until euthanasia. There were no remarkable clinical observations, effects on body weight gain or effects on food consumption during the 5-day dosing period.

Table 6 summarizes the exposure to VD in terms of $C_{max}$, $C_{avg}$, and $AUC_\tau$ as the total dose level is varied from 0.180 to 3.60 mg total dose for the 5-day period. The increase in exposure to VD ($AUC_\tau$ and $C_{avg}$) was generally proportional to the increases in VD dose for both genders. For example, a 20-fold increase in dose (from 0.180 to 3.60 mg over the 5 days) resulted in an increase of approximately 13- to 17-fold for mean $AUC_\tau$, $C_{avg}$, and $C_{max}$ in males and approximately 16- to 18-fold for the same parameters in females. When normalized to body weight, approximate actual doses were 0.163, 1.63, and 3.30 mg/(kg·day) for females and 0.132, 1.03, and 1.87 mg/(kg·day) for males, for Groups 1-3 respectively. This represented a 20-fold increase in dose for females between Groups 1 and 3 and a 14-fold increase in for males between Groups 1 and 3.

Figure 13A:
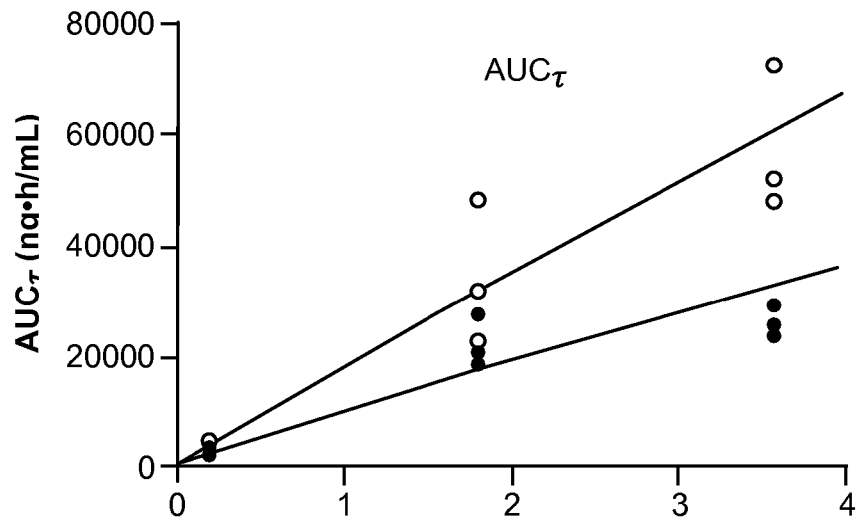
FIGS. 13A and 13B show the dose dependence of AUCτ and $C_{avg}$ for observed plasma concentration of VD observed in rats.
Figure 13B:
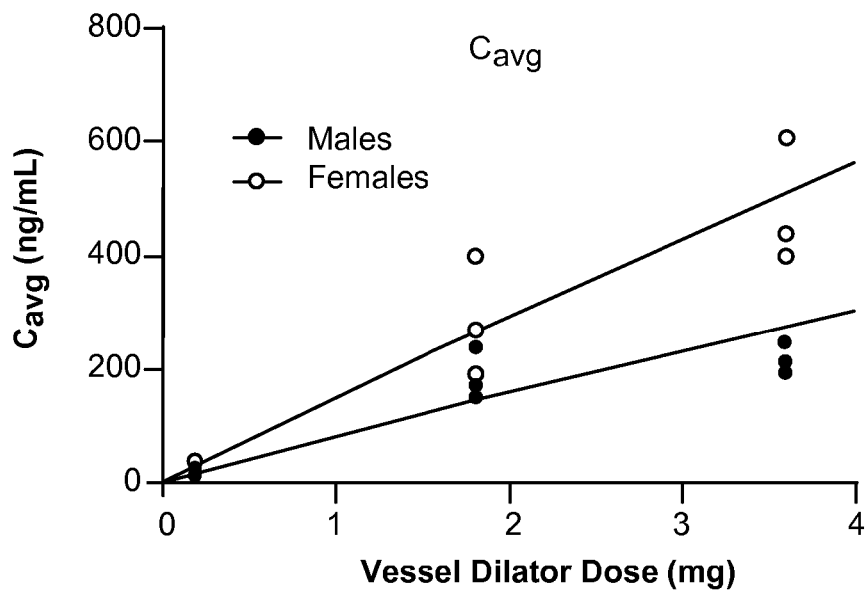
Figure 14:
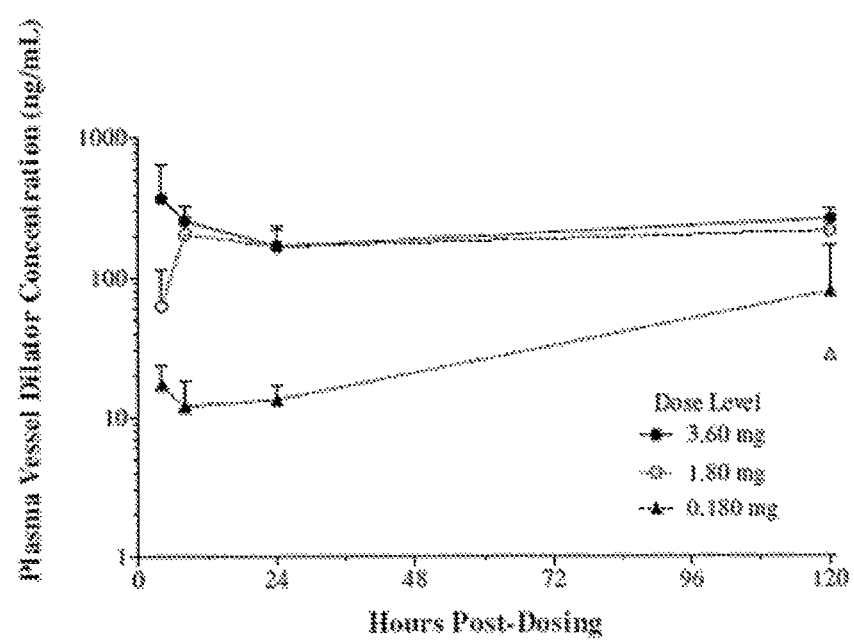
FIG. 14 shows the time-dependent observation of plasma concentration for VD in male rats receiving continuous subcutaneous administration of VD. The open triangle represents a suspected outlier measurement excluded from the trend line.
Figure 15:
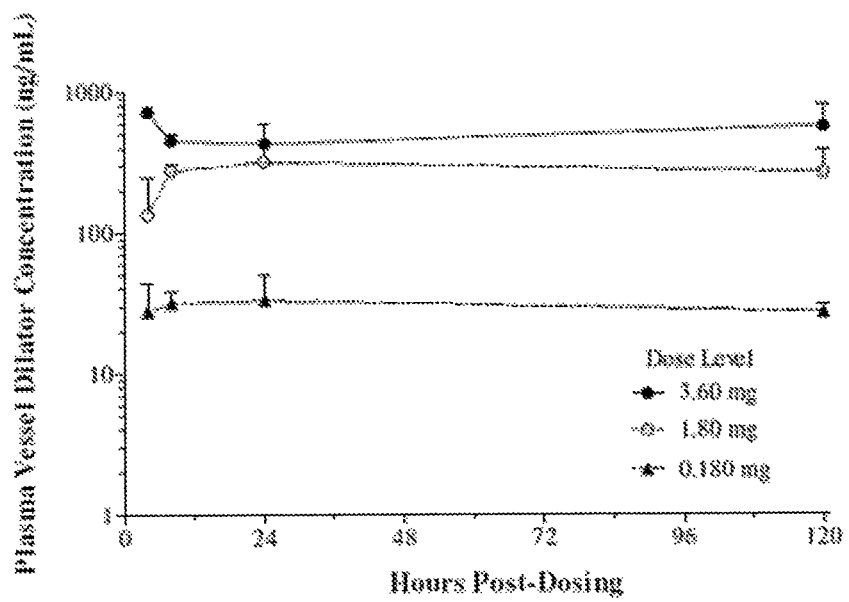
FIG. 15 shows the time-dependent observation of plasma concentration for VD in female rats receiving continuous subcutaneous administration of VD.

As shown on Table 6, exposure to VD in terms of $AUC_\tau$ was up to 2-fold greater for Group 3 females compared to Group 3 males. However, $AUC_\tau$ normalized to account for the weight difference between males and females resulted in a similar exposure between genders. FIG. 13 shows the change in $AUC_\tau$ (FIG. 13A) and $C_{avg}$ (FIG. 13B) for male and female in response to increased dose of VD. The time at which maximum VD plasma concentration occurred (Tmax) could not be determined accurately due to the large sampling intervals. Tables 7 and 8 show the mean measured plasma concentration of VD for male and female rats, respectively. The data for Table 7 and 8 is shown in graphical form in FIGS. 14 and 15.

TABLE 6

Parameters for VD in rats

| | Males | | | Females | | |
|---|---|---|---|---|---|---|
| Dose (mg): | 0.180† | 1.80 | 3.60 | 0.180 | 1.80 | 3.60 |
| Parameter (Units) | | | | | | |
| $C_{min}$ (ng/mL) | 10.2 (10.2) | 62.3 | 167 | 19.5 | 135 | 342 |
| $C_{max}$ (ng/mL) | 79.6 (25.1) | 233 | 431 | 41.7 | 355 | 739 |
| $C_{avg}$ (ng/mL) | 39.1 (16.7) | 182 | 215 | 29.4 | 281 | 475 |
| % Fluctuation (%) | 149 (83.6) | 98.4 | 126 | 70.1 | 84.7 | 89.9 |
| $AUC_\tau$* (ng · h/mL) | 4689 (2005) | 21806 | 25789 | 3533 | 33691 | 56956 |
| $T_{max}$** (h) | 81.3 (42.7) | 82.7 | 44.0 | 12.0 | 503 | 42.7 |
| | (4-120) | (8-120) | (4-120) | (4-24) | (8-120) | (4-120) |

TABLE 6-continued

Parameters for VD in rats

| | Males | | | Females | | |
|---|---|---|---|---|---|---|
| Dose (mg): | 0.180† | 1.80 | 3.60 | 0.180 | 1.80 | 3.60 |
| Dose-Normalized: | | | | | | |
| $C_{avg}$ ((ng/mL)/mg) | 217 (928) | 101 | 59.7 | 164 | 156 | 132 |
| $AUC_\tau$ ((ng · h/mL)/mg) | 26049 (11141) | 12114 | 7164 | 19629 | 18717 | 15821 |

*The dosing interval (τ) was considered to be 120 hours. $AUC_{last} = AUC_\tau$ for all animals.
**For $T_{max}$, range is presented parenthetically.
†For males at 0.180 mg, 1 sample collected from a male at 120 hours post-dosing (concentration of 180 ng/mL) was a suspected outlier.; the mean data excluding this sample are presented in parentheses, except for the range of $T_{max}$, which was 4-120 hours.

TABLE 7

Mean concentrations of vessel dilator in plasma of male rats following continuous subcutaneous infusion of 0.180, 1.80, or 3.60 mg vessel dilator.

| Hours Post-Dosing | 0.180 mg* Mean ± SD (ng/mL) | | 1.80 mg Mean ± SD (ng/mL) | | 3.60 mg Mean ± SD (ng/mL) | |
|---|---|---|---|---|---|---|
| 4 | 17.1 | 6.21 | 62.3 | 49.6 | 370 | 277 |
| 8 | 11.9 | 6.14 | 204 | 47.3 | 255 | 72.9 |
| 24 | 13.3 | 3.33 | 167 | 53.1 | 168 | 64.1 |
| 120 | 78.6 (27.7) | 88.4 | 214 | 41.8 | 261 | 43.6 |

N=3.
All times are reported from the start of the infusion, which lasted approximately 120 hours.
*Data in parentheses represents mean value excluding suspected outlier

TABLE 8

Mean concentrations of vessel dilator in plasma of female rats following continuous subcutaneous infusion of 0.180, 1.80, or 3.60 mg vessel dilator.

| Hours Post-Dosing | 0.180 mg Mean ± SD (ng/mL) | | 1.80 mg Mean ± SD (ng/mL) | | 3.60 mg Mean ± SD (ng/mL) | |
|---|---|---|---|---|---|---|
| 4 | 27.5 | 16.4 | 135 | 113 | 725 | 18.5 |
| 8 | 31.6 | 6.53 | 275 | 29.4 | 454 | 49.9 |
| 24 | 33.2 | 17.4 | 320 | 130 | 427 | 174 |
| 120 | 27.1 | 3.94 | 265 | 123 | 567 | 234 |

N = 3.
All times we reported from the start of the infusion, which lasted approximately 120 hours.

As discussed above, even high doses of VD delivered by subcutaneous infusion up to 2000 ng/(kg·min) failed to produce any manifest adverse toxicological effects. VD administered by continuous subcutaneous infusion via Alzet osmotic pumps over a period of 5 days to Sprague Dawley rats at 1.144, 1.29 and 2.4 mg/(kg·day) was well tolerated at all dosage levels. Due to a lack of any toxicological effects, a maximum tolerated dose was not determined. At the highest dosage level, mean $C_{max}$ values were 431 and 739 ng/ml and mean $AUC_\tau$ values were 25,789 and 56,956 ng·hr/mL for males and females, respectively. Normalized by weight, exposure as measured by $AUC_\tau$ between genders was similar.

EXAMPLE 7

Pharmacodynamic Study of VD in Canines

A pharmaceutical formulation of VD was prepared in a Tris buffer. 16.0 g glycerol, 6.05 g tris-(hydroxymethyl)-aminomethane ("Tris"), 2.50 g meta cresol were mixed in a 1.00 L volumetric flask. Approximately 900 mL nanopure water was added to the volumetric flask and the mixture was magnetically stirred to reach complete dissolution. 4 normal hydrochloric acid was used to adjust pH to 7.3 at 25° C. Then, the flask was filled to 1 L mark with nanopure water. The pH was rechecked and verified to be 7.3 at 25° C. The pH 7.3 Tris buffer was stored at 2-8° C. until use.

Lyophilized VD peptide (Bachem) was weighted into a glass vial and dissolved into a known volume of the Tris buffer to a concentration between 1 mg/mL and 10 mg/mL. The VD peptide was dissolved by gentle mixing and the solution was allowed to rest for between 20 and 30 minutes. The pH of the solution was checked and adjusted to 7.3 with 0.1 N sodium hydroxide. The solution was filtered through a 0.22 micron sterile filter into a sterile glass vial and stored at 2 to 8° C. until use.

The pharmacodynamic effects of VD delivered by subcutaneous infusion were investigated in a canine model high-rate paced (HRP) to a heart rate of 240 bpm (ventricular pacing) over a period of 10 days to simulate HF. The canines were divided into a control group and an experimental group. The control group received a continuous subcutaneous infusion of the Tris buffer without VD over the course of the 10 day period. The experimental group received continuous subcutaneous infusion of VD dissolved in Tris buffer at a dosing rate of 100 ng/kg·min based upon the body weight of individual canines.

Seven days prior to the beginning of HRP (Day −7), all dogs were instrumented for ventricular pacing with an IPG (implantable pulse generator) including an RA (right atrium) and RV (right ventricle) lead, and a DSI (Digital Sciences International) device in the femoral artery for arterial blood pressure monitoring. Glomerular filtration rate (GFR) was measured by iohexol clearance on the day before the beginning of HRP (Day −1). On Day 0, high-rate pacing was initiated at a rate of 240 BPM (beats per minute) and maintained continuously over the course of a 10 day period (Days 0-10). After HRP was started on Day 0, urine, blood, and hemodynamic data was collected from conscious animals to serve as a baseline.

On Days 0-10, in combination with pacing, each animal received continuous subcutaneous (SQ) infusion of an agent (Tris buffer solution for control animals and vessel dilator in Tris buffer for experimental animals) delivered via external catheter and pump. SQ infusion was performed using Medtronic MiniMed® 407C pumps equipped with 3.0 mL reservoirs (#MMT-103A) and Medtronic Silhouette® combo infusion sets (#MMT373). GFR measurements were repeated on Day 9. On Day 10 (with HRP On), a pre-term monitor was performed for urine and hemodynamic data collection on conscious animals. Once the data was collected, HRP was turned off and the animals were euthanized.

Figure 16:
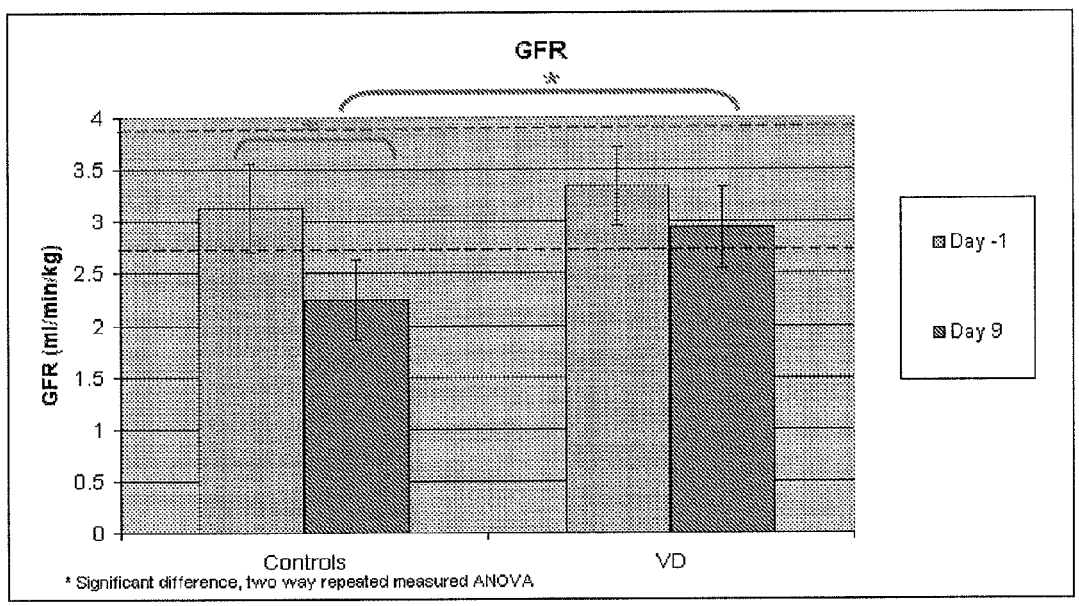
FIG. 16 shows glomerular filtration rates for a canine heart failure model treated with a natriuretic peptide.

One canine died in both the experimental and control groups during the study; therefore, measurements taken on Day 0 were with 5 canines (n=5) and measurements taken on Day 10 were with 4 canines (n=4). FIG. 16 shows the results for GFR measurements taken on Day −1 and Day 9 for the control and experimental VD-treated groups. The bar graph shows the average GFR in units of mL/min per kg of body weight with the standard deviation shown by error bars.

On Day −1, both the control group canines and the VD experimental group canines had GFR measurements greater than 3 mL/min/kg. The normal range of GFR for canines is shown by the dashed lines in FIG. 16. On Day 9 of HRP, the canines in the control group had a GFR less than 2.5 mL/min/kg. The canines in the experimental group receiving VD by SQ infusion also showed a decrease in GFR. However, the experimental group canines showed an average GFR of close to 3.0 mL/min·kg, which is within the normal range for canines. As such, the data presented on FIG. 16 suggests that HRP had a negative impact on GFR where SQ infusion with VD in the experimental group mediated the negative impact as compared with the control group. A statistically significant difference between the average GFR of the control group on Day −1 and the control group on Day 9 was indicated by analysis of variance (ANOVA) statistical analysis. Further, ANOVA statistical analysis showed a statistically significant difference in average GFR between the control group on Day 9 and the average GFR for the experimental group for both Days −1 and Day 9. Maintenance of GFR is a renal protective effect.

Figure 17:
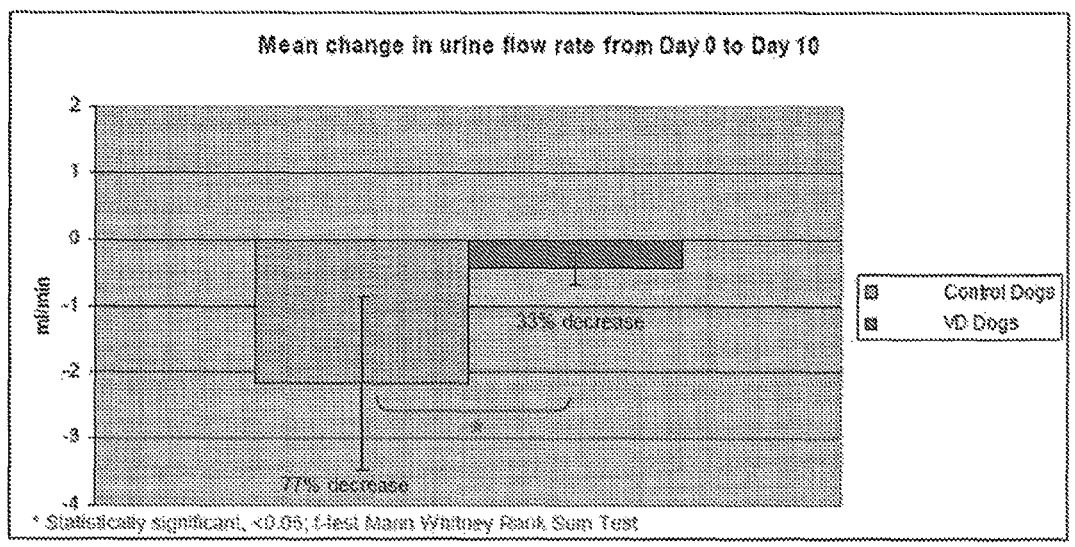
FIG. 17 shows a change in urine flow rate for a canine heart failure model treated with a natriuretic peptide.

FIG. 17 presents the observed change in urine flow in units of mL/min. The change in urine flow is shown on Day 10 with Day 0 serving as the reference baseline. The control group undergoing HRP and receiving SQ infusion of Tris buffer showed a 77% decrease in urine flow on Day 10 compared to the same canines on Day 0. In contrast, the experimental group receiving SQ infusion of VD showed a 33% decrease in urine flow on Day 10 compared to the same canines on Day 0. The standard deviation for both groups is shown by the error bars on FIG. 17.

A statistical comparison of the control group and experimental group showed a statistically significant difference in urine flow between the control group and the experimental group. An application of the Mann-Whitney rank sum test indicated a p-value of less than 0.05, indicating a statistically significant difference between the control group and the experimental group. An increase in urine flow or a decrease in the rate of urine flow loss is a renal protective effect.

Figure 18:
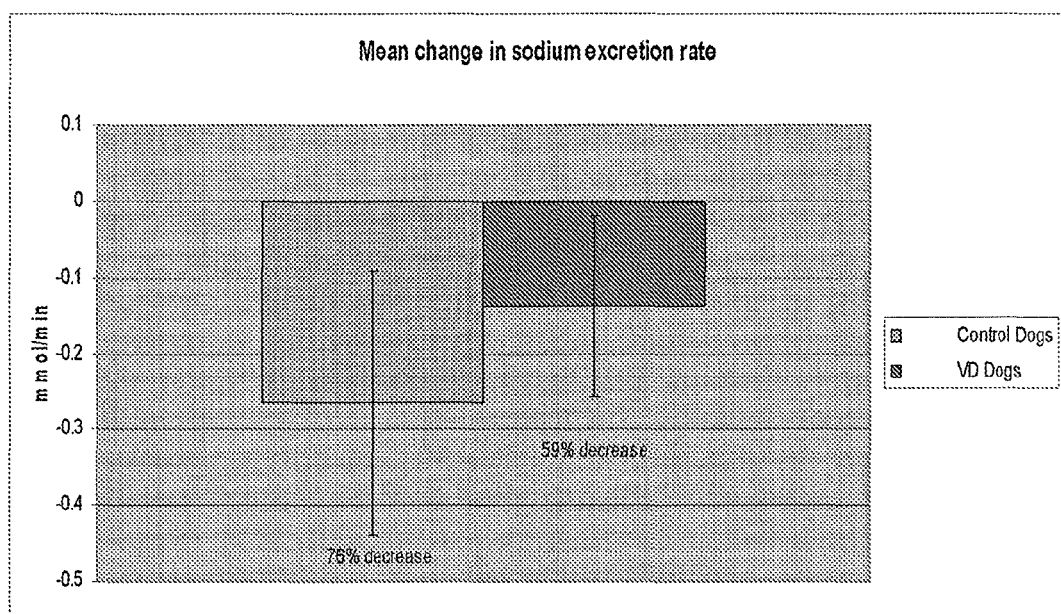
FIG. 18 shows a change in sodium excretion rate for a canine heart failure model treated with a natriuretic peptide.

FIG. 18 presents the observed change in mean sodium excretion rate in units of mmol/min. The change in sodium excretion rate is shown on Day 10 with Day 0 serving as the reference baseline. The control group undergoing HRP and receiving SQ infusion of Tris buffer showed a 76% decrease in sodium excretion rate on Day 10 compared to the same canines on Day 0. In contrast, the experimental group receiving SQ infusion of VD showed a 59% decrease in sodium excretion rate on Day 10 compared to the same canines on Day 0. The standard deviation for both groups is shown by the error bars on FIG. 18. An increase in sodium excretion or a reduction in the decrease in sodium excretion is a renal protective effect.

The error in average sodium excretion rate is elevated due to variations between individual canines. However, the differences in urine average flow rate and average sodium excretion rate between the control group and the experimental group after 10 days of HRP implicates that SQ infusion of VD reduced water and sodium retention, which indicates a renal and/or cardiovascular effect for HF.

Figure 19:
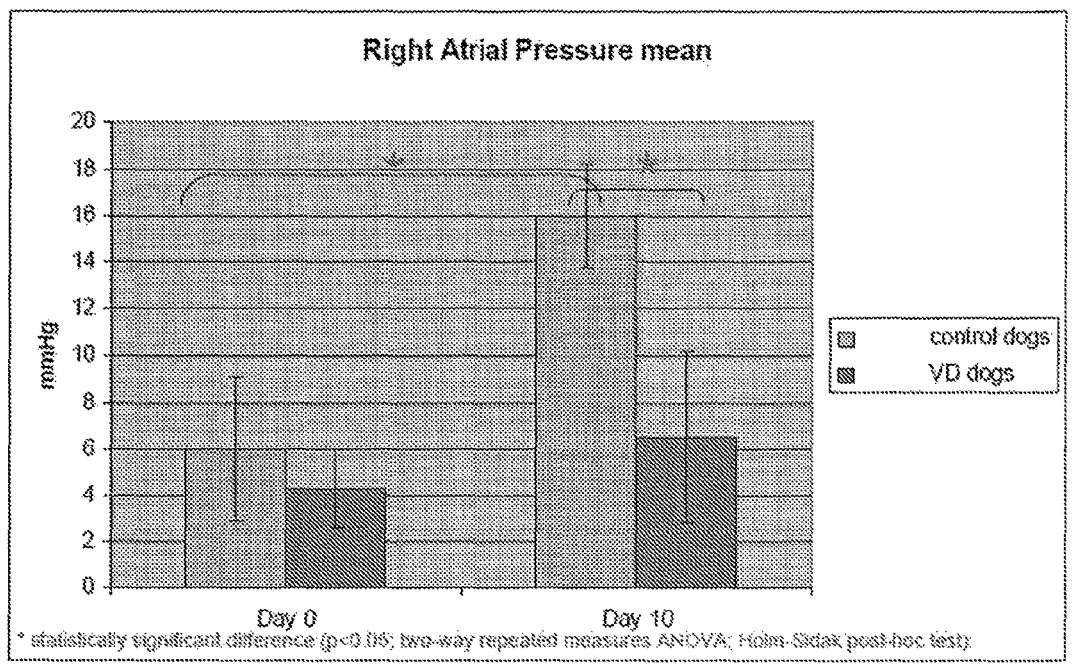
FIG. 19 shows right atrial pressures for a canine heart failure model treated with a natriuretic peptide.
Figure 20:
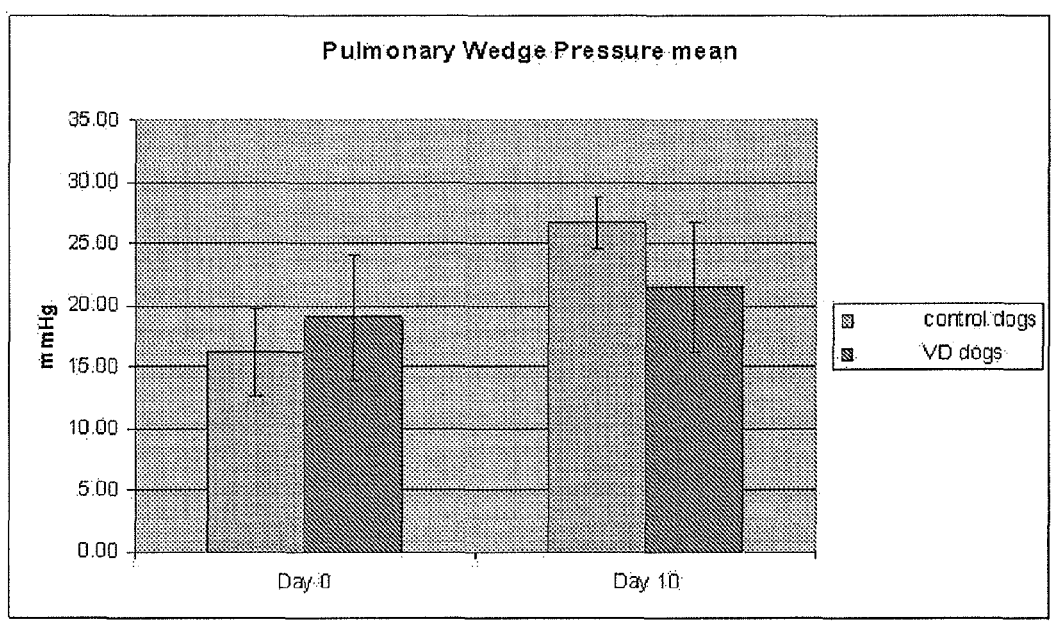
FIG. 20 shows pulmonary capillary wedge pressures for a canine heart failure model treated with a natriuretic peptide.

FIGS. 19 and 20 show the mean right atrial pressure and the mean pulmonary capillary wedge pressure, respectively, for the control and experimental groups. The observed standard deviation is indicated by error bars. As shown for the control group at Day 10, the right atrial pressure is significantly elevated in the control dogs compared with either group at Day 0 (p-value<0.05). ANOVA and post-hoc test indicates that the increase in right atrial pressure in the control group at Day 10 is statistically significant in comparison with the control and experimental groups at Day 0.

A statistically significant change in right atrial pressure is also seen between the control group and the experimental group on Day 10 (p-value<0.05). An increase in right atrial pressure as a result of HRP was expected, as shown by the control group on Day 10 where mean pressure increased from 6 to 16 mmHg. Right atrial pressure increased slightly for the experimental group receiving SQ infusion of VD from Day 0 to Day 10. However, the increase observed for the experimental group is significantly less than for the control group. As such, the data presented on FIG. 19 indicates a hemodynamic benefit for SQ infusion of VD for the HF model. A decrease in the right atrial pressure is a protective cardiovascular effect.

FIG. 20 shows that pulmonary capillary wedge pressure increased as a result of HRP in both the control and experimental groups. The extent of the increase in pulmonary capillary wedge pressure in the experimental group from Day 0 to Day 10 is smaller than that observed in the control group from Day 0 to Day 10. However, the difference in pulmonary capillary wedge pressure between the control group and the experimental group on Day 10 does not appear to be statistically significant (alpha-0.05, two-way repeated measures ANOVA).

Figure 21:
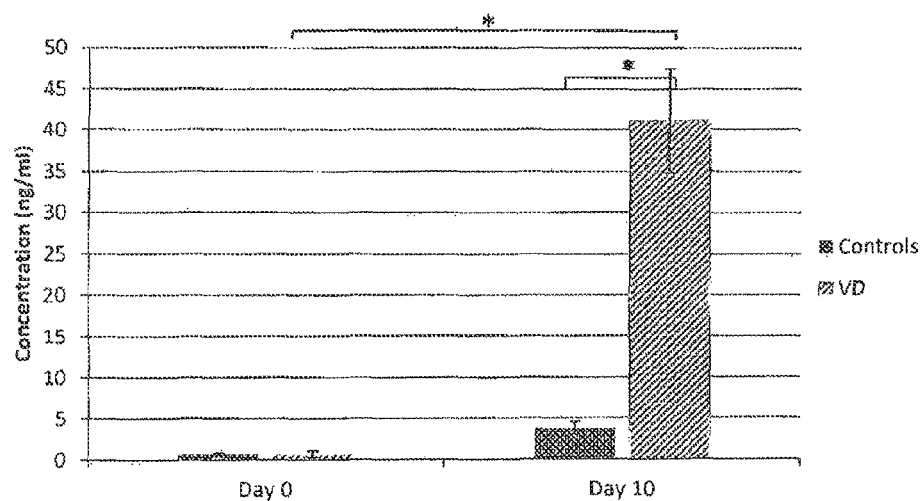
FIG. 21 shows Pre-proANF (56-92) plasma concentration data for a canine heart failure model treated with natriuretic peptide.

FIG. 21 shows the level of Pre-proANF (56-92) measured in plasma on Day 0 and Day 10 of the study. Plasma samples were analyzed using a radioimmunoassay to determine plasma concentrations. The data in FIG. 21 shows a significant increase in peptide of Pre-proANF (56-92) concentration between Day 0 and Day 10 in the VD-treated canines and a statistically significance between the buffer-infused control group canines and the VD-infused experimental group canines on Day 10. The difference in levels of Pre-proANF (56-92) observed reinforces the confidence that the pump continuously and successfully delivered VD over the 10-day infusion period.

Pre-proANF (56-92) plasma concentration was measured by radioimmunoassay in samples collected on Day 0 before vessel dilator infusion and after 10 days of continuous vessel dilator infusion. Pre-proANF (56-92) plasma concentration changed from 0.66+/−0.37 ng/ml on Day 0 to 41.14+/−6.31 ng/ml on Day 10 in experimental group canines that were infused with vessel dilator. Plasma levels in control animals that were infused with buffer were 0.60+/−0.17 ng/ml on Day 0 and 3.72+/−0.76 ng/ml on Day 10.

Cardiac output (CO) and mean arterial pressure (MAP) were also measured in both experimental and control canine groups. In both vessel dilator treated and control animals, CO and MAP decreased following 10 days of high-rate pacing, but there was no treatment effect from vessel dilator infusion. Other outcomes that were measured were urinary potassium, protein, and creatinine excretion, serum renin, angiotensin, aldosterone, creatinine, urea, albumin, total protein, ANP, and NT-proBNP levels, cardiac function from echocardiogram, and gross and histologic pathology assessment. There were no significant treatment effects observed in these outcomes.

EXAMPLE 8

Pharmacodynamic Study Of Vd In Rats

The pharmacodynamic effects of VD were investigated in a rat model. Forty male Dahl/SS rats were shipped to the animal facilities at PhysioGenix, Inc. (Milwaukee, Wis.). The rats were maintained on a low-salt diet and allowed to acclimate. After acclimation, animals had baseline parameters collected while on the low-salt diet. Baseline tail-cuff blood pressures and echocardiograms were measured. Baseline urine was collected for analysis of protein and albumin. Animals were then randomly assigned to one of 4 groups (10 animals per group):
1. Vehicle Control; low-salt diet, n=10
2. Vehicle Control; 4% salt diet, n=10
3. Vessel dilator, 100 ng/kg/min, 4% salt diet, n=10
4. Vessel dilator, 300 ng/kg/min, 4% salt diet, n=10

Lyophilized VD peptide (Bachem) was reconstituted in a Tris buffer having the same composition as the Tris buffer used in Example 7. The vehicle control groups were infused with a citrate-mannitol-saline buffer (0.66 mg/mL citric acid, 6.43 mg/mL sodium citrate, 40 mg/mL mannitol, 9 mg/mL NaCl). The animals were on a Teklad 7034 (low-salt) diet or Dyets AIN-76A 4% salt diet, as indicated, throughout a 6 week course of the study and had free access to water.

Alzet® minipumps (Durect, Corp.) were surgically implanted on Days 1, 15, and 29 of the study to maintain continuous vehicle or drug dispensing at the desired dose for a total period of 6 weeks. Urine was collected at baseline, 2, 4 and 6 weeks after the initiation of the treatment to assess proteinuria and albuminuria. After six weeks of treatment, the animals were then euthanized.

Figure 22:
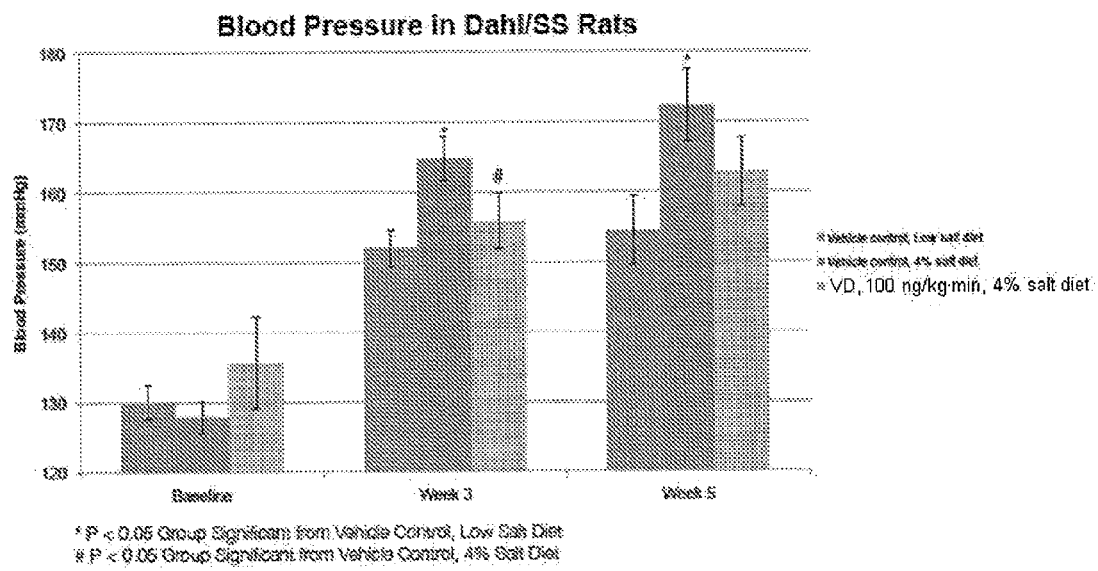
FIGS. 22 A and B show a change in blood pressure for a rat model treated with a natriuretic peptide.
Figure 22:
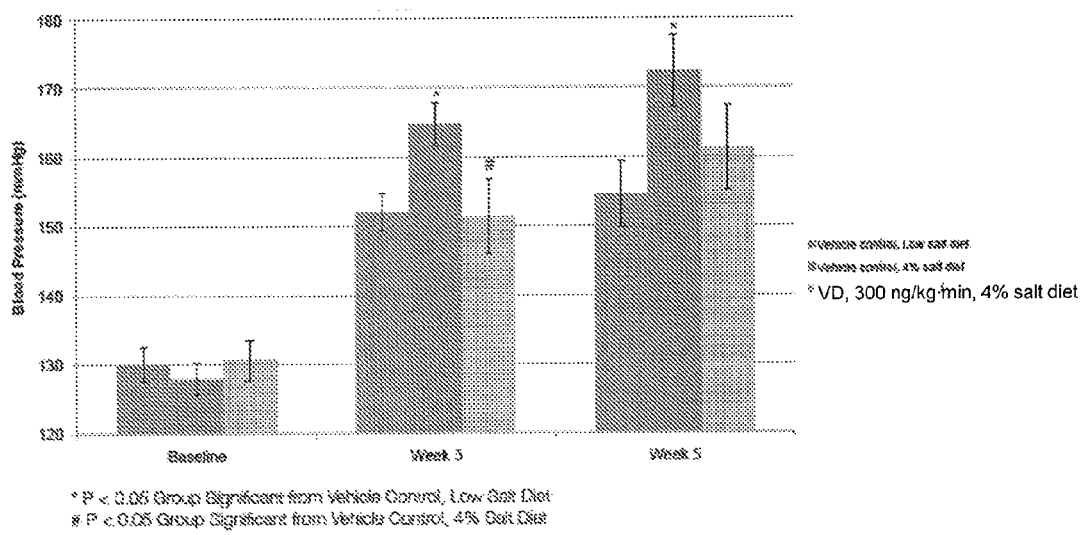

FIGS. 22 A and B present the average blood pressure for the 2 vehicle control groups on the low-salt diet and the 4% salt diet compared with either the group receiving 100 ng/kg/min of VD by SQ infusion (low-dose VD) or 300 ng/kg/min of VD (high-dose VD) by SQ infusion, respectively. Groups receiving the low-dose or high-dose of VD were maintained on the 4% salt diet. As shown in FIG. 22, blood pressure increased in all groups. However, both the low-dose VD and the high-dose VD groups exhibited attenuated blood pressure compared with the vehicle control group on the 4% salt diet.

The vehicle control group on the 4% salt diet showed a statistically significant increase in blood pressure compared with the control group on the low-salt diet (p-value<0.05). At week 3, both the high-dose VD group and the low-dose VD group showed a statistically significant decrease in blood pressure compared with the 4% vehicle control group (p-value<0.05). The decrease in blood pressure of the high-dose VD group and the low-dose VD group at week 5 is not as statistically significant when compared with the 4% vehicle control group at week 5. Nonetheless, the groups treated with VD appear to exhibit protection against blood pressure increase induced by a high-salt diet. The standard error for all groups is shown by error bars. Reduction in blood pressure is a renal or cardiovascular effect.

Figure 23:
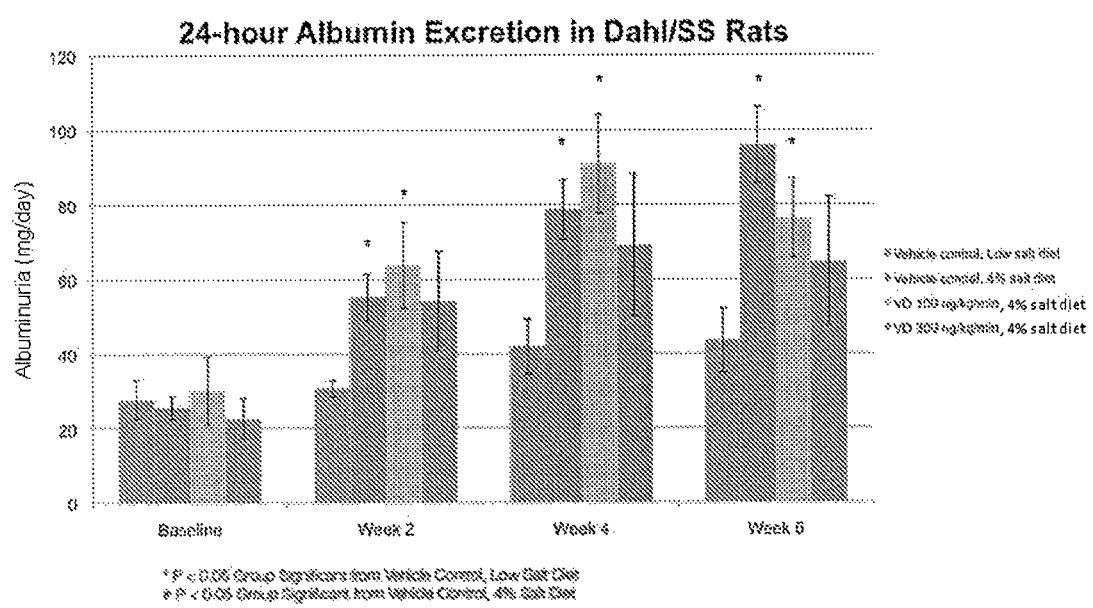
FIG. 23 shows a change in albumin excretion for a rat model treated with a natriuretic peptide.

FIG. 23 presents the 24-hour albumin excretion in urine (mg/day) for the 2 vehicle control groups on low-salt and 4% salt diet, the group receiving the low-dose VD treatment and the high-dose VD treatment by SQ infusion. As shown in FIG. 23, albuminuria increased significantly in the vehicle control group on the 4% salt diet in weeks 2, 4 and 6 compared with the vehicle control group on the low salt diet (p-value<0.05).

As further shown in FIG. 23, the high-dose VD group had dramatically lower levels of albumin excretion in the urine at weeks 2, 4 and 6 compared with the vehicle control group on the 4% salt diet (p-value<0.05). The effect on reducing albuminuria was not as pronounced in the low-dose VD group. Nevertheless, VD infusion appeared to have a positive impact in lowering albuminuria, which is a sign of improved renal function.

Figure 24:
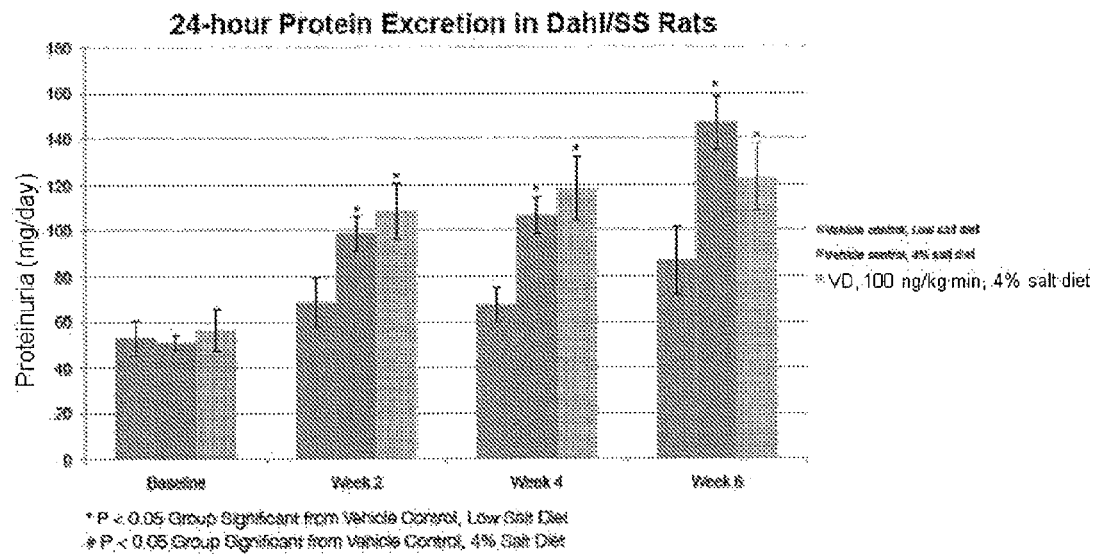
FIGS. 24 A and B show a change in protein excretion for a rat model treated with a natriuretic peptide.
Figure 24:
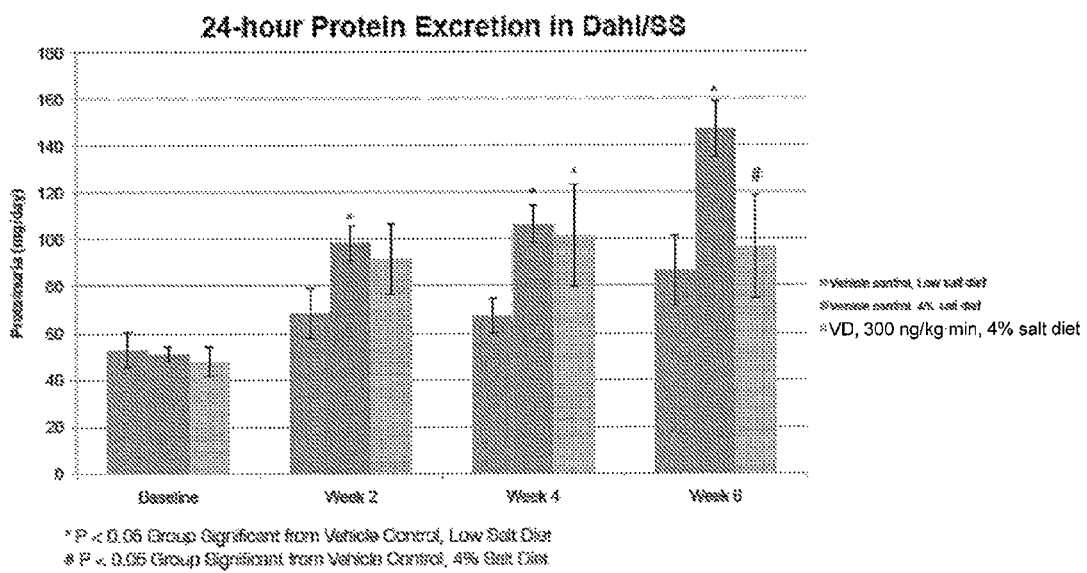

FIGS. 24A and B present the 24-hour protein excretion in urine (mg/day) for the 2 vehicle control groups on low salt diet and 4% salt diet with either the group receiving the low-dose VD treatment or the high-dose VD treatment by SQ infusion, respectively. As shown in FIG. 24, proteinuria increased significantly in the vehicle control group on the 4% salt diet in weeks 2, 4 and 6 compared with the vehicle control group on the low salt diet (p-value<0.05). The standard error for all groups is shown by error bars.

As shown in FIG. 24B, the high-dose VD group showed lower levels of protein excretion in urine at weeks 2, 4 and 6 compared with the vehicle control group on the 4% salt diet. At 6 weeks, the reduction of proteinuria compared with vehicle control group on the 4% salt diet appears to be statistically significant (p-value<0.05). The effect on reducing proteinuria was not as pronounced in the low-dose VD group, as shown in FIG. 24A. Nevertheless, VD infusion appears to have a positive impact in lowering proteinuria, which is a sign of improved renal function and can be a renal protective effect. The standard error for all groups is shown by error bars.

Figure 25:
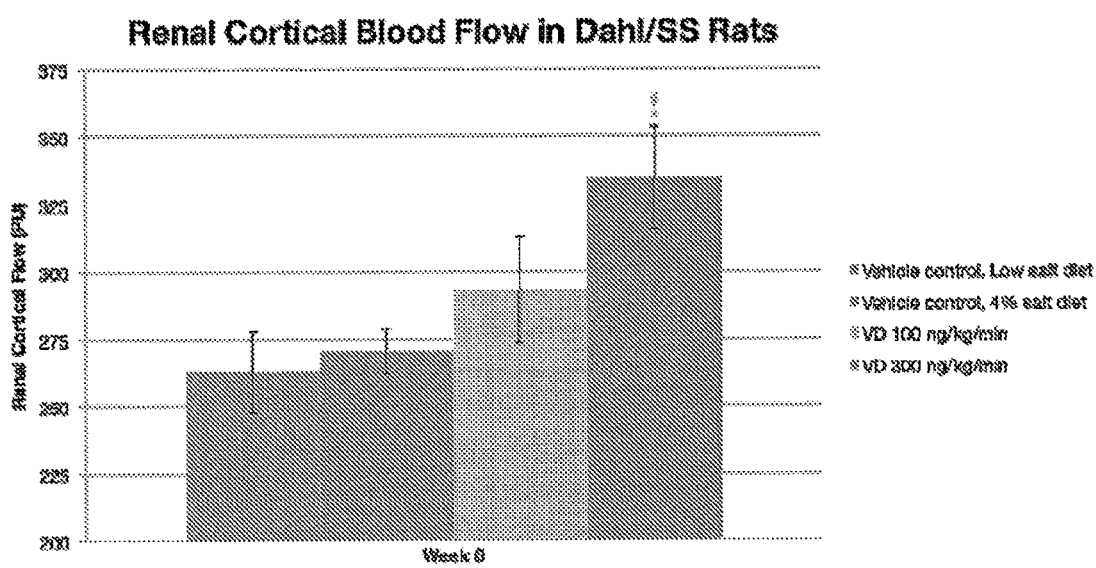
FIG. 25 shows a change in renal cortical blood flow for a rat model treated with a natriuretic peptide.

FIG. 25 presents renal cortical blood flow (as measured in perfusion units (PU)) for the 2 vehicle control groups on low-salt and 4% salt diet and with the groups receiving the low-dose VD treatment or the high-dose VD treatment by SQ infusion. As shown in FIG. 25, renal cortical blood flow increased in the two groups receiving VD peptide relative to the vehicle control groups at week 6. The group receiving the high-dose VD peptide showed significantly increased renal cortical blood flow relative to both the vehicle control group on the 4% salt diet and the low salt diet at the end of the study (p-value<0.05). The standard error for all groups is shown by error bars. An increase in renal cortical blood flow is a renal protective effect.

Figure 26:
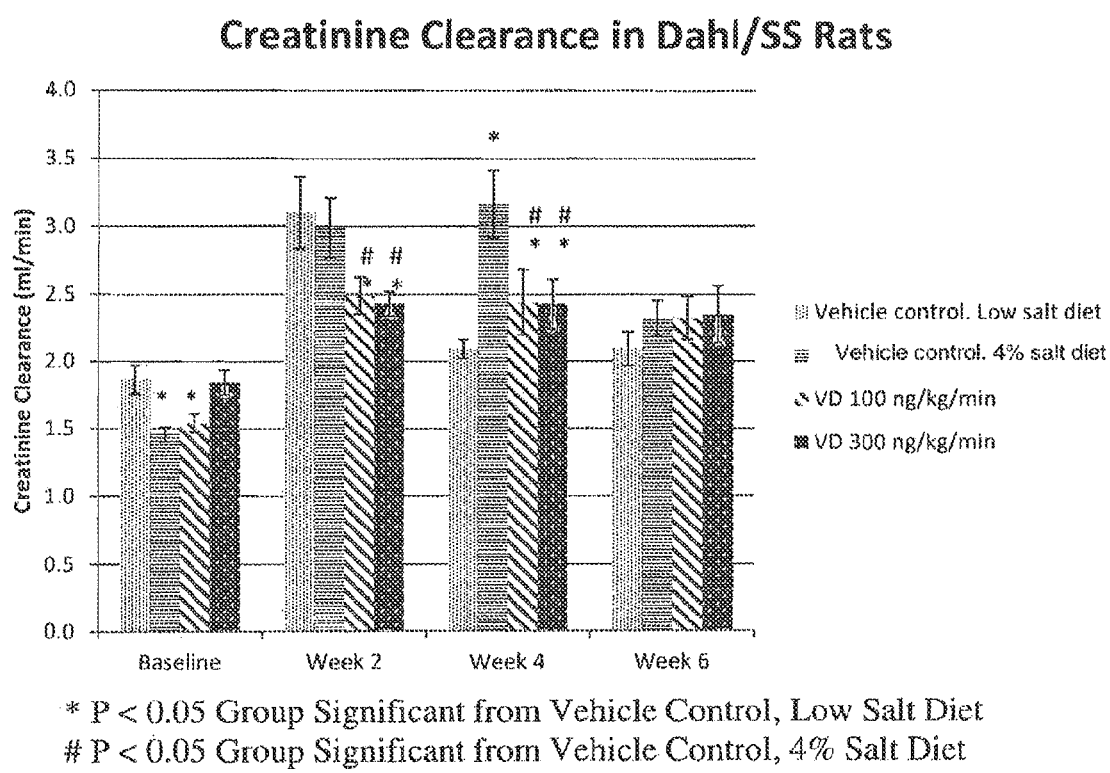
FIG. 26 shows a change in creatinine clearance for a rat model treated with a natriuretic peptide

FIG. 26 presents creatinine clearance data for the two vehicle control groups on low-salt and 4% salt diets and for the groups receiving the low-dose VD treatment and the high-dose VD treatment by SQ infusion. Creatinine is a breakdown product produced in the muscle that is primarily filtered out of the blood by the kidneys and subsequently excreted in the urine. Creatinine clearance compares the level of creatinine in the urine with the level of creatinine in the blood, and provides an estimate of glomerular filtration rate. Specifically, the creatinine clearance data reported in FIG. 26 were calculated using the following formula: urine flow (mL)×urine creatinine concentration (mg/dL)÷plasma creatinine concentration (mg/dL).

Creatinine clearance is influenced by the number of viable nephrons and the perfusion pressure applied to the nephrons. As shown in FIG. 26, by week 2 of the study, creatinine clearance increased significantly compared to the baseline creatinine clearance. The increase affected the low-salt diet control group as well as the 4% salt diet control group. The results showing an increase in creatinine clearance for all groups can be explained by an increase in perfusion pressure in the nephrons brought about by increased blood pressure, as shown in FIG. 22. It is noted that the rats receiving the low-dose and the high-dose SQ infusion of VD both showed statistically significant decreases in creatinine clearance compared to both the low-salt diet and 4% salt diet control groups with a p-value of less than 0.05. Again, the difference is most easily attributable to a drop in blood pressure for the VD-dosed groups.

At week 4, creatinine clearance dropped down to a level similar to the baseline level for the control group on the low-salt diet, and creatinine clearance was maintained at a similar level as week 2 for the two groups receiving VD. However, creatinine clearance remained high for the control group on the 4% salt diet. Again, the rate of creatinine clearance of the VD-dosed groups had statistically significant differences compared to both control groups with a p-value less than 0.05. At week 6, all of the groups dropped to a similar level of creatinine clearance with the control group on the low-salt diet having a slightly lower rate of creatinine clearance.

Histopathology was performed on the kidneys and hearts of all four groups after the conclusion of the 6-week study. The histopathology data showed that the control group on the 4% salt diet had become fibrotic during the course of the study. In contrast, less renal damage was observed in both groups receiving VD by SQ infusion.

Histopathology data was collected as follows. At the time of necropsy, the right kidney and heart were collected from each experimental animal. Organs were weighed, placed in formalin, paraffin-embedded and stained with H & E and Masson's trichrome stains for histological assessment. All slides were evaluated by a board-certified veterinary pathologist and scored. Heart tissues were scored on a semi-quantitative scale from 0-4 for relevant findings noted, where 0=no change; 1=minimal change; 2=mild change; 3=moderate change; and 4=marked change.

Right kidneys and hearts were scored according to criteria described in the following Tables 9-11. For glomerular changes, over 30 glomeruli in each sample were assessed when scoring. The three individual scores for each kidney for glomerular changes, renal tubular casts, and tubule-interstitial changes were also added together to yield a sum score

TABLE 9

WHO-based Scoring System for Glomerular Lesions*

| Score | Histologic features |
|---|---|
| 0 | No siqnificant lesions |
| 1 | Minimal to mild disease, characterized by mesangial deposits |
| 2 | Mild to moderate disease, characterized by hypercellularity with or without mesangial deposits |
| 3 | Moderate to severe disease, characterized by mesangioproliferative glomerulopathy and "wire loop" capillaries with or without fibrinoid necrosis of capillary loops, rupture of Bowman's capsule, and periglomerular inflammation and fibrosis ("crescent" formation). Additional findings may include synechiation of glomerular tufts to Bowman's capsule and protein casts within the tubules. Changes affect less than 50% of the glomerular tufts. |
| 4 | Severe disease with same characteristics as score 3, but affecting 50% or more of the glomerular tufts. |

*Nakajima A. et at, J. Autoimmunity, 2000

TABLE 10

Criteria for Scoring Renal Tubular Casts

| Score | Histologic features |
|---|---|
| 0 | No significant lesions |
| 1 | Proteinaceous material and/or granular casts in <5% of renal tubules |
| 2 | Proteinaceous material and/or granular casts in 5-10% of renal tubules |
| 3 | Proteinaceous material and/or granular casts in 10-30% of renal tubules |
| 4 | Proteinaceous material and/or granular casts in >30% of renal tubules |

TABLE 11

Criteria for Scoring Tubulo-interstitial Changes other than Protein Casts

| Severity | Histologic features |
|---|---|
| 0 | No significant lesions |
| 1 | Focal tubules exhibiting degenerative or regenerative changes +/− minimal interstitial inflammation |
| 2 | Multifocal distribution involving <30% of renal parenchyma-tubules exhibit degenerative and regenerative changes; mild interstitial inflammation; thickened tubular basement membranes |
| 3 | Multifocal distribution involving 30-70% of renal parenchyma-tubules exhibit degenerative and regenerative changes; mild to moderate interstitial inflammation and mild to moderate fibrosis; thickened tubular basement membranes |
| 4 | Multifocal coalescing or diffuse distribution involing >70% of renal parenchyma-tubules exhibit degenerative and regenerative changes; tubular loss or atrophy, parenchymal collapse, moderate to marked interstital inflammation and moderate to marked fibrosis which obscures normal architecture. |

The histopathology results for kidney assessment are shown in Table 12 and for heart assessment in Table 13.

TABLE 12

Composite renal histopathology scores in control and Vessel Dilator treated rats

| | Tubular Casts (Scale: 0-4) (mean ± SD) | Tubulo-Interstitial Changes (Scale: 0-4) (mean ± SD) | Glomerulo-nephropathy (Scale: 0-4) (mean ± SD) | Sum Score (Scale: 0-12) (mean ± SD) |
|---|---|---|---|---|
| Vehicle Control Low Salt | 1.5 ± 0.7 | 1.6 ± 0.5 | 1.4 ± 0.7 | 4.5 ± 1.7 |
| Vehicle Control 4% Salt | 3.1 ± 0.7 | 2.4 ± 0.7 | 3.0 ± 0.5 | 8.5 ± 1.6 |
| Vessel Dilator 100 ng/kg/min | 2.4 ± 0.5 | 2.3 ± 0.5 | 2.4 ± 0.5 | 7.1 ± 1.4 |
| Vessel Dilator 300 ng/kg/min | 2.2 ± 0.8 | 2.4 ± 0.5 | 2.4 ± 0.5 | 7.0 ± 1.8 |

TABLE 13

Histopathology cardiac scores in control and Vessel Dilator treated rats

| | Vascular Smooth Muscle Cell Hypertrophy (0-4) (mean ± SD) | Fibrosis (0-4) (mean ± SD) | Chronic Inflammation (0-4) (mean ± SD) |
|---|---|---|---|
| Vehicle Control Low Salt | 1.2 ± 0.6 | 1.2 ± 0.6 | 0.1 ± 0.3 |
| Vehicle Control 4% Salt | 2.0 ± 0.0 | 1.8 ± 0.4 | 0.4 ± 0.5 |

TABLE 13-continued

Histopathology cardiac scores in control and Vessel Dilator treated rats

| | Vascular Smooth Muscle Cell Hypertrophy (0-4) (mean ± SD) | Fibrosis (0-4) (mean ± SD) | Chronic Inflammation (0-4) (mean ± SD) |
|---|---|---|---|
| Vessel Dilator 100 ng/kg/min | 1.9 ± 0.3 | 1.5 ± 0.5 | 0.4 ± 0.7 |
| Vessel Dilator 300 ng/kg/min | 1.6 ± 0.5 | 1.1 ± 0.3 | 0.2 ± 0.4 |

As shown in Table 12, kidneys from all 3 groups on the 4% salt diet showed similar changes in histopathology with varying severity. Kidneys were characterized by tubules in the cortex and medulla that were dilated, lined by flattened epithelial cells, and filled with eosinophilic homogenous proteinaceous material (casts). Areas of interstitial chronic inflammation were present scattered through mainly the cortex, with associated regions of tubular degeneration and regeneration, and interstitial fibrosis. Glomeruli were often hypercellular and enlarged with mesangial deposits and thickened capillary loops. Some were more shrunken and fibrotic with adhesions to the inner lining of Bowman's capsule. There was occasional peri-glomerular fibrosis. The changes present in the kidneys are classical histomorphologic evidence of a protein-losing glomerulonephropathy which has been documented in this animal model. Composite results of animals in each study arm are shown in Table 12. Overall, Vessel Dilator-treated animals showed less renal damage than the control group on the 4% salt diet.

As shown in Table 13, mild cardiac changes, including vascular smooth muscle cell hypertrophy and perivascular, interstitial, and subendocardial/subepicardial fibrosis are also present in the model. These changes are modestly decreased in the Vessel Dilator treated animals compared to the 4% salt control group.

Figure 27:
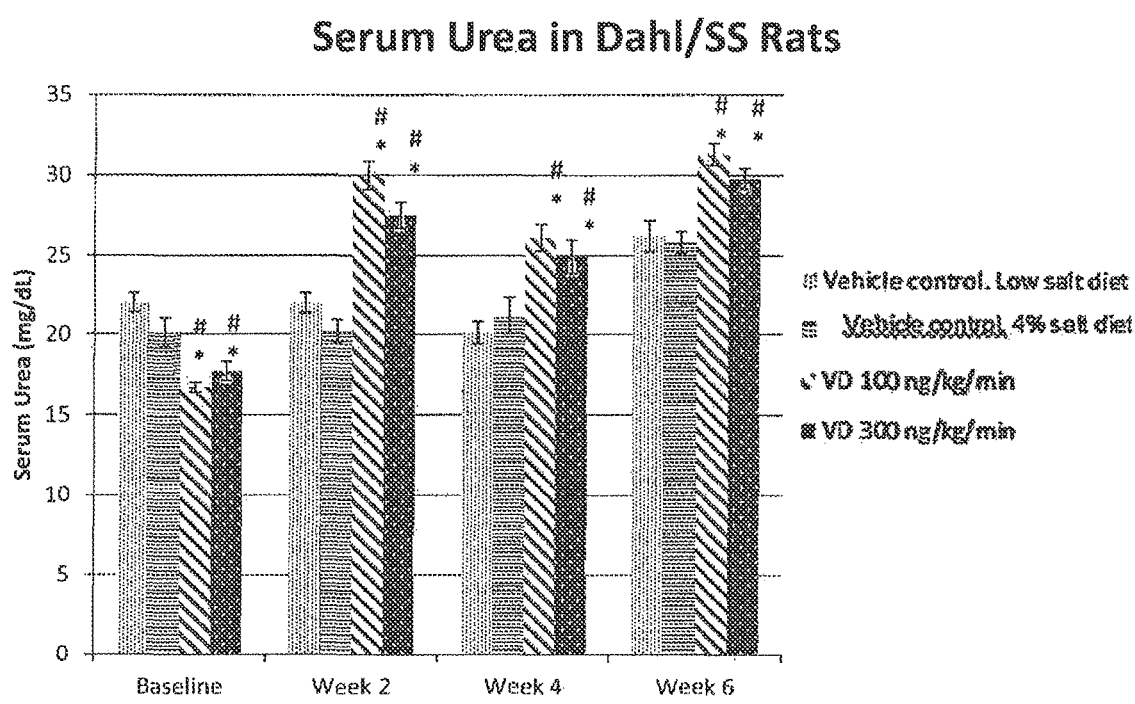
FIG. 27 shows serum urea levels for a rat model treated with a natriuretic peptide.

FIG. 27 shows blood urea nitrogen (BUN) for the vehicle control groups on the low-salt and 4% salt diets as well as the two groups receiving the low-dose VD treatment and the high-dose VD treatment. BUN was measured as serum urea in units of mg/dL. BUN or serum urea concentration is a commonly monitored marker where elevation of BUN is indicative of renal injury or dysfunction by indicating a decreased ability to remove urea from the blood. At baseline, serum urea was significantly lower in both VD-treated groups compared to both control groups. Although this difference appeared to be statistically significant with a p-value less than 0.05, this difference may only represent individual animal variability in the model. There was a general trend of increasing serum urea over the course of the study, but at week 6 of the study, both VD-treated groups had significantly higher serum urea than either control group.

An increase in BUN suggests a decline in renal function. However, it is unlikely that the elevated BUN levels in the VD-treated animals reflected significantly more kidney damage in the Vessel Dilator treated groups than control groups, which would be inconsistent with observed improvements in proteinuria (FIG. 24), albuminuria (FIG. 23) and creatinine clearance (FIG. 26), which are suggestive of Vessel Dilator having a renal protective effect on the kidneys. Further, it is unknown at this time if the BUN values were outside of the normal range regardless of any appearance of a statistically significant difference resulting from a direct comparison of the control groups and the VD-treated groups, as no reference range was available for comparison. Therefore, it is possible that the observed differences in BUN levels were reflective of natural animal-to-animal variation and that all values fell within the normal range. Typically, greater than 60% of the kidney tissue must be damaged before there is evidence of the damage reflected in blood abnormalities.

Figure 28:
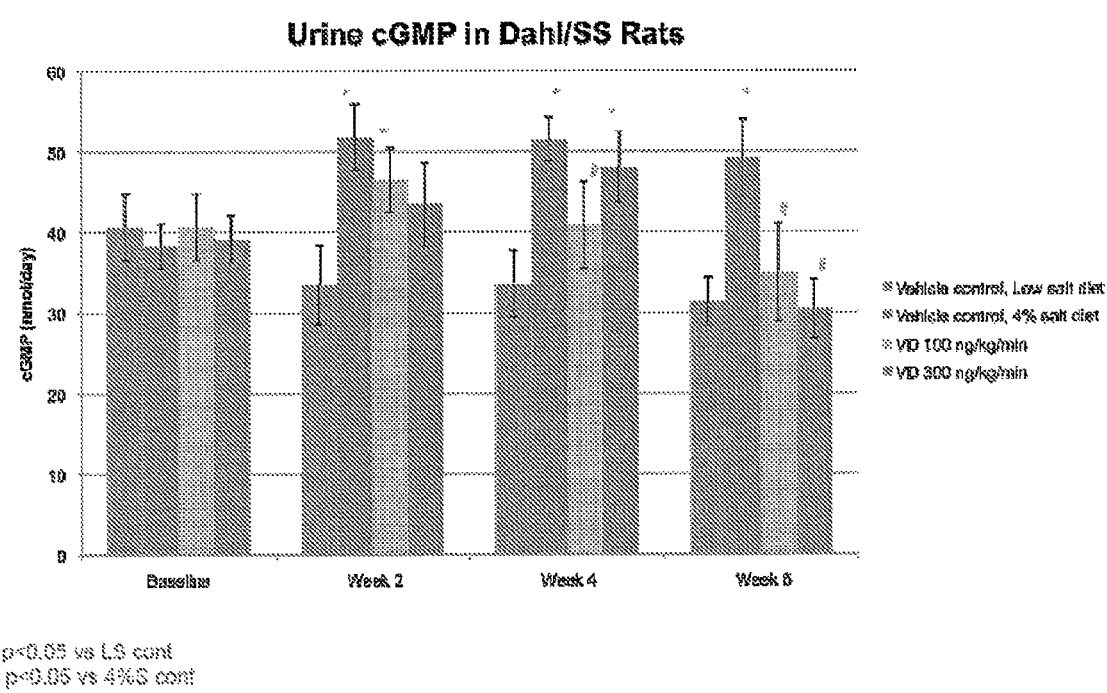
FIG. 28 shows urine cGMP levels for a rat model treated with a natriuretic peptide.

FIG. 28 shows urine cyclic GMP (cGMP) levels for the vehicle control groups on the low-salt and 4% salt diets as well as the two groups receiving the low-dose VD treatment and the high-dose VD treatment in units of mmol/day. Cyclic GMP is a known second messenger generated in response to natriuretic peptides. Urine cGMP levels were measured to evaluate potential upregulation of this second messenger as a result of VD delivered by subcutaneous infusion.

As shown in FIG. 28, urine cGMP was elevated at a constant level at weeks 2, 4, and 6 in the 4% salt diet control group and urine cGMP remained steady at a lower level throughout the duration of the study in the low-salt diet control group. Cyclic GMP levels in the drug-treated groups stayed lower than the cGMP levels in the high-salt diet control group, which suggest that VD at either dose did not activate cGMP above levels stimulated by the high-salt diet itself.

Figure 29:
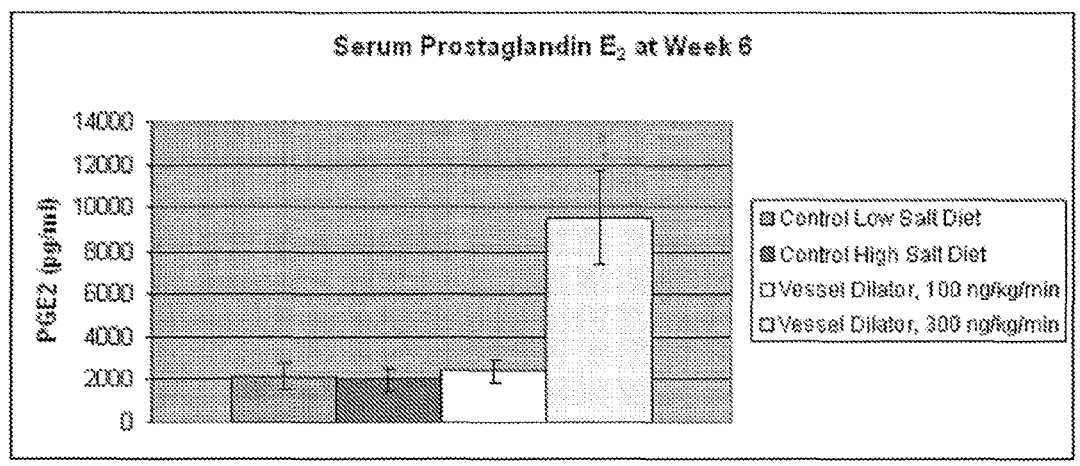
FIG. 29 shows serum prostaglandin $E_2$ levels for a rat model treated with a natriuretic peptide.

FIG. 29 shows serum prostaglandin $E_2$ (PGE2) levels for the vehicle control groups on the low-salt and 4% salt diets as well as the two groups receiving the low-dose VD treatment and the high-dose VD treatment in units of μg/mL. As shown in FIG. 29, PGE2 levels were measured at week 6 of drug treatment. In the VD-treated groups, VD caused a dose dependent increase in PGE2 serum levels, with the PGE level in the high-dose group having a statistically significant increase compared to both control groups. This finding is consistent with previous evidence of PGE2 involvement in the mechanism of action of VD, where PGE2 is known to relax smooth muscles. Other physiological parameters were measured during the 6-week course of the study and are briefly reported here. Serum ANP levels were elevated in high-salt diet control animals at week 6 but not in vessel dilator treated animals. Other outcomes that were measured in blood serum were renin, aldosterone, NT-proBNP, a panel of metabolic markers that included glucose, total protein, and electrolytes, and a panel of kidney injury markers that included cystatin-C, NGAL, and beta-2-microglobulin. Urinary sodium and potassium excretion were also measured, and echocardiograms were performed to assess cardiac function. There were no remarkable treatment effects observed in these outcomes between experimental groups receiving VD and the control groups.

EXAMPLE 9

Subcutaneous Administration in Subjects with Stable Chronic Heart Failure

An alternative study can be performed to establish a dosing for the VD peptide in subjects having stable chronic heart failure (CHF). As discussed, (CHF) is characterized by the inability of the heart to pump blood forward at a sufficient rate to meet the metabolic demands of the body or the ability to do so only if the cardiac filling pressures are abnormally high, or both. CHF is characterized by breathlessness and abnormal sodium and water retention, resulting in oedema, with congestion of the lungs or peripheral circulation, or both. Traditionally, a diuretic therapy, usually a loop diuretic, such as furosemide, in combination with an Angiotensin-Converting Enzyme (ACE) Inhibitor, may be used to control symptoms of CHF. However, these and other current pharmacological treatments for CHF are frequently accompanied by adverse effects, and despite continued advances in pharmacological treatments for CHF, morbidity and mortality resulting from this condition remain high.

As such, new treatment options can be explored for CHF that are not accompanied by adverse effects. Here, treatment of HF, whether chronic heart failure or decompensated heart failure, with VD is proposed by subcutaneous administration. As discussed, potent natriuretic and diuretic effects similar to ANP (Atrial Natriuretic Peptide) are possible with VD with the potential of mitigating adverse effects. VD is also referred to in the literature as proANP [31-67] in reference to VD's origination from amino acids 31-67 of the ANP prohormone, where VD can be artificially synthesized. VD is a 37 amino acid fragment of proANP and consists of a single linear chain amino peptide.

As discussed in Examples 5 and 6 above, VD has been demonstrated to be well-tolerated in both canine and rat models. Following 5 days of constant subcutaneous dosing with 1000 or 2000 ng/kg·min (n=1 per dose and sex) in canines, average steady state peak concentrations were 257-287 ng/mL and 485-527 ng/mL, for the male canine and female canine, respectively. Rats were dosed at (male/female) 90/110, 720/1130 or 1300/2300 ng/kg·min (n=3 per dose and sex) as constant subcutaneous infusion for 5 days. Average peak steady state plasma concentrations in males were 17, 182 and 215 ng/mL, and in females 29, 281 and 475 ng/mL, for the three dose groups.

The results in both dogs and rats compared well between males and females and exposure, in terms of $C_{max}$ and AUC seemed to increase proportionately with dose. There were no signs of toxicity in either species and the maximum tolerated dose for prolonged subcutaneous administration is expected to be above 1300 and 2300 ng/kg·min for male and female rats, respectively, and 2000 ng/kg·min for canines. The difference between male and female rats is driven by the difference in body weight and the body weight-based dosing.

EXAMPLE 10

Human Subcutaneous Infusion Study

The study described herein is designed to evaluate the pharmacokinetic characteristics of VD peptide during steady state conditions during and following a 6-hour subcutaneous infusion of VD peptide. Further, the study is designed to evaluate the safety and tolerability of VD, to assess the non-invasive haemodynamic effects of VD, to evaluate whether VD has effects on renal function, and to quantify and to compare plasma concentrations for VD obtained by two different assays, a radioimmunoassay (RIA) and tandem mass spectrometry assay (LC/MS/MS).

Since the study is designed to determined pharmacokinetic parameters, the study can be an open-label study without a placebo, where the identity of the administered drug is known by the attending clinicians. The study can be of sequential group design with continuous, 6-hour, subcutaneous infusion utilizing an adaptive design and conducted at a single center with subjects having stable chronic heart failure and moderate renal impairment. Two steady state plasma concentrations (Css) of VD will be targeted at approximately 10 and 20 ng/mL. The study can include 2 lead-in patients and 8 patients in each dosing cohort (n=2, lead-in; n=8, 10 ng/mL cohort; and n=8, 20 ng/mL).

As illustrated in Scheme 1 below, the dosing will be sequential, starting with a lead-in of 2 patients at the lower targeted $C_{ss}$ of 10 ng/mL. The 2 lead-in patients can be used to confirm that the measured plasma concentrations are in agreement with the targeted steady state plasma concentration. The pharmacokinetic, safety and tolerability data from the two lead-in patients will be evaluated and, if warranted by the results, a revision of assessment timings and/or infusion rates and duration of dosing may be carried out prior to dosing a cohort of the further 8 patients at the same target concentration of 10 ng/mL.

Following evaluation of results from all patients at the lower target $C_{ss}$ at 10 ng/mL, a second cohort of 8 patients will be dosed at the higher target $C_{SS}$ at 20 ng/mL.

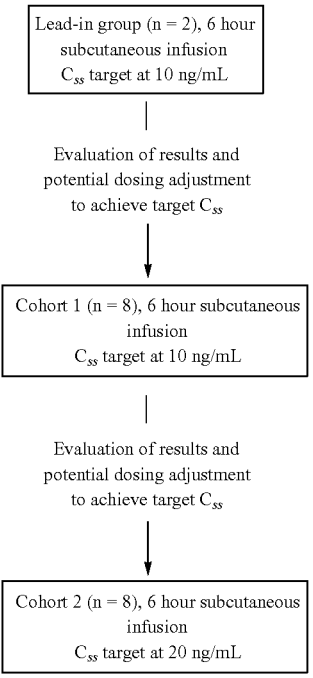

Scheme 1

Patient Safety Protocol and Safeguards

The most likely adverse event to occur during the study is the development of symptomatic hypotension. However, this is unlikely to be a clinically significant problem for the following reasons:

The lower target $C_{SS}$, 10 ng/mL, is expected to be haemodynamically well-tolerated;

The participants in this study will be selected to have stable cardiac disease, which is expected to increase tolerance to increased exposure to VD compared to less stable patients from a haemodynamic standpoint; and Any symptomatic hypotension is expected to be manageable by posture, fluid loading and close observation until the effects have attenuated due to clearance of VD from an affected patient.

The infusion of VD will be stopped in the case of intolerance and will not be restarted for any reason. Below are some criteria that would indicate intolerance to VD and cause cessation of the infusion:

1. A sustained (defined as greater than 30 minutes) systolic BP of <90 mmHg despite simple supportive measures (i.e. fluid resuscitation with 0.9% NaCl and postural change), or 2. A sustained reduction in systolic BP of >15 mmHg despite simple supportive measures as defined above.

Subjects that have had their infusion stopped will be required to stay under observation until the principal investigator (PI or Investigator) conducting the study or a designee is satisfied that the participant can be safely discharged home. Assessments will include, but not be limited to, vital signs including BP and pulse and any other assessment deemed clinically relevant by the PI, including, e.g., IV fluid replacement every four hours during a 24 hour period.

Patient Assessments During the Study

Various assessments will be taken prior to infusion with VD, during the 6-hour infusion with VD, and after cessation of infusion with VD. FIG. 30 shows the proposed collection of assessments for the period prior to subcutaneous infusion and during the 6-hour subcutaneous infusion session. As shown in FIG. 30, assessments will be taken at 21 days prior to the beginning of VD infusion and the day prior (Day 1 pre) to the beginning of VD infusion to establish appropriate baselines, as indicated by the placement of "x's." Assessments will also be taken during the 6-hour infusion period as indicated by the placement of "x's" in FIG. 30.

As indicated in FIG. 30, screening of patients with stable chronic heart failure will occur no more than 21 days prior to the beginning of subcutaneous infusion, although screening may occur at a later time. Subjects with stable chronic heart failure will be recruited from outpatient cardiology sources including private cardiologists, as coordinated by the PI of the study. The study will enroll sufficient participants to allow for a total of 18 evaluable subjects, the two lead-in subjects and a cohort of eight subjects at each dose level as indicated in Scheme 1.

Screening procedures will be as follows as indicated in FIG. 30:
1. Medical history;
2. Concomitant medication history;
3. Physical examination;
4. Weight and height for body mass index (BMI) calculation;
5. Serum pregnancy test for women of childbearing potential (WOCBP);
6. Full blood examination (FBE) and plasma biochemistry (MBA20);
7. CK-MB and Troponin-T;
8. Urinalysis, including urinary protein excretion;
9. Noninvasive cardiac imaging with TTE;
10. Vital sign assessments, including non invasive lying and standing BP, pulse, pulse oximetry, heart rate, respiratory rate and temperature;
11. Electrocardiogram (ECG); and
12. Calculation of GFR with Cockroft Gault formula.

None of the above listed procedures or assessments will be performed until informed consent has been obtained from each participant.

Baseline renal function will be assessed in a period between the above-described screening and at least 2 days prior to the beginning of infusion on Day 1. Renal function will be assessed by measurement of the systematic clearance of 99Tc-MAG3 (technetium-99 mercaptoacetyltriglycine). 99Tc-MAG3 will be administered intravenously and blood samples will be taken at 5, 10 and 15 minutes, and 1, 2 and 3 hours after administration to assess clearance and baseline renal function.

As shown in FIG. 30, the main part of the study will comprise a single residential stay of approximately 28 hours including periods during the 6-hour infusion period and before and after the infusion. Patient participants will arrive in the morning (e.g. at approximately 0800) on Day 1 (dosing day) after a light breakfast at home approximately two hours prior to the beginning of infusion dosing. Caffeine and other xanthines such as cola or chocolate containing foodstuffs, grapefruit and alcohol consumption will not allowed for 24 hours prior to Day 1 and for the entire residential period. An IV cannula will be placed into a forearm vein for blood sampling. This cannula will remain in situ and be re-sited as required.

In the case where multiple assessments are scheduled at the same time point, as shown in FIG. 30, the order of priority will be as follows: Adverse Event (AE) assessment, non-invasive cardiac output measurements and pharmacokinetic parameters. However, the six-hour sample after start of infusion for pharmacokinetics must be taken immediately before the end of infusion session.

The following baseline assessments will be performed prior to start of infusion of VD infusion:
1. Urine pregnancy test for WOCBP;
2. Any participant with a calculated screening GFR of 25≤GFR≤35 ml/min will be required to have a pre-dose MBA20 (lipids and liver function) to calculate GFR prior to dosing. A GFR below 25 mL/min, or a clinically significant decline in GFR from the screening, as reviewed and assessed by the PI or designee, will preclude the participant from further participation in the study;
3. CK-MB (isozymes of phosphocreatine kinase) and Troponin-T;
4. Plasma proBNP and NT-proBNP levels;
5. Spot urine for Na+, K+ and creatinine;
6. Spot urine for renal safety biomarkers kidney injury molecule-1 (KIM1), neutrophil gelatinase lipocalin (NGAL) and Cystatin-C;
7. Vital sign assessments (blood pressure (BP), heart rate (HR), pulse, pulse oximetry, temperature, respiratory rate);
8. Non-invasive cardiac imaging with TTE;
9. Non-invasive cardiac output monitoring with Cheetah NICOM®;
10. electrocardiogram (ECG); and
11. Blood sample for VD pharmacokinetic calculation prior to start of infusion.

Urine tests can be done at any time before start of infusion but NICOM, ECG and vitals will be performed before cannulation and within an hour of start of infusion.

Study drug administration can take place at approximately midday (e.g. noon) on Day 1, the dosing day. Participating subjects should be instructed to take their normal medications at home at approximately 6 am prior to arrival on the morning of Day 1 and should be instructed to bring in all regular medications for use during the study residential period. If dosing is begun at noon, the last assessment on Day 1 will be at midnight, 12-hour time point, which will give the participants 6 hours of undisturbed sleep. Regular medications will be administered at approximately 6 am on the morning of Day 2, at which time the participants may then return to sleep.

The following assessments will be taken during a 24 hour period from the start of infusion, including after cessation of infusion of the VD peptide as shown in FIG. 30:
1. Pharmacokinetic samples for the quantification of VD plasma concentrations will be taken at 20, 40, 60, 80, 100 and 120 minutes, and at 2.5, 3, 3.5, 4, 4.5, 5, and 6 hours after start of infusion. The 6-hour sample must be taken immediately prior to end of the infusion;
2. Following the end of infusion, pharmacokinetic samples will be taken at 20, 40, 60, 80, 100 and 120 minutes, and at 2.5, 3, 3.5, 4, 4.5, 5, 6 and 24 hours after end of infusion;

3. Biochemistry (MBA20) and FBE (full blood analysis) will be obtained at 6 and 24 hours;
4. CK-MB and Troponin-T will be measured at 6 and 24 hours;
5. Plasma BNP and NT-proBNP will be measured at 6 and 24 hours;
6. Continuous urine collection will be carried out throughout three collection intervals, 0-6, 6-12 and 12-24 hours. An aliquot of urine will be taken from the total urine volume at the end of each collection interval for the assessment of renal safety biomarkers (KIM1, NGAL and Cystatin-C), $Na^+$, $K^+$, creatinine and VSDL concentration;
7. Urine volume will be recorded continuously to observe for urine volume reduction;
8. Urine samples for urinalysis will be taken at 24 hours;
9. Vital sign assessments (NIBP (non-invasive blood pressure), HR, respiratory rate, temperature, pulse and pulse oximetry) will be carried out every 10 minutes during the first hour, 15 minutely to 4 hours, 30 minutely to 8 hours, hourly to 12 hours and at 24 hours;
10. Non invasive cardiac output monitoring with Cheetah NICOM® every 10 minutes during the first hour, 15 minutely to 4 hours, 30 minutely to 8 hours, then hourly to 12 hours and at hour 24;
11. ECGs will be collected at 24 hours;
12. Non invasive cardiac imaging with TTE at hours 2, 4, 6 and 24 hours; and
13. Renal blood flow will be measured by the clearance of 99Tc-MAG3; which will be administered IV at 3 hours after start of VSDL infusion. Blood samples will be taken at 5, 10 and 15 minutes, and 1, 2 and 3 hours after administration of 99Tc-MAG3.

Approximately one week after discharge from the facility, a follow-up medical examination will take place. At this visit the following tests/assessments will be conducted:
1. Physical examination;
2. FBE and plasma biochemistry (MBA20);
3. Plasma BNP and NT-proBNP levels;
4. CK-MB and Troponin-T levels;
5. Urinalysis;
6. Vital sign assessments including NIBP, pulse, pulse oximetry, respiratory rate and temperature;
7. Urine safety biomarker analysis (KIM1, NGAL and Cystatin-C); and
8. ECG.

Pharmacokinetic Assessment and Assay of VD

Sampling for plasma concentrations of VD will be carried out during 24 hours following start of dosing, as described above. Samples will be taken as outlined in FIGS. 30 and 31. Following the evaluation of the pharmacokinetic results from the 2 lead-in patients, the sampling schedule may be revised as indicated by the results from the lead-in patients. Sampling times may be changed and number of samples may be decreased.

The quantification of plasma concentration for the purpose of PK data evaluations will be carried out with the LC/MS/MS assay (Method 1) or radioimmunoassay (Method 2). Method 1 is an LC/MS/MS technique that extracts VD and an internal standard from human plasma using protein precipitation extraction. The analytes can be separated by HPLC on a reverse phase C18 column and the species emerging from the HPLC column monitored by an API4000 MS/MS detector in MRM (multiple reaction monitoring) mode. The data can then be assayed against a calibration curve and processed by the Analyst® data acquisition system linked directly to the API4000 MS/MS detector. The method range for quantization can be from 0.2 ng/mL (LLOQ, lower-limit of quantitation) to 100 ng/mL.

With Method 2, plasma concentrations of VD will be measured by radioimmunoassay (RIA) following extraction of the plasma samples by solid phase extraction. The VD RIA is a competitive immunoassay in which a constant concentration of $^{125}I$ radiolabeled peptide (Phoenix Pharmaceuticals, Burlingame Calif., USA) and varying concentrations of unlabeled standard (VD-HCl, Auspep, Tullamarine Victoria, Australia) or sample peptide compete for binding specifically to the antiserum (Bachem, Torrance Calif., USA). Immunocomplexes are precipitated by addition of an excess of non-specific serum and secondary polyclonal antiserum followed by centrifugation to separate bound and unbound peptide. The method range for quantization for Method 2 can be from 0.9 ng/mL (LLOQ) to 49.1 (ULOQ, upper-limit of quantitation).

Method and Experimental Details for Other Assessments

Pertinent experimental details for other assessments will now be briefly described. Noninvasisve cardiac parameters including NIBP, heart rate, respiratory rate, pulse and pulse oximetry will be measured by a Philips Intellivue™ MP5 bedside monitor. Noninvasive cardiac output monitoring will be carried out with the Cheetah NICOM® device at the bedside during 24 hours following start of VD infusion, as outlined in FIGS. 30 and 31. The Cheetah NICOM® device measures changes in the frequency of a low alternating current applied across the thorax to further changes in stroke volume, and hence combined with heart rate it estimates cardiac output. The device is simple to use and consists of 4 pairs of electrodes applied at the base of the patient's neck and at the base of the thorax. There are no symptoms associated with the use of the device and it is regarded as safe. The device gives continuous real-time estimates of cardiac output. This non-invasive technique has been validated against traditional invasive methods such as thermodilution and has been approved by the FDA in the US and other appropriate authorities in other jurisdictions. The device will be used as per manufacturer's instructions.

Transthoracic echocardiography, using a Philips IE33™, will be used to measure estimated EF % (ejection fraction) (3D and 2D Simpson's), systolic and diastolic strain estimation (speckle tracking, E/E' and tissue doppler) and estimates of PA (pulmonary artery) pressure (PA acceleration time, TR jet peak velocity).

As discussed, renal function will be assessed by measurement of the systemic clearance of 99Tc-MAG3 (technetium-99 mercaptoacetyltriglycine). MAG3 has a high renal clearance and is considered a marker of renal blood flow. This procedure was introduced in 1986 and is considered a standard choice in routine practice. 99Tc-MAG3 will be administered as an IV 3 hours after start of VD infusion. Repeated measurements will be taken during 3 hours following administration of 99Tc-MAG3, as outlined FIG. 30. The time of administration can be chosen to correspond with an approximate steady state of VD and sampling of 99Tc-MAG3 may be completed prior to end of VD infusion. A baseline measurement of 99Tc-MAG3 clearance will be carried out, as described in FIG. 30, in addition to during VD infusion. The radiation dose, for each assessment with 99Tc-MAG3 is estimated to be 20 MBq (megabecquerel) and thus a cumulative dose of 40 MBq, i.e. in total 0.4 mSv (milli Sievert), for the two assessments.

Safety assessments will be assessed by spontaneous AE reporting, ECGs and blood analysis (FBE, biochemistry, CK-MB, plasma BNP and NT-proBNP, and Troponin-T), urinalysis and urine protein excretion assessment, noninvasive cardiac and vital sign parameters (including but not be limited to BP, HR, pulse oximetry, pulse, temperature, respiratory rate), urine volume and fluid input monitoring, physical examination, routine urinalysis and assessment of renal blood flow. Renal safety biomarkers (KIM1, NGAL and Cystatin-C) will be quantified only if a participant has a clinically significant change in renal function noted at any time during the study.

Where the infusion to be stopped prematurely due to tolerability issues, a single plasma concentration sample will be taken immediately prior to stopping the infusion. All post infusion procedures described below will be brought forward and carried out in the event of premature termination of infusion.

Study Design and Dosing Regimen

Pharmacokinetics can be evaluated at two target concentration levels of VD, 10 ng/mL and 20 ng/mL, as described. Neither target is expected to be a significant safety concern and is expected to be high enough plasma concentrations to allow characterization of steady state pharmacokinetics and subsequent elimination following administration covering at least three half-lives of elimination of VD. Furthermore, continuous five day subcutaneous infusion of VD to rats and dogs showed no toxicity issues in concentrations up to approx. 740 and 500 ng/mL respectively and the maximum tolerated dose for prolonged subcutaneous administration is expected to be above 1300 and 2300 ng/kg·min for male and female rats, respectively, and 2000 ng/kg·min for canines.

The duration of infusion has been based on an anticipated 30 min (24-60 min) elimination half-life for VD in the plasma. The subcutaneous absorption half-life may be difficult to estimate, but it is expected to be approximately 30 minutes based on the molecular weight of VD. Since it takes approximately five half lives to obtain a steady state concentration in the plasma, an infusion duration of six hours was chosen for this study to provide sufficient time to observe the steady state. The duration can be extended up to eight hours, as appropriate, following the evaluation of results from the lead-in participants in the present study described in Scheme 1.

In order to ensure that the primary study objective of pharmacokinetic characterization during steady state conditions is obtainable, the present study will initially dose only two patients, as a lead-in to the subsequent two cohorts as described in Scheme 1. Following the review of primarily pharmacokinetic findings, and also tolerability and safety findings in the two lead-in patients, the VD infusion rate can be either decreased or increased to obtain the target $C_{ss}$ of 10 ng/mL in the first cohort of eight patients. Likewise, further study design details, such as decrease in number of pharmacokinetic sampling times, actual timings of pharmacokinetic samples and other assessments can be revised in the attempt to optimize information gathering and minimize blood sampling, as informed by the results from the lead-in patients. The maximum number of pharmacokinetic samples, or other assessments, will not likely change beyond what is presently defined. The results from the first cohort will be evaluated and the infusion rate adjusted as appropriate to achieve the target $C_{ss}$ of 20 ng/mL in analogy with the results from the lead-in patients. Patients in the present study will receive a fixed infusion rate, within a given target Css cohort, to allow the evaluation of the necessity for body weight adjusted dosing in future studies.

Selection of Study Population

It is appropriate to study the pharmacokinetic parameters, tolerability and safety in a patient population with stable CHF with moderately impaired renal function, as opposed to healthy volunteers. To qualify for enrollment, all of the following criteria must be met:

1. Patients with a history of stable, symptomatic CHF, with a left ventricular ejection fraction (LVEF) of ≤45% measured with transthoracic echocardiogram (TTE) or gated blood pool scan or cardiac magnetic resonance imaging (CMRI), performed within 90 days prior to screening;
2. Signed Informed Consent;
3. Aged 18 years or older;
4. Non-pregnant females as evidenced by serum pregnancy test at screening and negative. urine pregnancy test pre dose at Day 1 (for women of child bearing potential only). Women of child bearing potential must agree to use a medically acceptable method of contraception (as determined by the Investigator) for the entire study duration. Females of non-child bearing potential are defined as having amenorrhea for at least 2 years prior to study entry or have been surgically sterilized;
5. Brain Natriuretic Peptide (BNP)≥100 µg/mL; and
6. GFR greater ≥25 mL/min/1.73 m2 and less than 70 mL/min/1.73 m² as calculated by Cockroft Gault formula.

The presence of any of the following will exclude a patient from entry into the study:

1. Evidence of myocardial infarction (MI) or high risk acute coronary syndrome within past 6 weeks, as evidenced by ST segment elevation by a 12-lead ECG or by creatine phosphokinase muscle-brain isoenzyme (CK-MB)≥3 times upper limit of normal (as defined by Institute of Medical and Veterinary Science, (IMVS)) or elevation of troponin T>0.1;
2. Evidence of Acute myocardial infarction (MI) (ST elevation and/or elevation of Troponin-T), as determined by a 12-lead ECG and plasma troponin levels;
3. Hypotension (Systolic Blood Pressure (SBP)<90 mmHg), cardiogenic shock, volume depletion or any other clinical condition that would contraindicate administration of an agent with potent vasodilatory effects;
4. Persistent, uncontrolled hypertension (SBP>180 mm Hg);
5. Congenital heart defects;
6. Cardiac surgery within past 4 weeks;
7. Severe valvular heart disease: aortic stenosis (AS), hypertrophic obstructive cardiomyopathy (HOCM), acute aortic incompetence (AI) or mitral regurgitation (MR);
8. Alteration to dose/type/frequency of background therapeutic doses of a beta-blocker, angiotensin-converting enzyme inhibitor (ACE-I) or ARB within the previous six weeks;
9. Alteration to dose/type/frequency of background therapeutic doses of a diuretic and/or aldosterone receptor inhibitor (e.g. spironolactone) within the previous six weeks;
10. History of cerebrovascular accident within past 4 weeks;
11. Acute or chronic active infection, including pneumonia and urinary tract infection
12. Significant renal impairment as determined by a GFR of <25 ml/min as calculated with Cockroft Gault formula. Participants with a GFR of 25≤GFR≤35 mL/min will be required to demonstrate a stable GFR pre-dose on Day 1 to ensure that GFR has not fallen below the protocol specified criteria for ongoing enrolment into the study;
13. Presence of hepatic impairment (defined as ALP, ALT, AST, GGT, Bilirubin >2×ULN) and/or the presence of ascites;
14. Other clinically significant findings on any of the screening laboratory tests, as determined by the Investigator, including but not limited to: hyponatremia, hyperkalaemia, acidosis, anaemia (defined as Hb<9 g/dL);

15. Diagnosis of syndrome of inappropriate antidiuretic hormone hypersecretion (SIADH), Addison's disease or renal salt wasting disease;
16. Receipt of Investigational Drug within 30 days of screening or current enrolment in a clinical trial;
17. History of clinically significant drug or alcohol abuse within the past 12 months—as judged by the Investigator;
18. History of renal or cardiac transplantation;
19. Insufficient venous access;
20. History of current malignancy or malignancy requiring chemotherapy/radiotherapy within 2 years of enrolment (including any current or past history of prostatic malignancy);
21. History of nephrotic syndrome or clinically significant proteinuria (>1 g/24 hr);
22. Known history of infection with Hepatitis C, B or HIV;
23. Use of NSAIDS within 24 hours, or five half-lives, whichever is longer, of start of infusion;
24. History of chronic migraine (defined as >15 episodes per month); and
25. Inability to conform to the conditions of the protocol.

Patient participants will be advised that they are free to withdraw from the study at any time, for any reason, or if necessary, the Investigator may withdraw a participant to protect their health. The Investigator may withdraw a participant if it is considered that the scientific and therefore ethical standards of the study are compromised. Participants may also be withdrawn for not complying with study procedures. The reasons for withdrawal will be fully documented. If a participant is withdrawn from the study due to an adverse event, treatment discontinuation must be explained on the adverse event form, as described below. The participant will be followed-up to the satisfaction of the Investigator.

Drug Information and Dosing Equipment

Study drug (VD) can be manufactured by Auspep Clinical Peptides (Tullamarine, Victoria, Australia) and supplied by the sponsor. VD can be supplied as a white lyophilised powder composed of 1.0 mg of material containing an estimated 811 µg of peptide in 5 mL clear glass vials. Elliotts B® Solution will be used to reconstitute the study drug for subcutaneous administration.

Elliotts B® Solution is a sterile, non-pyrogenic, isotonic buffer that is approved by the United States Food and Drug Administration (FDA) for intrathecal administration of methotrexate sodium and cytarabine. Elliotts B® Solution will be used as a diluent for VD since it provides the appropriate isotonicity and pH attributes desired for SC administration. The stability and compatibility of VD in Elliotts B® Solution at relevant concentrations has been demonstrated. The detailed contents of Elliots B® Solution are provided in the Trial Dispensing Protocol. Storage conditions of the raw material, Elliotts B® Solution, as well as the reconstitution method will be supplied in a Pharmacy Guideline provided during the study.

Below lists the model numbers and components of the Medtronic MiniMed Paradigm® Infusion System to be used in the system. The system includes:
1. A programmable external drug pump (Model MMT722),
2. A drug reservoir, filled by trained staff in the RAH hospital pharmacy, that will hold the vessel dilator (Model MMT332A),
3. An infusion set (Model MMT396) that consists of tubing leading from the drug reservoir to a cannula that is inserted subcutaneously, and
4. A spring loaded inserter device (Model MMT395) is used to insert a small needle through the skin.

An example of a study label is as follows:

```
FOR CLINICAL TRIAL USE ONLY
Human Pro-ANP (31-67) XX.X       micrograms in XX.X mL
  (XXXX nanograms in XX.X mL) in Elliots B Solution
No bacteriostat added. For single use only.
B: 0000000      EXP: 00/000/0000 at      0000      hrs
Patient Name: XXX     Patient ID No: XXX
Route: subcutaneous bolus   Dosage XXX µg
REFRIGERATE 2-8° C.
    Prepared by:
    Prepared at       0000      hrs  on 00/00/2011
```

Additional information may be added to the label as required.

Only participants enrolled in the study will receive the Investigational Product (VD), in accordance with all applicable regulatory requirements. Only authorized site staff will receive, dispense or administer the Investigational Product (VD). The Investigational Product (VD), including all components of the investigational devices, will be stored in a secure area with access limited to the Investigator and authorized staff and under physical conditions that are consistent with the Investigational Product specific requirements. The appropriate records of Investigational Product receipt, handling, usage and disposal for each participant will be maintained as per local practices and in accordance with regulatory requirements.

Study treatment must only be dispensed by a Pharmacist or medically qualified staff trained to fill, store and release study material. Once study treatment is prepared for a participant/patient, it can only be administered to that participant/patient. The Investigator will keep records of all doses of study drug dispensed to allow for reconciliation during and after the study according to all applicable laws and regulations. All components of the investigational devices used in the study will also be reconciled during and after the study.

Participants will be sequentially assigned a three digit participant ID number commencing at 001 or another similar number. This number will be allocated at the screening visit. Blinding will not be required as the study will have an open-label design. Drug compliance by participants/patients will be assured by the Investigator or designee supervising all study drug administration. There will be no interruption of a patient's usual therapy during the study. However, non-steroid anti-inflammatory drugs (NSAIDs) will not be not permitted for 24 hours or five half-lives, whichever is longer, prior to dosing on Day 1.

VD can be administered via subcutaneous 6-hour infusion into the lower abdomen at a maximum volume rate of 350 µL/hr, i.e. approximately 6 µL/min. The exact rate of infusion (dosing rate) of VD for the two targeted $C_{ss}$ levels of 10 ng/mL and 20 ng/mL, respectively. Assuming a bioavailability (F) of 100%, the two infusion rates would be approximately 2.43 µg/min and 4.86 µg/min. The final dosing rates will be higher to achieve the pre-defined target $C_{ss}$ levels, since bioavailability is expected to be lower than 100% for subcutaneous infusion.

In the event of hypotension/intravascular depletion such that signs of impaired end-organ perfusion ensue (such as a reduction in urine output or poor peripheral perfusion), then intravenous fluids will be administered as appropriate. Any more unexpected, severe adverse events such as cardiogenic shock would be managed potentially with inotropic support or other cardiac support measures (i.e. balloon pump) as required in a specialized cardiac monitoring facility, although such events are not expected.

Procedure for Documenting Adverse Events

An adverse event (AE) is defined as any untoward medical occurrence in a patient or clinical investigation subject administered a pharmaceutical product and does not necessarily have a causal relationship with the administration of VD. An adverse event can therefore be any unfavorable and unintended sign (including an abnormal laboratory finding), symptom, or disease temporally associated with the use of a medicinal (investigational) product, whether or not related to the medicinal (investigational) product.

In the pre-approval clinical experience with a new medicinal product or its new usages, particularly as the therapeutic dose(s) may not be established, all noxious and unintended responses to a medicinal product related to any dose should be considered adverse drug reactions (ADRs). The phrase "responses to a medicinal product" means that a causal relationship between a medicinal product and an adverse event is at least a reasonable possibility, i.e., the relationship cannot be ruled out.

An "Unexpected Adverse Reaction" is defined as the nature or severity of which is not consistent with previous observations during the administration of the drug product.

A "Serious Adverse Event" (SAE) or "Serious Adverse Drug Reaction" (Serious ADR) is defined as any medical occurrence that at any dose:

1. Results in death;
2. Is life-threatening;
3. Requires inpatient hospitalization or prolongation of existing hospitalization;
4. Results in persistent or significant disability/incapacity; or
5. Results in a congenital anomaly/birth defect.

At each required study visit, all adverse events (AE) that have occurred since the previous visit will be and must be recorded in the adverse event record of the participant's/patient's case report form (CRF). The information recorded should be based on the signs or symptoms detected during the physical examination and clinical evaluation of the patient.

The following AE information will be and must be included (when applicable): the specific condition or event and direction of change; whether the condition was preexisting (i.e., an acute condition present at the start of the study or history of a chronic condition) and, if so, whether it has worsened (e.g., in severity and/or frequency); the dates and times of occurrence; severity; causal relationship to study drug or device; action taken; and outcome. The causal relationship between an AE and the study drug will be determined by the Investigator based on his or her clinical judgment.

When assessing the relationship between administration of a study drug or device and an AE, the following should be considered:

1. Temporal relationship between administration of the study drug or device and AE;
2. Biological plausibility of relationship;
3. Patient's underlying clinical state or concomitant agents and/or therapies;
4. When applicable, whether the AE abates on discontinuation of the study drug (de-challenge); and
5. When applicable, whether the AE reappears on repeat exposure to the study drug (re-challenge);

The following guide to grading AE severity can be used in the reporting of AEs:

Mild (grade 1): The AE is noticeable to the subject but does not interfere with routine activity. The AE does not require discontinuing administration or reducing the dose of the study drug.

Moderate (grade 2): The AE interferes with routine activity but responds to symptomatic therapy or rest. The AE may require reducing the dose but not discontinuing administration of the study drug.

Severe (grade 3): The AE significantly limits the subject's ability to perform routine activities despite symptomatic therapy. In addition, the AE leads to discontinuing administration or reducing the dose of the study drug.

Life Threatening (grade 4): The AE requires discontinuing administration of the study drug. The subject is at immediate risk of death.

The Investigator will be obligated to assess the relationship between Investigational Product and the occurrence of each adverse event/serious adverse event. The Investigator will use clinical judgment to determine the relationship. Alternative causes, such as natural history of the underlying diseases, concomitant therapy, other risk factors, and the temporal relationship of the event to the Investigational Product will be considered and investigated. The Investigator can also const an Investigator's Brochure that will be available during the study in the determination of his/her assessment. The causal relationship of the adverse event to the Investigational Product (including the investigational device) or study procedures should be assessed by the Investigator (or medically qualified delegate). The following Table 14 is a guide to Assessment of Relationship to study drug.

TABLE 14

Guide to Relationship Assessment

| Relationship | Description |
| --- | --- |
| Not Related | In the Investigator's opinion, there is not a causal relationship between the study product and the adverse event. |
| Possible | The adverse event follows a reasonable temporal sequence from the time of study product administration but could have been caused by the study subject's clinical state or other modes of therapy administered to the subject. |
| Probable | The adverse event follows a reasonable temporal sequence from the time of study product administration, abates upon discontinuation of the study product and cannot be reasonably explained by the known characteristics of the study subject's clinical state. |
| Related | The adverse event follows a reasonable temporal sequence from the time of study product administration, abates upon discontinuation of the study product and reappears when study product is reintroduced. |

Serious Adverse Event Reporting

All serious adverse events will require expeditious handling and will be reported within 24 hours by FAX or phone to the sponsor of the study upon discovery. An SAE reporting form will be provided and available at the study site with detailed instructions regarding completion and contact information for reporting the SAE. Any SAE, regardless of causal relationship, will be reported to the sponsor immediately (no later than 24 hours after the investigator becomes aware of the SAE) by completing the SAE form and then confirming receipt by telephone that the form was received. Compliance with this time requirement is essential so that the sponsor may comply with its regulatory obligations. Follow-up information relating to an SAE will be reported to the sponsor within 24 hours of receipt by the Investigator by sending a completed SAE form and confirming by telephone that the email was received. The participant/patient should be observed and monitored carefully until the condition resolves or stabilizes or its cause is identified. Further, all SAE's will be reported to an ethics committee within 72 hours. If known, the diagnosis of the underlying illness or disorder should also be recorded, rather than its individual symptoms.

Pharmacokinetic Calculations and Statistical Methods

This study is designed to be an exploratory trial aimed at investigating the steady state pharmacokinetic characteristics of VD following subcutaneous infusion. The number of participants is based on feasibility considerations aimed at providing information that will meet these objectives. Data from subjects with missing or incomplete information may be included, but in such a manner as to minimize bias and not jeopardize quality of the output from the various analyses.

Due to the exploratory nature of the study, standard summary statistics will be used and all statistical methods will be descriptive. Pharmacokinetic variables such as maximum observed peak concentration ($C_{max}$), time of Cmax ($t_{max}$), area under the plasma concentration time curve (AUC), clearance (CL/F), apparent volume of distribution Vz/F and terminal half-life ($t_{1/2}$) will be determined by standard non-compartmental methods. $C_{max,ss}$ and $t_{max,ss}$ will be taken directly from the observed data. AUC will be calculated using the linear up log down trapezoidal method to the last quantifiable concentration ($C_{last}$). The remainder will be extrapolated as $C_{last}/k_z$ where $k_z$ is the terminal rate constant determined by least-squares regression of the terminal slope of the log concentration-time curve. CL/F will be calculated as Dose/AUC, Vz/F as CL/(F*$k_z$) and $t_{1/2}$ will be calculated as ln $2/k_z$. Further analysis may be carried out as appropriate.

An exploratory analysis, utilizing mixed effects modeling, may also be carried out to obtain pertinent pharmacokinetic parameters and related variability. The potential relationship between pharmacokinetic and pharmacodynamic variables, e.g. selected haemodynamic or renal measures and/or adverse events will also be explored if warranted. Potential pharmacokinetic/pharmacodynamic relationships will initially be explored by graphical presentation of data, followed by modeling of potential relationships, as appropriate. The exploratory analysis may also utilize data from previous trials, as a pooled data set is expected to provide a better foundation for the determination of pharmacokinetic parameters, variability and pharmacokinetic/pharmacodynamic relationship(s).

Pharmacodynamic information will also be analyzed. Particularly, maximal change in pertinent non-invasively measured cardiac parameters. Variables of interest can be, but not limited to, cardiac index, left ventricular ejection fraction (LVEF) and arterial BP. The primary endpoints are changes in BP and cardiac output (CO).

A safety analysis of reported AEs will also be performed. All AEs will be listed by participant. The incidence and intensity of AEs and of abnormalities of clinical laboratory tests will be summarized by dose/cohort. The corresponding number of AE's from baseline will be measured. The results will be tabulated by dose/cohort.

Vital signs: systolic and diastolic blood pressure and pulse rate will be summarized at each time point using descriptive statistics. Subsets of data such as during infusion may be summarized separately if warranted by the findings.

Change in renal safety biomarkers KIM-1, NGAL and Cystatin-C will be tabulated by dose/cohort. Baseline values will be compared to assessments during and after VD infusion.

Changes in renal function assessment by renal blood flow will be tabulated by dose/cohort and comparison between value at baseline and during VD infusion will be compared.

Further analyses will be carried out, as informed by the data. Adverse events will be coded by data management Study Management, Training and Data Management Staff will be trained prior to screening on the use of the Cheetah NICOM® device for noninvasive cardiac output monitoring at the bedside and given other appropriate instruction.

The study shall be performed in accordance with and to a timetable specified in study agreements between the Sponsor and involved parties, including but not limited to the clinical research site, data management service, and the bioanalytical facility (CPR Pharma Services Pty Ltd).

An independent monitor will be appointed to monitor the study in accordance with local regulatory guidelines and as per a Study Monitoring Plan to be provided. Safety monitoring will be by undertaken by the PI and optionally, a co-Investigator.

The study source documents and other supporting documentation will be the primary source of data for all assessments and measurements including vital signs, adverse events, timing of study procedures and concomitant medications. The source document for the ECGs will be the paper readouts. Data will be recorded at specified time points for the Cheetah NICOM® device and comprehensive, continuous cardiac parameter information can be downloaded as required. Medical history obtained from the PI and recorded in the source book will be supported by any letters of referral or medical history obtained from previous investigations or outpatient/specialist reviews and from hospital in-patient notes where applicable and available.

Source documents will be original documents, data, and records from which the participants CRF data are obtained. These include, but are not limited to, hospital records, clinical and office charts, laboratory and pharmacy records, diaries, microfiches, radiographs, and correspondence. CRF entries may be considered source data if the CRF is the site of the original recording (i.e., there is no other written or electronic record of data).

In compliance with local regulations and guidelines and International Conference on Harmonization (ICH) GCP guidelines, it is usually required that the Investigator and institution permit authorized representatives of the Sponsor, the regulatory agency(s), and the research ethics committee direct access to review the participants original study records for verification of study-related procedures and data. Direct access includes examining, analyzing, verifying, and reproducing any records and reports that are important to the evaluation of the study. The Investigator will be obligated to inform the participant/patient and obtain their consent to permit named representatives to have access to his/her study-related records without violating the confidentiality of the participant.

All source documents, CRFs and study documentation will be kept by the Investigator for the appropriate retention period of fifteen (15) years after completion of the services as usually required by local regulations and ICH-GCP. The study files shall be made available to authorized representatives of the Sponsor upon written request at any time during this period. No trial document should be destroyed without prior written agreement between the Sponsor and the Investigator. Should the Investigator wish to assign the trial records to another party or move them to another location, the Investigator must notify the Sponsor in writing of the new responsible person and/or the new location.

Quality of data transfer from source documents to CRFs shall be verified by on-site monitoring as per a Study Monitoring Plan to be provided. Original CRFs shall be provided to data management who will enter the CRF data into the study database and reconcile it in a two-pass quality process. A manual review of data and the discrepancy database shall be performed prior to the initiation of data rectification forms to the site staff and subsequent rectification of information in the database. Medical coding shall precede duplicate quality control checks prior to database lock.

Study Approval and Conduct

The Clinical Trial Notification requirement of the appropriate regulatory authority will be met before commencement of the study. The Sponsor will be responsible for reporting all serious, life threatening or fatal adverse events with a causal relationship to the Investigational Product to appropriate regulatory agencies within the required timelines.

The Principal Investigator will ensure that this study is conducted in full compliance with the Protocol, the Declaration of Helsinki, and the International Conference on Harmonization (ICH) guideline for GCP, and government regulations, and all other applicable local laws and regulations. Compliance with these standards provides assurance that the rights, safety, and well being of subjects are protected. In agreeing to the provisions of the Protocol, these responsibilities are accepted by the Investigator.

This study will be carried out according to the Declaration of Helsinki, the Notes for Guidance on Good Clinical Practice (2000) (CPMP/ICH/135/95) and with ICH GCP as adopted in Australia and the National Statement on Ethical Conduct in Human Research, October 2007. The Protocol will be submitted for approval to the appropriate Human Research Ethics Committee (HREC), and written approval obtained before participants are enrolled. The composition of the HREC will also be provided to the Sponsor. If approval is suspended or terminated by the HREC, the Investigator will notify the Sponsor immediately.

Copies of correspondence will be retained in the study site file. In addition, it is the responsibility of the Investigator to report study progress to the HREC as required or at intervals no greater than one year.

The Principal Investigator at each study site or his/her nominee will be responsible for reporting any serious adverse events to the HREC as soon as possible, and in accordance with the guidelines of the HREC.

Prior to initiation of this study, a copy of the local laboratory certification form, with certification number and expiration date will be collected. Reference ranges for each laboratory test used in this study will be obtained.

With the consent of the participant/patient, it will be the Investigator's responsibility to notify the primary care physician of the participant's/patient's entry in the study, provided that such a physician can be identified for the participant. A letter will be sent to the physician stating the nature of the study, treatments, expected benefits or adverse events and concomitant drugs to be avoided. The study site shall retain a copy.

No changes (amendments) to the Protocol of this study will be implemented without prior approval from the Sponsor and the appropriate HREC, except where necessary to eliminate an immediate hazard to participants, or when the change involves only logistical or administrative aspects of the study. If a Protocol Amendment requires changes to the Informed Consent Form, the revised Informed Consent Form, prepared by the Investigator, must be approved by the HREC.

Once the final Protocol has been issued and signed by the Investigator and the authorized signatories, it shall not be informally altered. Protocol amendments are alterations to a legal document and have the same legal status. Therefore, they must pass through appropriate steps before being implemented. In general, any important change that theoretically increases risk to subjects constitutes an amendment. Protocol modifications that impact on participants' safety or the validity of the study will be approved by the HREC. Minor changes such as administrative changes may be documented without approval, if permissible by the HREC.

Neither the Investigator nor the Sponsor will modify the Protocol without first obtaining the concurrence of the other in writing. It will be the responsibility of the Investigator to submit the amendment to the HREC for their approval; written approval should be obtained and a copy provided to the Sponsor. The Sponsor will be responsible for determining whether or not the local regulatory authority must be notified of the Protocol change. Completed and signed Protocol amendments will be circulated to all those who were on the circulation list for the original Protocol.

The original signed copy of amendments will be kept in the Investigator File with the original Protocol. It should be noted that where an amendment to the Protocol substantially alters the study design or the potential risks to the patient, each patient's consent to continue participation should be obtained.

| Table of Abbreviations | |
|---|---|
| ACE | Angiotensin-Converting Enzyme (Inhibitor) |
| ADR | Adverse Drug Reaction |
| AE | Adverse Event |
| AI | Aortic Incompetence |
| ALP | Alkaline Phosphatase |
| ANP (ANF, ANH) | Atrial Natriuretic Peptide (Atrial Natriuretic Factor) |
| ARB | Angiotensin Receptor Blocker |
| AS | Aortic Stenosis |
| AST | Aspartate Aminotransferase |
| AUC | Area under the plasma concentration-time curve |
| BMI | Body Mass hidex |
| BNP | B-type Natriuretic Peptide or Brain Natriuretic Peptide |
| BP | Blood Pressure |
| $C_{ss}$ | Steady-state plasma concentration of VSDL |
| CHF | Congestive Heart Failure |
| CI | Cardiac Index |
| CK | Creatine Kinase |
| CK-MB | Creatine Kinase muscle-brain isoenzyme |
| CL | Clearance following intravenous administration |
| CL/F | CL following non-intravenous administration |
| CMR | Cardiac Magnetic Resonance |
| CO | Cardiac Output |
| Cr | Creatinine |
| CrCL | Creatinine Clearance |
| CXR | Chest X-Ray |
| ECG | Electrocardiogram |
| EF | Ejection Fraction |
| F | Bioavailability |
| FBE | Full Blood Examination |
| GCP | Good Clinical Practice |
| GFR | Glomerular Filtration Rate |
| GGT | Gamma-Glutamyl Transeptidase |
| HIV | Human Immunodeficiency Virus |
| GMP | Good Manufacturing Practice |
| HOCM | Hypertrophic Obstructive Cardiomyopathy |
| HR | Heart Rate |
| HREC | Human Research Ethics Committee |

| Table of Abbreviations | |
|---|---|
| ICH | International Conference on Harmonization |
| IV | Intravenous |
| K⁺ | Potassium |
| KIM1 | Kidney Injury Molecule 1 |
| LC/MS/MS | Liquid chromatography/Tandem Mass Spectrometry |
| LVEF | Left ventricular ejection fraction |
| MI | Myocardial Infarction |
| MO | Medical Monitor |
| mmHg | Millimeters of Mercury |
| Na⁺ | Sodium |
| NaCl | Sodium Chloride |
| NGAL | Neutrophil Gelatinase-Associated Lipocalin |
| NIBP | Non Invasive Blood Pressure |
| NICOM | Non Invasive Cardiac Output Monitor |
| NSAID | Non-Steroidal Anti-Inflammatory Drug |
| NT-proBNP | N-Terminal prohormone of Brain Natriuretic Peptide |
| NYHA | New York Heart Association |
| PAP | Pulmonary Artery Pressure |
| PARC | Pain and Anaesthesia Research Clinic |
| PCWP | Pulmonary Capillary Wedge Pressure |
| PD | Pharmacodynamic(s) |
| PK | Pharmacokinetic(s) |
| PI | Principal Investigator |

| Table of Abbreviations | |
|---|---|
| PPM | Permanent Pacemaker |
| proANP | Atrial Natriuretic Prohormone |
| Ro | Rate of infusion |
| RAH | Royal Adelaide Hospital |
| RR | Respiratory Rate |
| RIA | Radioimmunoassay |
| SADR | Serious Adverse Drug Reaction |
| SAE | Serious Adverse Event |
| SBP | Systolic Blood Pressure |
| SC | Subcutaneous |
| SIADH | Syndrome of Inappropriate Antidiuretic Hormone Hypersecretion |
| $t_{1/2,IV}$ | Terminal half-life, foUowing IV administration |
| $t_{1/2,SC}$ | Terminal half-life following subcutaneous administration |
| TR | Tricuspid Regurgitant |
| TTE | Trans-Thoracic Echocardiogram |
| ULN | Upper Limits of Normal |
| $V_z/F$ | Apparent volume of distribution after non-intravenous administration |
| VSDL | Vessel Dilator or proANP (31-67) |
| WOCBP | Women of Child Bearing Potential |

We claim:

1. A method, comprising the steps of:
continuously administering a natriuretic peptide to a subject suffering from kidney disease alone, heart failure alone, or with concomitant kidney disease and heart failure or cardiorenal syndrome using a drug provisioning component to chronically deliver a therapeutically effective amount of the natriuretic peptide to the subject at a rate which maintains a subject-specific mean steady state plasma concentration, and
maintaining the plasma concentration of the natriuretic peptide within a specified range,
wherein the specified range is pre-determined by administering a test dose of the natriuretic peptide to the subject so that the specified range is not greater than a plasma concentration of the natriuretic peptide reached in the subject during either a subcutaneous bolus at 18,000 ng/kg or a 1 hour intravenous infusion of the natriuretic peptide at 300 ng/(kg·min) based on the subject's body weight, and
wherein the drug provisioning component delivers the natriuretic peptide subcutaneously for multiple days.

2. The method of claim 1, wherein the natriuretic peptide is selected from any one of long-acting natriuretic peptide (LANP), kaliuretic peptide (KP), urodilatin (URO), atrial natriuretic peptide (ANP), vessel dilator (VD) and brain natriuretic peptide (BNP).

3. The method of claim 1, wherein the drug provisioning component is selected from an external or implantable drug delivery pump, an implanted or percutaneous vascular access port, a direct delivery catheter system, and a local drug-release device, and the drug provisioning component delivers the natriuretic peptide at a fixed, pulsed, continuous or variable rate.

4. The method of claim 1, wherein the specified range is not greater than a plasma concentration of the natriuretic peptide reached during either a subcutaneous bolus of the natriuretic peptide at 6000 ng/kg or a 1 hour intravenous infusion of the natriuretic peptide at 100 ng/kg·min in the subject.

5. The method of claim 1, wherein the drug provisioning component subcutaneously delivers a therapeutically effective amount of the natriuretic peptide at a continuous rate (ng/kg of body weight) matching the area under the curve of a subcutaneous bolus at 6000 ng/kg of the subject.

6. The method of claim 1, further comprising the step of calculating a dosing schedule based on the subject's body weight.

7. The method of claim 6, further comprising the step of adjusting the dosing schedule to meet pharmacokinetic variables calculated from one or more subject parameters, wherein the pharmacokinetic variables are selected from any one of area under the curve, clearance, volume of distribution, half-life, elimination rates, minimum inhibitory concentrations, route of administration, endogenous concentrations of the natriuretic peptides, diurnal variation, and rate of drug delivery.

8. A method for administering a natriuretic peptide to a subject suffering from kidney disease alone, heart failure alone, or with concomitant kidney disease and heart failure or cardiorenal syndrome, comprising:
continuously administering the natriuretic peptide to the subject using a drug provisioning component to maintain a subject-specific plasma level of the natriuretic peptide at a steady state concentration at a specified range, wherein
the specified range is pre-determined by administering a test dose of the natriuretic peptide to the subject and the specified range maintains a plasma level of the natriuretic peptide at a steady state concentration from about 0.5 to about 60 ng/mL and the drug provisioning component administers the natriuretic peptide subcutaneously for multiple days,
the natriuretic peptide is selected from any one of long-acting natriuretic peptide (LANP), kaliuretic peptide (KP), urodilatin (URO), atrial natriuretic peptide (ANP), vessel dilator (VD) and brain natriuretic peptide (BNP), and
the administration of the natriuretic peptide has one or more renal protective, cardiovascular protective or renal or cardiovascular protective effects.

9. The method of claim 8, wherein the one or more renal protective, cardiovascular protective or renal or cardiovascular protective effects includes one or more selected from the group consisting of lowering blood pressure; lowering right atrial pressure; slowing, preventing or reversing a change in the glomerular filtration rate of the subject; increasing urine flow rate or sodium excretion rate; lowering the presence of albumin in urine or lowering the presence of protein in urine; reducing renal tissue damage; and increasing renal cortical blood flow.

10. The method of claim 8, wherein the natriuretic peptide is vessel dilator (VD).

11. The method of claim 8, wherein kidney disease is selected from the group consisting of Stage 1 kidney disease, Stage 2 kidney disease, Stage 3 kidney disease, Stage 4 kidney disease, Stage 5 kidney disease, and end-stage renal disease.

12. The method of claim 8, wherein cardiorenal syndrome (CRS) is selected from the group consisting of CRS Type I, CRS Type II, CRS Type III, CRS Type IV and CRS Type V.

13. The method of claim 8, wherein heart failure is selected from the group consisting of chronic heart failure, congestive heart failure, acute heart failure, decompensated heart failure, systolic heart failure, and diastolic heart failure.

* * * * *